United States Patent
Shelton, IV et al.

(10) Patent No.: US 11,361,176 B2
(45) Date of Patent: Jun. 14, 2022

(54) SURGICAL RFID ASSEMBLIES FOR COMPATIBILITY DETECTION

(71) Applicant: Ethicon LLC, Guaynabo, PR (US)

(72) Inventors: Frederick E. Shelton, IV, Hillsboro, OH (US); Kevin M. Fiebig, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 16/458,116

(22) Filed: Jun. 30, 2019

(65) Prior Publication Data

US 2020/0410180 A1 Dec. 31, 2020

Related U.S. Application Data

(60) Provisional application No. 62/868,457, filed on Jun. 28, 2019.

(51) Int. Cl.
| | |
|---|---|
| *G06K 7/08* | (2006.01) |
| *G06K 7/10* | (2006.01) |
| *A61B 90/98* | (2016.01) |
| *A61B 17/072* | (2006.01) |
| *A61B 17/10* | (2006.01) |

(Continued)

(52) U.S. Cl.
CPC .... *G06K 7/10475* (2013.01); *A61B 17/07207* (2013.01); *A61B 17/10* (2013.01); *A61B 17/34* (2013.01); *A61B 18/14* (2013.01); *A61B 90/98* (2016.02); *G06K 19/0723* (2013.01); *A61B 34/30* (2016.02); *A61B 2017/00061* (2013.01); *A61B 2017/00199* (2013.01); *A61B 2017/00221* (2013.01); *A61B 2017/00398* (2013.01); *A61B 2017/00734* (2013.01); *A61B 2017/07257* (2013.01); *A61B 2017/07271* (2013.01); *A61B 2018/0063* (2013.01); *A61B 2018/00601* (2013.01); *A61B 2018/00994* (2013.01); *A61B 2218/008* (2013.01)

(58) Field of Classification Search
CPC ... G06K 7/00; G06K 17/0022; G06K 17/0025
USPC .............................. 235/451, 462.46, 472.02
See application file for complete search history.

(56) References Cited

U.S. PATENT DOCUMENTS

| | | |
|---|---|---|
| 903,739 A | 11/1908 | Lesemann |
| 1,075,556 A | 10/1913 | Fenoughty |

(Continued)

FOREIGN PATENT DOCUMENTS

| | | |
|---|---|---|
| AU | 2012268848 A1 | 1/2013 |
| CN | 2785249 Y | 5/2006 |

(Continued)

OTHER PUBLICATIONS

IEEE Std 802.3-2012 (Revision of IEEE Std 802.3-2008, published Dec. 28, 2012.

(Continued)

*Primary Examiner* — Daniel St Cyr

(57) ABSTRACT

A control system for a surgical instrument. The control system comprises an RFID scanner and a control circuit coupled to the RFID scanner. The control circuit is configured to receive data from RFID tags associated with devices, determine whether the devices are compatible based on a comparison of the received data, and provide an alert that the devices are incompatible or a suggestion to replace one of the devices with a replacement compatible device.

23 Claims, 26 Drawing Sheets

(51) Int. Cl.
*A61B 17/34* (2006.01)
*A61B 18/14* (2006.01)
*G06K 19/07* (2006.01)
*A61B 34/30* (2016.01)
*A61B 17/00* (2006.01)
*A61B 18/00* (2006.01)

(56) References Cited

U.S. PATENT DOCUMENTS

| | | | |
|---|---|---|---|
| 1,082,105 A | 12/1913 | Anderson |
| 2,420,552 A | 5/1947 | Morrill |
| 2,825,178 A | 3/1958 | Hawkins |
| 3,315,863 A | 4/1967 | O'Dea |
| 3,604,561 A | 9/1971 | Mallina et al. |
| 3,685,250 A | 8/1972 | Henry et al. |
| 3,887,393 A | 6/1975 | La Rue, Jr. |
| 3,999,110 A | 12/1976 | Ramstrom et al. |
| 4,149,461 A | 4/1979 | Simeth |
| 4,160,857 A | 7/1979 | Nardella et al. |
| 4,203,444 A | 5/1980 | Bonnell et al. |
| 4,476,864 A | 10/1984 | Tezel |
| 4,481,458 A | 11/1984 | Lane |
| 4,514,477 A | 4/1985 | Kobayashi |
| 4,868,958 A | 9/1989 | Suzuki et al. |
| 4,976,173 A | 12/1990 | Yang |
| 5,009,222 A | 4/1991 | Her |
| 5,100,422 A | 3/1992 | Berguer et al. |
| 5,164,652 A | 11/1992 | Johnson et al. |
| 5,269,794 A | 12/1993 | Rexroth |
| 5,302,148 A | 4/1994 | Heinz |
| 5,308,353 A | 5/1994 | Beurrier |
| 5,308,358 A | 5/1994 | Bond et al. |
| 5,350,104 A | 9/1994 | Main et al. |
| 5,389,072 A | 2/1995 | Imran |
| 5,431,645 A | 7/1995 | Smith et al. |
| 5,487,377 A | 1/1996 | Smith et al. |
| 5,509,918 A | 4/1996 | Romano |
| 5,626,979 A | 5/1997 | Mitsui et al. |
| 5,637,110 A | 6/1997 | Pennybacker et al. |
| 5,656,917 A | 8/1997 | Theobald |
| 5,664,404 A | 9/1997 | Ivanov et al. |
| 5,716,352 A | 2/1998 | Viola et al. |
| 5,732,712 A | 3/1998 | Adair |
| 5,736,271 A | 4/1998 | Cisar et al. |
| 5,762,458 A | 6/1998 | Wang et al. |
| 5,766,186 A | 6/1998 | Faraz et al. |
| 5,769,640 A | 6/1998 | Jacobus et al. |
| 5,868,664 A | 2/1999 | Speier et al. |
| 5,881,943 A | 3/1999 | Heck et al. |
| 5,907,664 A | 5/1999 | Wang et al. |
| 6,019,780 A | 2/2000 | Lombardo et al. |
| 6,094,021 A | 7/2000 | Noro et al. |
| RE36,923 E | 10/2000 | Hiroi et al. |
| 6,361,542 B1 | 3/2002 | Dimitriu et al. |
| 6,364,828 B1 | 4/2002 | Yeung et al. |
| 6,482,063 B1 | 11/2002 | Frigard |
| 6,500,189 B1 | 12/2002 | Lang et al. |
| 6,506,399 B2 | 1/2003 | Donovan |
| 6,554,844 B2 | 4/2003 | Lee et al. |
| 6,572,629 B2 | 6/2003 | Kalloo et al. |
| 6,595,914 B2 | 7/2003 | Kato |
| 6,626,938 B1 | 9/2003 | Butaric et al. |
| 6,755,825 B2 | 6/2004 | Shoenman et al. |
| 6,801,009 B2 | 10/2004 | Makaran et al. |
| 6,887,244 B1 | 5/2005 | Walker et al. |
| 6,949,196 B2 | 9/2005 | Schmitz et al. |
| 7,081,318 B2 | 7/2006 | Lee et al. |
| 7,197,965 B1 | 4/2007 | Anderson |
| 7,205,959 B2 | 4/2007 | Henriksson |
| 7,226,467 B2 | 6/2007 | Lucatero et al. |
| 7,336,183 B2 | 2/2008 | Reddy et al. |
| 7,354,398 B2 | 4/2008 | Kanazawa |
| 7,497,137 B2 | 3/2009 | Tellenbach et al. |
| 7,605,826 B2 | 10/2009 | Sauer |
| 7,618,427 B2 | 11/2009 | Ortiz et al. |
| 7,706,853 B2 | 4/2010 | Hacker et al. |
| 7,709,136 B2 | 5/2010 | Touchton et al. |
| 7,735,704 B2 | 6/2010 | Bilotti |
| 7,779,614 B1 | 8/2010 | McGonagle et al. |
| 7,782,382 B2 | 8/2010 | Fujimura |
| 7,819,894 B2 | 10/2010 | Mitsuishi et al. |
| 7,845,912 B2 | 12/2010 | Sung et al. |
| 7,887,755 B2 | 2/2011 | Mingerink et al. |
| 7,942,300 B2 | 5/2011 | Rethy et al. |
| 7,948,381 B2 | 5/2011 | Lindsay et al. |
| 7,981,025 B2 | 7/2011 | Pool et al. |
| 8,028,835 B2 | 10/2011 | Yasuda et al. |
| 8,038,044 B2 | 10/2011 | Viola |
| 8,114,345 B2 | 2/2012 | Dlugos, Jr. et al. |
| 8,157,834 B2 | 4/2012 | Conlon |
| 8,235,274 B2 | 8/2012 | Cappola |
| 8,328,065 B2 | 12/2012 | Shah |
| 8,377,059 B2 | 2/2013 | Deville et al. |
| 8,400,108 B2 | 3/2013 | Powell et al. |
| 8,439,830 B2 | 5/2013 | McKinley et al. |
| 8,486,047 B2 | 7/2013 | Stopek |
| 8,499,994 B2 | 8/2013 | D'Arcangelo |
| 8,523,882 B2 | 9/2013 | Huitema et al. |
| 8,585,598 B2 | 11/2013 | Razzaque et al. |
| 8,591,400 B2 | 11/2013 | Sugiyama |
| 8,613,384 B2 | 12/2013 | Pastorelli et al. |
| 8,617,155 B2 | 12/2013 | Johnson et al. |
| 8,672,209 B2 | 3/2014 | Crainich |
| 8,795,159 B2 | 8/2014 | Moriyama |
| 8,828,046 B2 | 9/2014 | Stefanchik et al. |
| 8,869,912 B2 | 10/2014 | Roßkamp et al. |
| 8,869,913 B2 | 10/2014 | Matthias et al. |
| 8,876,698 B2 | 11/2014 | Sakamoto et al. |
| 8,882,660 B2 | 11/2014 | Phee et al. |
| 8,882,792 B2 | 11/2014 | Dietz et al. |
| 8,884,560 B2 | 11/2014 | Ito |
| 8,910,847 B2 | 12/2014 | Nalagatla et al. |
| 8,915,842 B2 | 12/2014 | Weisenburgh, II et al. |
| 8,931,692 B2 | 1/2015 | Sancak |
| 8,939,898 B2 | 1/2015 | Omoto |
| 8,945,098 B2 | 2/2015 | Seibold et al. |
| 8,961,542 B2 | 2/2015 | Whitfield et al. |
| 8,984,711 B2 | 3/2015 | Ota et al. |
| 9,004,799 B1 | 4/2015 | Tibbits |
| 9,017,849 B2 | 4/2015 | Stulen et al. |
| 9,017,851 B2 | 4/2015 | Felder et al. |
| 9,028,468 B2 | 5/2015 | Scarfogliero et al. |
| 9,040,062 B2 | 5/2015 | Maeda et al. |
| 9,044,238 B2 | 6/2015 | Orszulak |
| 9,050,089 B2 | 6/2015 | Orszulak |
| 9,070,068 B2 | 6/2015 | Coveley et al. |
| 9,084,586 B2 | 7/2015 | Hafner et al. |
| 9,099,922 B2 | 8/2015 | Toosky et al. |
| 9,101,359 B2 | 8/2015 | Smith et al. |
| 9,167,960 B2 | 10/2015 | Yamaguchi et al. |
| 9,179,832 B2 | 11/2015 | Diolaiti |
| D746,459 S | 12/2015 | Kaercher et al. |
| 9,220,504 B2 | 12/2015 | Viola et al. |
| 9,226,760 B2 | 1/2016 | Shelton, IV |
| 9,241,758 B2 | 1/2016 | Franer et al. |
| 9,265,510 B2 | 2/2016 | Dietzel et al. |
| 9,301,811 B2 | 4/2016 | Goldberg et al. |
| 9,314,291 B2 | 4/2016 | Schall et al. |
| 9,339,342 B2 | 5/2016 | Prisco et al. |
| 9,358,065 B2 | 6/2016 | Ladtkow et al. |
| 9,364,223 B2 | 6/2016 | Scirica |
| 9,370,361 B2 | 6/2016 | Viola et al. |
| 9,385,640 B2 | 7/2016 | Sun et al. |
| 9,392,885 B2 | 7/2016 | Vogler et al. |
| 9,393,354 B2 | 7/2016 | Freedman et al. |
| 9,396,369 B1 | 7/2016 | Whitehurst et al. |
| 9,398,905 B2 | 7/2016 | Martin |
| 9,408,605 B1 | 8/2016 | Knodel et al. |
| 9,429,204 B2 | 8/2016 | Stefan et al. |
| 9,463,012 B2 | 10/2016 | Bonutti et al. |
| 9,474,513 B2 | 10/2016 | Ishida et al. |
| 9,486,215 B2 | 11/2016 | Olson et al. |
| 9,504,520 B2 | 11/2016 | Worrell et al. |
| 9,507,399 B2 | 11/2016 | Chien |

(56) References Cited

U.S. PATENT DOCUMENTS

| | | | |
|---|---|---|---|
| 9,526,921 B2 | 12/2016 | Kimball et al. |
| 9,549,733 B2 | 1/2017 | Knodel |
| 9,549,750 B2 | 1/2017 | Shelton, IV et al. |
| 9,561,072 B2 | 2/2017 | Ko |
| 9,629,631 B2 | 4/2017 | Nicholas et al. |
| 9,675,348 B2 | 6/2017 | Smith et al. |
| 9,700,315 B2 | 7/2017 | Chen et al. |
| 9,700,334 B2 | 7/2017 | Hinman et al. |
| 9,702,823 B2 | 7/2017 | Maher et al. |
| 9,730,757 B2 | 8/2017 | Brudniok |
| 9,737,298 B2 | 8/2017 | Isbell, Jr. |
| 9,815,118 B1 | 11/2017 | Schmitt et al. |
| 9,839,481 B2 | 12/2017 | Blumenkranz et al. |
| 9,867,617 B2 | 1/2018 | Ma |
| 9,888,914 B2 | 2/2018 | Martin et al. |
| 9,907,552 B2 | 3/2018 | Measamer et al. |
| 9,987,008 B2 | 6/2018 | Scirica et al. |
| 9,993,284 B2 | 6/2018 | Boudreaux |
| 10,022,120 B2 | 7/2018 | Martin et al. |
| 10,022,123 B2 | 7/2018 | Williams et al. |
| 10,045,869 B2 | 8/2018 | Forsell |
| 10,064,622 B2 | 9/2018 | Murthy Aravalli |
| 10,080,552 B2 | 9/2018 | Nicholas et al. |
| D830,550 S | 10/2018 | Miller et al. |
| 10,105,126 B2 | 10/2018 | Sauer |
| 10,105,149 B2 | 10/2018 | Haider et al. |
| 10,111,665 B2 | 10/2018 | Aranyi et al. |
| D833,608 S | 11/2018 | Miller et al. |
| 10,123,845 B2 | 11/2018 | Yeung |
| 10,130,382 B2 | 11/2018 | Gladstone |
| 10,161,816 B2 | 12/2018 | Jackson et al. |
| 10,163,065 B1 * | 12/2018 | Koski ............ G06Q 10/063112 |
| 10,164,466 B2 | 12/2018 | Calderoni |
| 10,188,389 B2 | 1/2019 | Vendely et al. |
| 10,213,204 B2 | 2/2019 | Aranyi et al. |
| 10,285,700 B2 | 5/2019 | Scheib |
| 10,303,851 B2 | 5/2019 | Nguyen et al. |
| 10,314,578 B2 | 6/2019 | Leimbach et al. |
| 10,314,580 B2 | 6/2019 | Scheib et al. |
| 10,349,937 B2 | 7/2019 | Williams |
| 10,413,155 B2 | 9/2019 | Inoue |
| 10,420,551 B2 | 9/2019 | Calderoni |
| D865,174 S | 10/2019 | Auld et al. |
| D865,175 S | 10/2019 | Widenhouse et al. |
| 10,478,185 B2 | 11/2019 | Nicholas |
| 10,482,292 B2 | 11/2019 | Clouser et al. |
| 10,500,000 B2 | 12/2019 | Swayze et al. |
| 10,542,976 B2 | 1/2020 | Calderoni et al. |
| 10,568,493 B2 | 2/2020 | Blase et al. |
| 10,588,231 B2 | 3/2020 | Sgroi, Jr. et al. |
| 10,603,041 B2 | 3/2020 | Miller et al. |
| 10,610,346 B2 | 4/2020 | Schwartz |
| 10,631,858 B2 | 4/2020 | Burbank |
| 10,645,905 B2 | 5/2020 | Gandola et al. |
| 10,646,292 B2 | 5/2020 | Solomon et al. |
| 10,667,408 B2 | 5/2020 | Sgroi, Jr. et al. |
| D888,953 S | 6/2020 | Baxter, III et al. |
| 10,667,818 B2 | 6/2020 | McLain et al. |
| 10,674,895 B2 | 6/2020 | Yeung et al. |
| 10,675,102 B2 | 6/2020 | Forgione et al. |
| 10,687,819 B2 | 6/2020 | Stokes et al. |
| D893,717 S | 8/2020 | Messerly et al. |
| 10,736,616 B2 | 8/2020 | Scheib et al. |
| 10,772,628 B2 | 9/2020 | Chen et al. |
| 10,842,473 B2 | 11/2020 | Scheib et al. |
| D904,612 S | 12/2020 | Wynn et al. |
| 10,849,621 B2 | 12/2020 | Whitfield et al. |
| 10,849,623 B2 | 12/2020 | Dunki-Jacobs et al. |
| 10,849,697 B2 | 12/2020 | Yates et al. |
| 10,874,392 B2 | 12/2020 | Scirica et al. |
| 10,874,393 B2 | 12/2020 | Satti, III et al. |
| D908,216 S | 1/2021 | Messerly et al. |
| 10,892,899 B2 | 1/2021 | Shelton, IV et al. |
| D910,847 S | 2/2021 | Shelton, IV et al. |
| 10,919,156 B2 | 2/2021 | Roberts et al. |
| D914,878 S | 3/2021 | Shelton, IV et al. |
| 10,932,804 B2 | 3/2021 | Scheib et al. |
| 10,932,872 B2 | 3/2021 | Shelton, IV et al. |
| 10,944,728 B2 | 3/2021 | Wiener et al. |
| 10,952,708 B2 | 3/2021 | Scheib et al. |
| D917,500 S | 4/2021 | Siebel et al. |
| 10,966,791 B2 | 4/2021 | Harris et al. |
| 10,973,520 B2 | 4/2021 | Shelton, IV et al. |
| 10,987,178 B2 | 4/2021 | Shelton, IV et al. |
| 11,013,563 B2 | 5/2021 | Shelton, IV et al. |
| 11,020,016 B2 | 6/2021 | Wallace et al. |
| 11,026,751 B2 | 6/2021 | Shelton, IV et al. |
| 11,090,047 B2 | 8/2021 | Shelton, IV et al. |
| 11,123,069 B2 | 9/2021 | Baxter, III et al. |
| 11,202,633 B2 | 12/2021 | Harris et al. |
| 2002/0023126 A1 | 2/2002 | Flavin |
| 2002/0138086 A1 | 9/2002 | Sixto et al. |
| 2003/0047230 A1 | 3/2003 | Kim |
| 2003/0050654 A1 | 3/2003 | Whitman et al. |
| 2003/0163029 A1 | 8/2003 | Sonnenschein et al. |
| 2004/0034287 A1 | 2/2004 | Hickle |
| 2004/0093020 A1 | 5/2004 | Sinton |
| 2004/0239582 A1 | 12/2004 | Seymour |
| 2005/0120836 A1 | 6/2005 | Anderson |
| 2005/0191936 A1 | 9/2005 | Marine et al. |
| 2005/0242950 A1 | 11/2005 | Lindsay et al. |
| 2005/0256546 A1 | 11/2005 | Vaisnys et al. |
| 2005/0258963 A1 | 11/2005 | Rodriguez et al. |
| 2006/0020167 A1 | 1/2006 | Sitzmann |
| 2006/0226957 A1 | 10/2006 | Miller et al. |
| 2006/0244652 A1 * | 11/2006 | Tethrake .................. A61B 90/00 342/44 |
| 2006/0247584 A1 | 11/2006 | Sheetz et al. |
| 2007/0001839 A1 * | 1/2007 | Cambre .................. G06Q 10/08 340/539.12 |
| 2007/0005045 A1 | 1/2007 | Mintz et al. |
| 2007/0152829 A1 | 7/2007 | Lindsay et al. |
| 2007/0191915 A1 | 8/2007 | Strother et al. |
| 2007/0260132 A1 | 11/2007 | Sterling |
| 2008/0068197 A1 * | 3/2008 | Neubauer ............... A61B 90/98 340/686.1 |
| 2008/0069736 A1 | 3/2008 | Mingerink et al. |
| 2008/0081948 A1 | 4/2008 | Weisenburgh et al. |
| 2008/0083811 A1 | 4/2008 | Marczyk |
| 2008/0208058 A1 | 8/2008 | Sabata et al. |
| 2008/0234866 A1 | 9/2008 | Kishi et al. |
| 2008/0243088 A1 | 10/2008 | Evans |
| 2008/0255420 A1 | 10/2008 | Lee et al. |
| 2009/0135280 A1 | 5/2009 | Johnston et al. |
| 2009/0209990 A1 * | 8/2009 | Yates ..................... A61B 90/98 606/169 |
| 2009/0273353 A1 | 11/2009 | Kroh et al. |
| 2009/0277288 A1 | 11/2009 | Doepker et al. |
| 2010/0016853 A1 | 1/2010 | Burbank |
| 2010/0030239 A1 | 2/2010 | Viola et al. |
| 2010/0069833 A1 | 3/2010 | Wenderow et al. |
| 2010/0234687 A1 | 9/2010 | Azarbarzin et al. |
| 2010/0291184 A1 | 11/2010 | Clark et al. |
| 2011/0028991 A1 | 2/2011 | Ikeda et al. |
| 2011/0056717 A1 | 3/2011 | Herisse |
| 2011/0095067 A1 | 4/2011 | Ohdaira |
| 2011/0118708 A1 | 5/2011 | Burbank et al. |
| 2011/0235168 A1 | 9/2011 | Sander |
| 2011/0251606 A1 | 10/2011 | Kerr |
| 2011/0285507 A1 | 11/2011 | Nelson |
| 2011/0292258 A1 | 12/2011 | Adler et al. |
| 2012/0008880 A1 | 1/2012 | Toth |
| 2012/0078243 A1 | 3/2012 | Worrell et al. |
| 2012/0190964 A1 | 7/2012 | Hyde et al. |
| 2012/0316424 A1 | 12/2012 | Stope |
| 2013/0075447 A1 | 3/2013 | Weisenburgh, II et al. |
| 2013/0112729 A1 | 5/2013 | Beardsley et al. |
| 2013/0172713 A1 | 7/2013 | Kirschenman |
| 2013/0183769 A1 | 7/2013 | Tajima |
| 2013/0231681 A1 | 9/2013 | Robinson et al. |
| 2013/0284792 A1 | 10/2013 | Ma |
| 2013/0293353 A1 | 11/2013 | McPherson et al. |
| 2013/0303845 A1 | 11/2013 | Skula et al. |
| 2014/0008289 A1 | 1/2014 | Williams et al. |

(56) References Cited

U.S. PATENT DOCUMENTS

| | | |
|---|---|---|
| 2014/0041191 A1 | 2/2014 | Knodel |
| 2014/0107697 A1 | 4/2014 | Patani et al. |
| 2014/0155916 A1 | 6/2014 | Hodgkinson et al. |
| 2014/0183244 A1 | 7/2014 | Duque et al. |
| 2014/0262408 A1 | 9/2014 | Woodard |
| 2014/0358163 A1 | 12/2014 | Farin et al. |
| 2015/0001272 A1 | 1/2015 | Sniffin et al. |
| 2015/0025571 A1 | 1/2015 | Suzuki et al. |
| 2015/0039010 A1 | 2/2015 | Beardsley et al. |
| 2015/0082624 A1 | 3/2015 | Craig et al. |
| 2015/0230794 A1 | 8/2015 | Wellman et al. |
| 2015/0297824 A1 | 10/2015 | Cabiri et al. |
| 2015/0367497 A1 | 12/2015 | Ito et al. |
| 2016/0029998 A1 | 2/2016 | Brister et al. |
| 2016/0030043 A1 | 2/2016 | Fanelli et al. |
| 2016/0074035 A1 | 3/2016 | Whitman et al. |
| 2016/0139666 A1 | 5/2016 | Rubin et al. |
| 2016/0242855 A1 | 8/2016 | Fichtinger et al. |
| 2016/0270781 A1 | 9/2016 | Scirica |
| 2016/0302820 A1 | 10/2016 | Hibner et al. |
| 2016/0314717 A1 | 10/2016 | Grubbs |
| 2016/0345972 A1 | 12/2016 | Beardsley et al. |
| 2016/0374716 A1 | 12/2016 | Kessler |
| 2017/0007234 A1 | 1/2017 | Chin et al. |
| 2017/0095315 A1* | 4/2017 | van der Weide ...... A61B 90/39 |
| 2017/0106302 A1 | 4/2017 | Cummings et al. |
| 2017/0135711 A1 | 5/2017 | Overmyer et al. |
| 2017/0135717 A1 | 5/2017 | Boudreaux et al. |
| 2017/0135747 A1 | 5/2017 | Broderick et al. |
| 2017/0172549 A1 | 6/2017 | Smaby et al. |
| 2017/0231629 A1 | 8/2017 | Stopek et al. |
| 2017/0242455 A1 | 8/2017 | Dickens |
| 2017/0245949 A1 | 8/2017 | Randle |
| 2017/0255799 A1 | 9/2017 | Zhao et al. |
| 2017/0270323 A1* | 9/2017 | Butler ................ G06K 7/10198 |
| 2017/0319047 A1 | 11/2017 | Poulsen et al. |
| 2018/0049794 A1 | 2/2018 | Swayze et al. |
| 2018/0051780 A1 | 2/2018 | Shelton, IV et al. |
| 2018/0055501 A1 | 3/2018 | Zemlok et al. |
| 2018/0085120 A1 | 3/2018 | Viola |
| 2018/0133521 A1 | 5/2018 | Frushour et al. |
| 2018/0153634 A1 | 6/2018 | Zemlok et al. |
| 2018/0168572 A1 | 6/2018 | Burbank |
| 2018/0168574 A1 | 6/2018 | Robinson et al. |
| 2018/0168754 A1 | 6/2018 | Overmyer |
| 2018/0235609 A1 | 8/2018 | Harris et al. |
| 2018/0236181 A1 | 8/2018 | Marlin et al. |
| 2018/0242970 A1 | 8/2018 | Mozdzierz |
| 2018/0289371 A1 | 10/2018 | Wang et al. |
| 2018/0296290 A1 | 10/2018 | Namiki et al. |
| 2018/0317905 A1 | 11/2018 | Olson et al. |
| 2018/0368066 A1 | 12/2018 | Howell et al. |
| 2018/0372806 A1 | 12/2018 | Laughery et al. |
| 2019/0008515 A1 | 1/2019 | Beardsley et al. |
| 2019/0038285 A1 | 2/2019 | Mozdzierz |
| 2019/0110779 A1 | 4/2019 | Gardner et al. |
| 2019/0125324 A1 | 5/2019 | Scheib et al. |
| 2019/0125342 A1 | 5/2019 | Beardsley et al. |
| 2019/0125384 A1 | 5/2019 | Scheib et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125459 A1 | 5/2019 | Shelton, IV et al. |
| 2019/0138770 A1 | 5/2019 | Compaijen et al. |
| 2019/0151029 A1 | 5/2019 | Robinson |
| 2019/0175847 A1 | 6/2019 | Pocreva, III et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201033 A1 | 7/2019 | Yates et al. |
| 2019/0201104 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201118 A1 | 7/2019 | Shelton, IV et al. |
| 2019/0201120 A1 | 7/2019 | Shelton, IV et al. |
| 2019/0201135 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201145 A1 | 7/2019 | Shelton, IV et al. |
| 2019/0205001 A1 | 7/2019 | Messerly et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206551 A1 | 7/2019 | Yates et al. |
| 2019/0206555 A1 | 7/2019 | Morgan et al. |
| 2019/0206561 A1 | 7/2019 | Shelton, IV et al. |
| 2019/0261983 A1 | 8/2019 | Granger et al. |
| 2019/0261987 A1 | 8/2019 | Viola et al. |
| 2019/0282233 A1 | 9/2019 | Burbank et al. |
| 2019/0290266 A1 | 9/2019 | Scheib et al. |
| 2019/0290297 A1 | 9/2019 | Haider et al. |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0350581 A1 | 11/2019 | Baxter, III et al. |
| 2020/0015915 A1 | 1/2020 | Swayze et al. |
| 2020/0060523 A1 | 2/2020 | Matsuda et al. |
| 2020/0138534 A1 | 5/2020 | Garcia Kilroy et al. |
| 2020/0146676 A1 | 5/2020 | Yates et al. |
| 2020/0197027 A1 | 6/2020 | Hershberger et al. |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0280219 A1 | 9/2020 | Laughery et al. |
| 2020/0305872 A1 | 10/2020 | Weidner et al. |
| 2020/0330181 A1 | 10/2020 | Junger et al. |
| 2020/0405416 A1 | 12/2020 | Shelton, IV et al. |
| 2020/0405422 A1 | 12/2020 | Shelton, IV et al. |
| 2021/0022741 A1 | 1/2021 | Baxter, III et al. |
| 2021/0030416 A1 | 2/2021 | Shelton, IV et al. |
| 2021/0045742 A1 | 2/2021 | Shelton, IV et al. |
| 2021/0052271 A1 | 2/2021 | Harris et al. |
| 2021/0059661 A1 | 3/2021 | Schmid et al. |
| 2021/0059662 A1 | 3/2021 | Shelton, IV |
| 2021/0059664 A1 | 3/2021 | Hensel et al. |
| 2021/0059666 A1 | 3/2021 | Schmid et al. |
| 2021/0059669 A1 | 3/2021 | Yates et al. |
| 2021/0059670 A1 | 3/2021 | Overmyer et al. |
| 2021/0059671 A1 | 3/2021 | Shelton, IV et al. |
| 2021/0059672 A1 | 3/2021 | Giordano et al. |
| 2021/0059673 A1 | 3/2021 | Shelton, IV et al. |

(56) References Cited

U.S. PATENT DOCUMENTS

| | | |
|---|---|---|
| 2021/0068817 A1 | 3/2021 | Shelton, IV et al. |
| 2021/0068818 A1 | 3/2021 | Overmyer et al. |
| 2021/0068820 A1 | 3/2021 | Parihar et al. |
| 2021/0068829 A1 | 3/2021 | Miller et al. |
| 2021/0068830 A1 | 3/2021 | Baber et al. |
| 2021/0068831 A1 | 3/2021 | Baber et al. |
| 2021/0068832 A1 | 3/2021 | Yates et al. |
| 2021/0068835 A1 | 3/2021 | Shelton, IV et al. |
| 2021/0077092 A1 | 3/2021 | Parihar et al. |
| 2021/0077099 A1 | 3/2021 | Shelton, IV et al. |
| 2021/0077100 A1 | 3/2021 | Shelton, IV et al. |
| 2021/0077109 A1 | 3/2021 | Harris et al. |
| 2021/0085313 A1 | 3/2021 | Morgan et al. |
| 2021/0085314 A1 | 3/2021 | Schmid et al. |
| 2021/0085315 A1 | 3/2021 | Aronhalt et al. |
| 2021/0085316 A1 | 3/2021 | Harris et al. |
| 2021/0085317 A1 | 3/2021 | Miller et al. |
| 2021/0085318 A1 | 3/2021 | Swayze et al. |
| 2021/0085319 A1 | 3/2021 | Swayze et al. |
| 2021/0085320 A1 | 3/2021 | Leimbach et al. |
| 2021/0085321 A1 | 3/2021 | Shelton, IV et al. |
| 2021/0085325 A1 | 3/2021 | Shelton, IV et al. |
| 2021/0085326 A1 | 3/2021 | Vendely et al. |
| 2021/0093321 A1 | 4/2021 | Auld et al. |
| 2021/0093323 A1 | 4/2021 | Scirica et al. |
| 2021/0100541 A1 | 4/2021 | Shelton, IV et al. |
| 2021/0100550 A1 | 4/2021 | Shelton, IV et al. |
| 2021/0100982 A1 | 4/2021 | Laby et al. |
| 2021/0106333 A1 | 4/2021 | Shelton, IV et al. |
| 2021/0107031 A1 | 4/2021 | Bales, Jr. et al. |
| 2021/0121175 A1 | 4/2021 | Yates et al. |
| 2021/0128146 A1 | 5/2021 | Shelton, IV et al. |
| 2021/0137522 A1 | 5/2021 | Shelton, IV et al. |
| 2021/0186490 A1 | 6/2021 | Shelton, IV et al. |
| 2021/0186492 A1 | 6/2021 | Shelton, IV et al. |
| 2021/0186493 A1 | 6/2021 | Shelton, IV et al. |
| 2021/0186494 A1 | 6/2021 | Shelton, IV et al. |
| 2021/0186495 A1 | 6/2021 | Shelton, IV et al. |
| 2021/0186497 A1 | 6/2021 | Shelton, IV et al. |
| 2021/0186498 A1 | 6/2021 | Boudreaux et al. |
| 2021/0186499 A1 | 6/2021 | Shelton, IV et al. |
| 2021/0186500 A1 | 6/2021 | Shelton, IV et al. |
| 2021/0186501 A1 | 6/2021 | Shelton, IV et al. |
| 2021/0186502 A1 | 6/2021 | Shelton, IV et al. |
| 2021/0186503 A1 | 6/2021 | Shelton, IV et al. |
| 2021/0186504 A1 | 6/2021 | Shelton, IV et al. |
| 2021/0186505 A1 | 6/2021 | Shelton, IV et al. |
| 2021/0186506 A1 | 6/2021 | Shelton, IV et al. |
| 2021/0186507 A1 | 6/2021 | Shelton, IV et al. |
| 2021/0212691 A1 | 7/2021 | Smith et al. |
| 2021/0212776 A1 | 7/2021 | Schmitt et al. |
| 2021/0219976 A1 | 7/2021 | DiNardo et al. |
| 2021/0228209 A1 | 7/2021 | Shelton, IV et al. |
| 2021/0236117 A1 | 8/2021 | Morgan et al. |
| 2021/0236124 A1 | 8/2021 | Shelton, IV et al. |
| 2021/0244406 A1 | 8/2021 | Kerr et al. |
| 2021/0244407 A1 | 8/2021 | Shelton, IV et al. |
| 2021/0244410 A1 | 8/2021 | Swayze et al. |
| 2021/0244412 A1 | 8/2021 | Vendely et al. |
| 2021/0259681 A1 | 8/2021 | Shelton, IV et al. |
| 2021/0259687 A1 | 8/2021 | Gonzalez et al. |
| 2021/0259986 A1 | 8/2021 | Widenhouse et al. |
| 2021/0259987 A1 | 8/2021 | Widenhouse et al. |
| 2021/0267589 A1 | 9/2021 | Swayze et al. |
| 2021/0267592 A1 | 9/2021 | Baxter, III et al. |
| 2021/0267594 A1 | 9/2021 | Morgan et al. |
| 2021/0267595 A1 | 9/2021 | Posada et al. |
| 2021/0267596 A1 | 9/2021 | Fanelli et al. |
| 2021/0275053 A1 | 9/2021 | Shelton, IV et al. |
| 2021/0275172 A1 | 9/2021 | Harris et al. |
| 2021/0275173 A1 | 9/2021 | Shelton, IV et al. |
| 2021/0275176 A1 | 9/2021 | Beckman et al. |
| 2021/0282767 A1 | 9/2021 | Shelton, IV et al. |
| 2021/0282769 A1 | 9/2021 | Baxter, III et al. |
| 2021/0282774 A1 | 9/2021 | Shelton, IV et al. |
| 2021/0282776 A1 | 9/2021 | Overmyer et al. |
| 2021/0290226 A1 | 9/2021 | Mandakolathur Vasudevan et al. |
| 2021/0290231 A1 | 9/2021 | Baxter, III et al. |
| 2021/0290232 A1 | 9/2021 | Harris et al. |
| 2021/0290233 A1 | 9/2021 | Shelton, IV et al. |
| 2021/0290236 A1 | 9/2021 | Moore et al. |
| 2021/0298745 A1 | 9/2021 | Leimbach et al. |
| 2021/0298746 A1 | 9/2021 | Leimbach et al. |
| 2021/0307748 A1 | 10/2021 | Harris et al. |
| 2021/0307754 A1 | 10/2021 | Shelton, IV et al. |
| 2021/0315566 A1 | 10/2021 | Yates et al. |
| 2021/0315570 A1 | 10/2021 | Shelton, IV |
| 2021/0315571 A1 | 10/2021 | Swayze et al. |
| 2021/0315573 A1 | 10/2021 | Shelton, IV et al. |
| 2021/0315574 A1 | 10/2021 | Shelton, IV et al. |
| 2021/0315576 A1 | 10/2021 | Shelton, IV et al. |
| 2021/0315577 A1 | 10/2021 | Shelton, IV et al. |
| 2021/0322009 A1 | 10/2021 | Huang et al. |
| 2021/0330321 A1 | 10/2021 | Leimbach et al. |
| 2021/0338233 A1 | 11/2021 | Shelton, IV et al. |
| 2021/0338234 A1 | 11/2021 | Shelton, IV et al. |
| 2021/0369273 A1 | 12/2021 | Yates et al. |
| 2021/0378669 A1 | 12/2021 | Shelton, IV et al. |

FOREIGN PATENT DOCUMENTS

| | | |
|---|---|---|
| CN | 101273908 A | 10/2008 |
| CN | 101756727 A | 6/2010 |
| CN | 102743201 A | 10/2012 |
| CN | 103083053 A | 5/2013 |
| CN | 103635150 A | 3/2014 |
| CN | 103860221 A | 6/2014 |
| CN | 104027145 A | 9/2014 |
| CN | 204520822 U | 8/2015 |
| CN | 105919642 A | 9/2016 |
| CN | 105997173 A | 10/2016 |
| CN | 208625784 U | 3/2019 |
| DE | 102004041871 A1 | 3/2006 |
| EP | 1064882 A1 | 1/2001 |
| EP | 1558161 A1 | 8/2005 |
| EP | 2789299 A1 | 10/2014 |
| EP | 2878274 A1 | 6/2015 |
| EP | 3476334 A1 | 5/2019 |
| ES | 1070456 U | 9/2009 |
| JP | H02106189 A | 4/1990 |
| JP | H06304176 A | 11/1994 |
| JP | 2000210299 A | 8/2000 |
| JP | 2001-69758 A | 3/2001 |
| JP | 2001208655 A | 8/2001 |
| JP | 2007-97252 A | 4/2007 |
| JP | 2007304057 A | 11/2007 |
| JP | 2008154804 A | 7/2008 |
| JP | 2010065594 A | 3/2010 |
| JP | 2011200665 A | 10/2011 |
| JP | 2013541982 A | 11/2013 |
| JP | 2014171879 A | 9/2014 |
| JP | 2015516838 A | 6/2015 |
| JP | 2015521524 A | 7/2015 |
| JP | 2016007800 A | 1/2016 |
| JP | 2016508792 A | 3/2016 |
| JP | 2016530949 A | 10/2016 |
| JP | 2017513563 A | 6/2017 |
| JP | 2019513530 A | 5/2019 |
| WO | WO-2019036490 A1 | 2/2019 |

OTHER PUBLICATIONS

"ATM-MPLS Network Interworking Version 2.0, af-aic-0178.001" ATM Standard, The ATM Forum Technical Committee, published Aug. 2003.

Yang et al.; "4D printing reconfigurable, deployable and mechanically tunable metamaterials," Material Horizions, vol. 6, pp. 1244-1250 (2019).

(56) References Cited

OTHER PUBLICATIONS

"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.

* cited by examiner

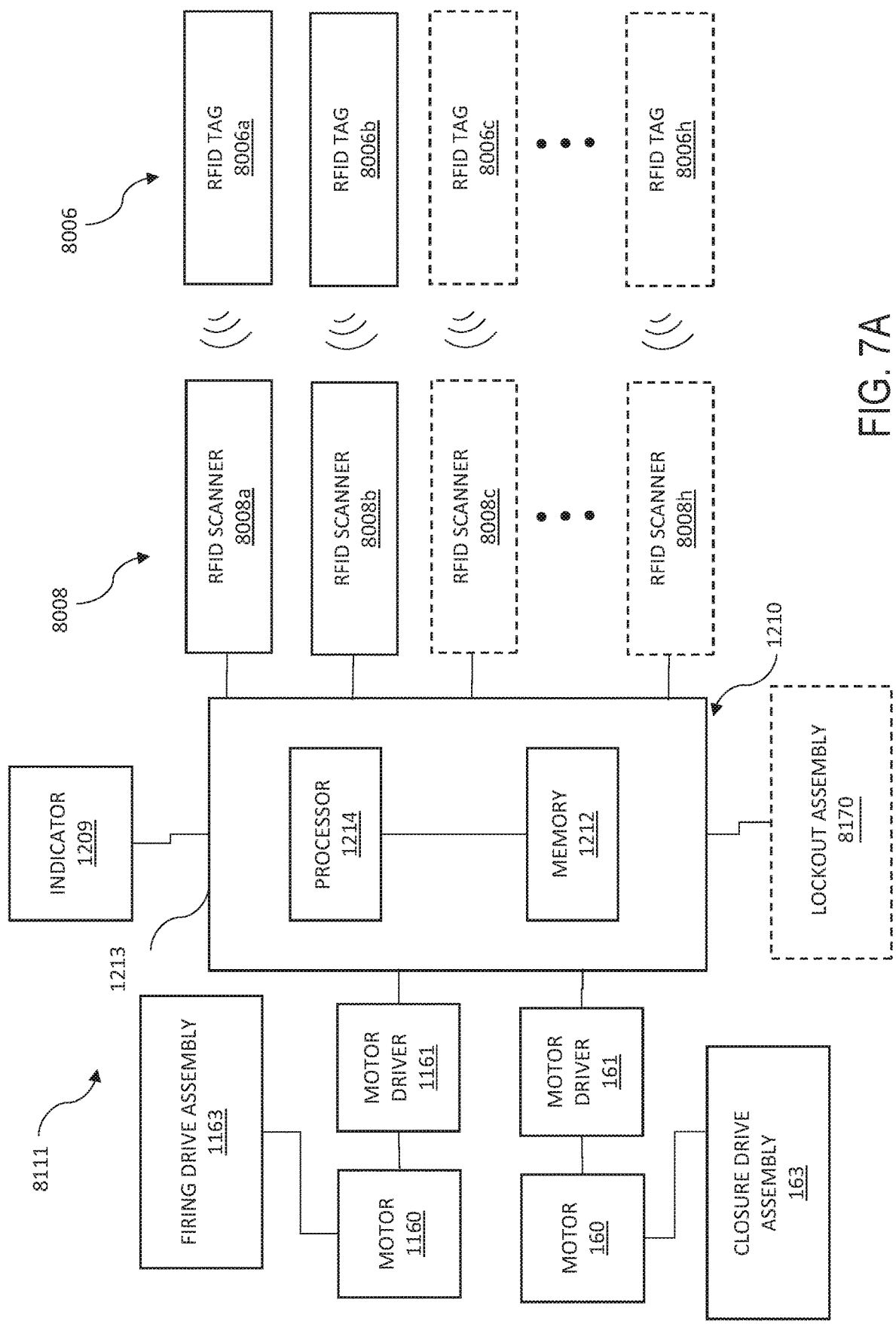

| RFID TAG | HOUSING ASSEMBLY | BATTERY | MOTOR/ GEARBOX | SHAFT | CARTRIDGE |
|---|---|---|---|---|---|
| Identifies: | • Device ID$_{tag}$ | • Battery ID$_{tag}$ | • Motor ID$_{tag}$ | • Shaft ID$_{tag}$<br>• Length(STD)<br>• Type: single axis artic. | • Cartridge ID$_{tag}$<br>• Length=60mm<br>• Color=blue<br>• Smart GST |
| Defines: | • Capabilities<br>• Mfg & date<br>• Communication capabilities & protocol<br>• Encryption methods | • Type of battery (e.g. rechargeable)<br>• Capability (e.g. 2.1 × std) | • Internal processor<br>• Control programs | • Wired communication bus with 4" × rate of thruput<br>• Sensing array type to communicate with cartridge & device | • Wake-up & communication protocol to talk w/cartridge<br>• Encryption key to decode signal<br>• What can be sensed? |

FIG. 12

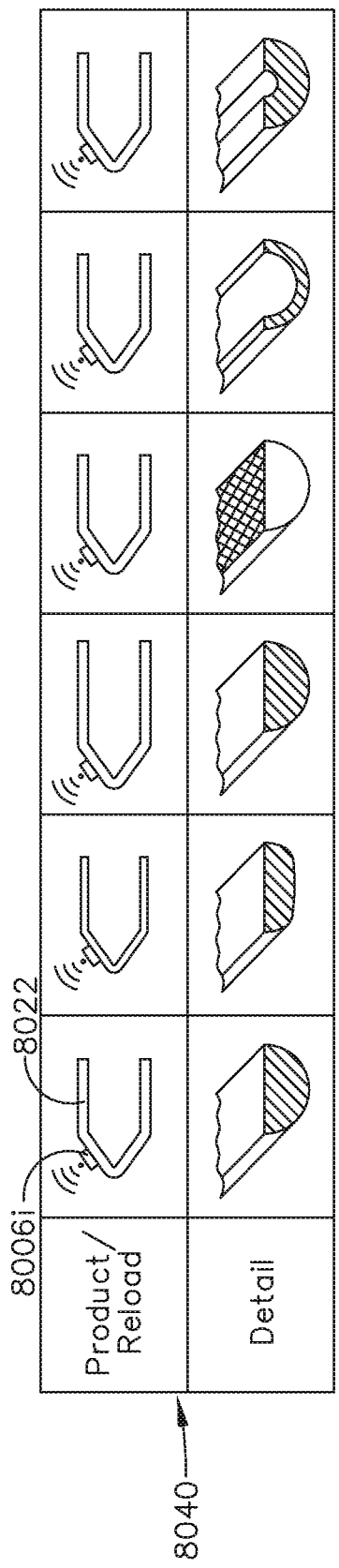
FIG. 15
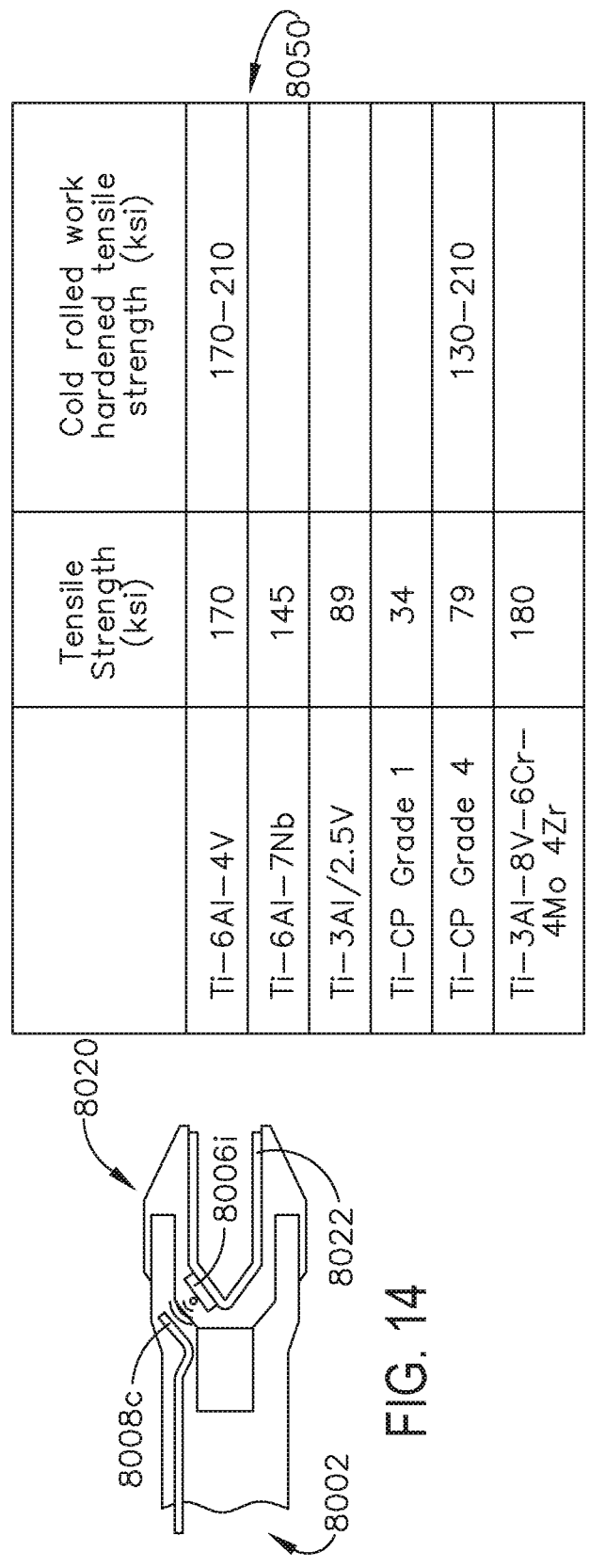
FIG. 16
FIG. 14

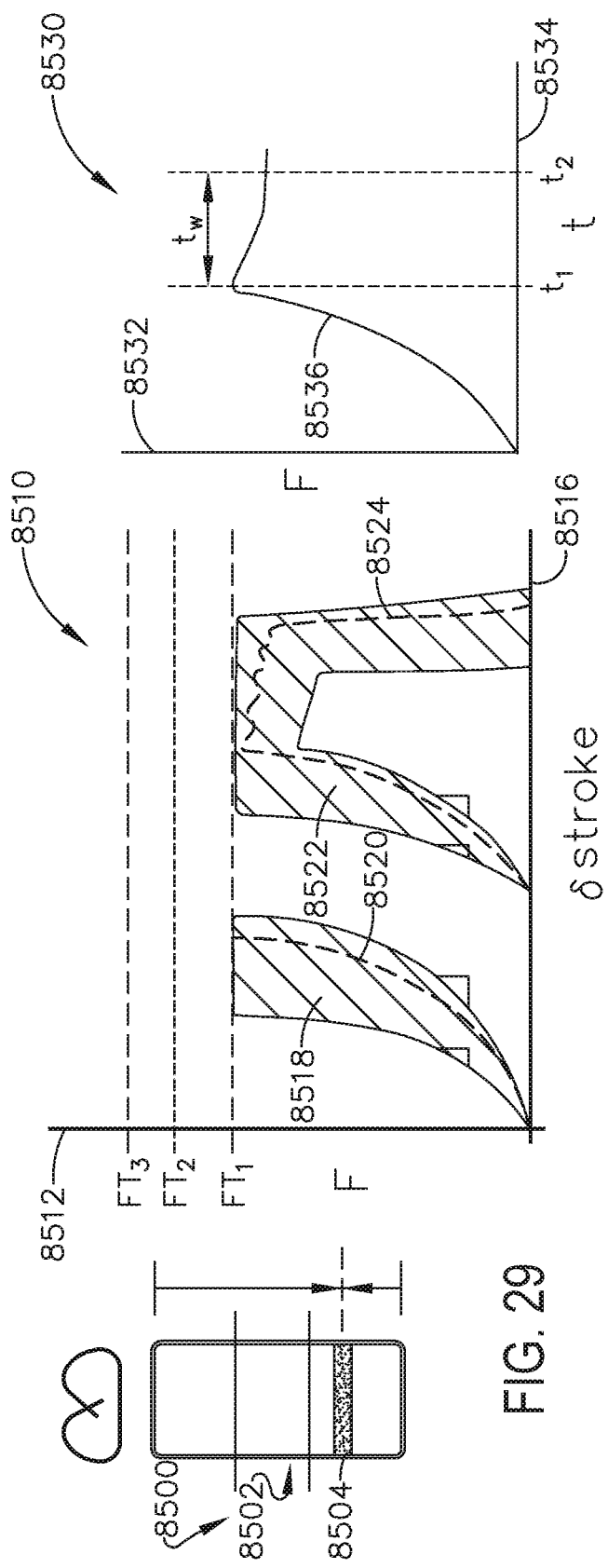

SURGICAL RFID ASSEMBLIES FOR COMPATIBILITY DETECTION

CROSS-REFERENCE TO RELATED APPLICATIONS

This application is a non-provisional application claiming priority under 35 U.S.C. § 119(e) to U.S. Provisional Patent Application Ser. No. 62/868,457, entitled SURGICAL SYSTEMS WITH MULTIPLE RFID TAGS, filed on Jun. 28, 2019, the entire disclosure of which is hereby incorporated by reference herein.

BACKGROUND

The present invention relates to surgical instruments and, in various embodiments, to surgical cutting and stapling instruments and staple cartridges therefor that are designed to cut and staple tissue. In various embodiments, RFID technology can be used to identify the components of a surgical instrument, such as staple cartridges, for example. Examples of surgical systems which use RFID technology can be found in the disclosures of U.S. Pat. No. 7,959,050, entitled ELECTRICALLY SELF-POWERED SURGICAL INSTRUMENT WITH MANUAL RELEASE, which issued on Jun. 14, 2011, and U.S. Patent Application No. 2015/0053743, entitled ERROR DETECTION ARRANGEMENTS FOR SURGICAL INSTRUMENT ASSEMBLIES, which published on Feb. 26, 2015, and both of which are incorporated by reference herein in their entireties.

SUMMARY

In various embodiments, a control system for a surgical instrument is disclosed. The control system includes an RFID scanner and a control circuit coupled to the RFID scanner. The control circuit is configured to receive a first datum from a first RFID tag associated with a first device via the RFID scanner, receive a second datum from a second RFID tag associated with a second device via the RFID scanner, and verify compatibility of the first device and the second device based on a comparison of the first datum and the second datum.

In various embodiments, a control system for a surgical instrument is disclosed. The control system includes an RFID scanner and a control circuit coupled to the RFID scanner. The control circuit is configured to receive a first datum from a first RFID tag associated with a first device via the RFID scanner, receive a second datum from a second RFID tag associated with a second device via the RFID scanner, determine that the first device is incompatible with the second device based on a comparison between the first datum and the second datum, and provide a suggestion for a third device as a replacement for the second device.

In various embodiments, a control system for a surgical instrument, the surgical instrument for use with a surgical system is disclosed. The control system includes an RFID scanner and a control circuit coupled to the RFID scanner. The control circuit is configured to receive a first datum from a first RFID tag associated with a first device via the RFID scanner, determine an operational setting for the surgical system according to the first datum, receive a second datum from a second RFID tag associated with a second device via the RFID scanner, and update the operational setting from a first value to a second value according to the first datum and the second datum.

BRIEF DESCRIPTION OF THE DRAWINGS

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

FIG. 7A depicts another control system of a surgical stapling instrument, in accordance with at least one aspect of the present disclosure.

FIG. 12 illustrates a table of surgical instrument component data, in accordance with at least one aspect of the present disclosure.

FIG. 14 illustrates a sectional view of a surgical instrument including an RFID scanner configured to detect an RFID tag associated with a consumable device, in accordance with at least one aspect of the present disclosure.

FIG. 15 illustrates a table of surfaces for various surgical clip types, in accordance with at least one aspect of the present disclosure.

FIG. 16 illustrates a table of mechanical properties for various surgical clip types, in accordance with at least one aspect of the present disclosure.

FIG. 29 illustrates a graphical user interface including a staple height widget, in accordance with at least one aspect of the present disclosure.

FIG. 30 illustrates a graph depicting force relative to displacement stroke for a surgical stapler firing as controlled by a control system, in accordance with at least one aspect of the present disclosure.

FIG. 31 illustrates a graph depicting force relative to time for a surgical stapler firing as controlled by a control system, in accordance with at least one aspect of the present disclosure.

DESCRIPTION

Figure 1:
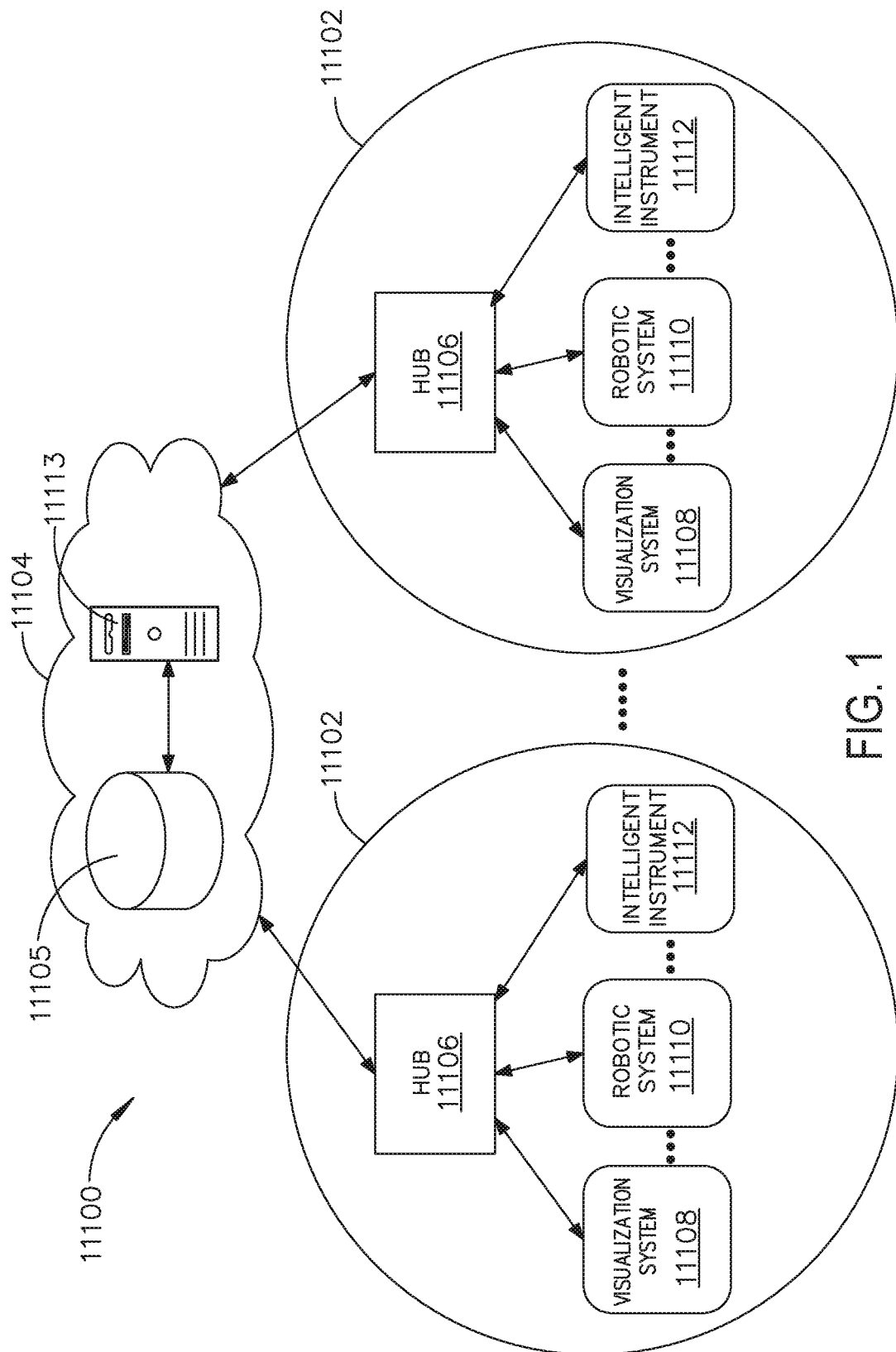
FIG. 1 is a block diagram of a computer-implemented interactive surgical system, in accordance with at least one aspect of the present disclosure.

Applicant of the present application owns the following U.S. patent applications that were filed on Jun. 30, 2019 and which are each herein incorporated by reference in their respective entireties:

U.S. patent application Ser. No. 16/458,104, entitled METHOD FOR AUTHENTICATING THE COMPATIBILITY OF A STAPLE CARTRIDGE WITH A SURGICAL INSTRUMENT, now U.S. Pat. No. 11,229,437;

U.S. patent application Ser. No. 16/458,108, entitled SURGICAL INSTRUMENT SYSTEM COMPRISING AN RFID SYSTEM, now U.S. Patent Application Publication No. 2020/0405436;

U.S. patent application Ser. No. 16/458,111, entitled SURGICAL INSTRUMENT COMPRISING AN RFID SYSTEM FOR TRACKING A MOVABLE COMPONENT, now U.S. Patent Application Publication No. 2020/0405437;

U.S. patent application Ser. No. 16/458,114, entitled SURGICAL INSTRUMENT COMPRISING AN ALIGNED RFID SENSOR, now U.S. Patent Application Publication No. 2020/0405438;

U.S. patent application Ser. No. 16/458,105, entitled SURGICAL STAPLING SYSTEM HAVING AN INFORMATION DECRYPTION PROTOCOL, now U.S. Patent Application Publication No. 2020/0405302;

U.S. patent application Ser. No. 16/458,110, entitled SURGICAL STAPLING SYSTEM HAVING AN INFORMATION ENCRYPTION PROTOCOL, now U.S. Pat. No. 11,259,803;

U.S. patent application Ser. No. 16/458,120, entitled SURGICAL STAPLING SYSTEM HAVING A LOCKOUT MECHANISM FOR AN INCOMPATIBLE CARTRIDGE, now U.S. Pat. No. 11,298,127;

U.S. patent application Ser. No. 16/458,125, entitled SURGICAL STAPLING SYSTEM HAVING A FRANGIBLE RFID TAG, now U.S. Pat. No. 11,246,678; and U.S. patent application Ser. No. 16/458,103, entitled PACKAGING FOR A REPLACEABLE COMPONENT OF A SURGICAL STAPLING SYSTEM, now U.S. Patent Application Publication No. 2020/0405296.

Applicant of the present application owns the following U.S. patent applications that were filed on Jun. 30, 2019 and which are each herein incorporated by reference in their respective entireties:

U.S. patent application Ser. No. 16/458,107, entitled METHOD OF USING MULTIPLE RFID CHIPS WITH A SURGICAL ASSEMBLY, now U.S. Pat. No. 11,241,235;

U.S. patent application Ser. No. 16/458,109, entitled MECHANISMS FOR PROPER ANVIL ATTACHMENT SURGICAL STAPLING HEAD ASSEMBLY, now U.S. Patent Application Publication No. 2020/0405312;

U.S. patent application Ser. No. 16/458,119, entitled MECHANISMS FOR MOTOR CONTROL ADJUSTMENTS OF A MOTORIZED SURGICAL INSTRUMENT, now U.S. Patent Application Publication No. 2020/0405314;

U.S. patent application Ser. No. 16/458,115, entitled SURGICAL INSTRUMENT WITH BATTERY COMPATIBILITY VERIFICATION FUNCTIONALITY, now U.S. Pat. No. 11,291,451;

U.S. patent application Ser. No. 16/458,117, entitled SURGICAL SYSTEM WITH RFID TAGS FOR UPDATING MOTOR ASSEMBLY PARAMETERS, now U.S. Patent Application Publication No. 2020/0405439;

U.S. patent application Ser. No. 16/458,121, entitled SURGICAL SYSTEMS WITH MULTIPLE RFID TAGS, now U.S. Pat. No. 11,224,497;

U.S. patent application Ser. No. 16/458,122, entitled RFID IDENTIFICATION SYSTEMS FOR SURGICAL INSTRUMENTS, now U.S. Patent Application Publication No. 2020/0410177;

U.S. patent application Ser. No. 16/458,106, entitled RFID IDENTIFICATION SYSTEMS FOR SURGICAL INSTRUMENTS, now U.S. Patent Application Publication No. 2020/0405316;

U.S. patent application Ser. No. 16/458,112, entitled SURGICAL RFID ASSEMBLIES FOR DISPLAY AND COMMUNICATION, now U.S. Patent Application Publication No. 2020/0405409; and U.S. patent application Ser. No. 16/458,118, entitled SURGICAL RFID ASSEMBLIES FOR INSTRUMENT OPERATIONAL SETTING CONTROL, now U.S. Patent Application Publication No. 2020/0405410.

Applicant of the present application owns the following U.S. patent applications that were filed on May 1, 2018 and which are each herein incorporated by reference in their respective entireties:

U.S. Provisional Patent Application Ser. No. 62/665,129, entitled SURGICAL SUTURING SYSTEMS;

U.S. Provisional Patent Application Ser. No. 62/665,139, entitled SURGICAL INSTRUMENTS COMPRISING CONTROL SYSTEMS;

U.S. Provisional Patent Application Ser. No. 62/665,177, entitled SURGICAL INSTRUMENTS COMPRISING HANDLE ARRANGEMENTS;

U.S. Provisional Patent Application Ser. No. 62/665,128, entitled MODULAR SURGICAL INSTRUMENTS;

U.S. Provisional Patent Application Ser. No. 62/665,192, entitled SURGICAL DISSECTORS; AND U.S. Provisional Patent Application Ser. No. 62/665,134, entitled SURGICAL CLIP APPLIER.

Applicant of the present application owns the following U.S. patent applications that were filed on Aug. 24, 2018 which are each herein incorporated by reference in their respective entireties:

U.S. patent application Ser. No. 16/112,129, entitled SURGICAL SUTURING INSTRUMENT CONFIGURED TO MANIPULATE TISSUE USING MECHANICAL AND ELECTRICAL POWER;

U.S. patent application Ser. No. 16/112,155, entitled SURGICAL SUTURING INSTRUMENT COMPRISING A CAPTURE WIDTH WHICH IS LARGER THAN TROCAR DIAMETER;

U.S. patent application Ser. No. 16/112,168, entitled SURGICAL SUTURING INSTRUMENT COMPRISING A NON-CIRCULAR NEEDLE;

U.S. patent application Ser. No. 16/112,180, entitled ELECTRICAL POWER OUTPUT CONTROL BASED ON MECHANICAL FORCES;

U.S. patent application Ser. No. 16/112,193, entitled REACTIVE ALGORITHM FOR SURGICAL SYSTEM;

U.S. patent application Ser. No. 16/112,099, entitled SURGICAL INSTRUMENT COMPRISING AN ADAPTIVE ELECTRICAL SYSTEM;

U.S. patent application Ser. No. 16/112,112, entitled CONTROL SYSTEM ARRANGEMENTS FOR A MODULAR SURGICAL INSTRUMENT;

U.S. patent application Ser. No. 16/112,119, entitled ADAPTIVE CONTROL PROGRAMS FOR A SURGICAL SYSTEM COMPRISING MORE THAN ONE TYPE OF CARTRIDGE;

U.S. patent application Ser. No. 16/112,097, entitled SURGICAL INSTRUMENT SYSTEMS COMPRISING BATTERY ARRANGEMENTS;

U.S. patent application Ser. No. 16/112,109, entitled SURGICAL INSTRUMENT SYSTEMS COMPRISING HANDLE ARRANGEMENTS;

U.S. patent application Ser. No. 16/112,114, entitled SURGICAL INSTRUMENT SYSTEMS COMPRISING FEEDBACK MECHANISMS;

U.S. patent application Ser. No. 16/112,117, entitled SURGICAL INSTRUMENT SYSTEMS COMPRISING LOCKOUT MECHANISMS;

U.S. patent application Ser. No. 16/112,095, entitled SURGICAL INSTRUMENTS COMPRISING A LOCKABLE END EFFECTOR SOCKET;

U.S. patent application Ser. No. 16/112,121, entitled SURGICAL INSTRUMENTS COMPRISING A SHIFTING MECHANISM;

U.S. patent application Ser. No. 16/112,151, entitled SURGICAL INSTRUMENTS COMPRISING A SYSTEM FOR ARTICULATION AND ROTATION COMPENSATION;

U.S. patent application Ser. No. 16/112,154, entitled SURGICAL INSTRUMENTS COMPRISING A BIASED SHIFTING MECHANISM;

U.S. patent application Ser. No. 16/112,226, entitled SURGICAL INSTRUMENTS COMPRISING AN ARTICULATION DRIVE THAT PROVIDES FOR HIGH ARTICULATION ANGLES;

U.S. patent application Ser. No. 16/112,062, entitled SURGICAL DISSECTORS AND MANUFACTURING TECHNIQUES;

U.S. patent application Ser. No. 16/112,098, entitled SURGICAL DISSECTORS CONFIGURED TO APPLY MECHANICAL AND ELECTRICAL ENERGY;

U.S. patent application Ser. No. 16/112,237, entitled SURGICAL CLIP APPLIER CONFIGURED TO STORE CLIPS IN A STORED STATE;

U.S. patent application Ser. No. 16/112,245, entitled SURGICAL CLIP APPLIER COMPRISING AN EMPTY CLIP CARTRIDGE LOCKOUT;

U.S. patent application Ser. No. 16/112,249, entitled SURGICAL CLIP APPLIER COMPRISING AN AUTOMATIC CLIP FEEDING SYSTEM;

U.S. patent application Ser. No. 16/112,253, entitled SURGICAL CLIP APPLIER COMPRISING ADAPTIVE FIRING CONTROL; and U.S. patent application Ser. No. 16/112,257, entitled SURGICAL CLIP APPLIER COMPRISING ADAPTIVE CONTROL IN RESPONSE TO A STRAIN GAUGE CIRCUIT.

Applicant of the present application owns the following U.S. patent applications that were filed on Oct. 26, 2018 which are each herein incorporated by reference in their respective entireties:

U.S. patent application Ser. No. 16/172,130, entitled CLIP APPLIER COMPRISING INTERCHANGEABLE CLIP RELOADS;

U.S. patent application Ser. No. 16/172,066, entitled CLIP APPLIER COMPRISING A MOVABLE CLIP MAGAZINE;

U.S. patent application Ser. No. 16/172,078, entitled CLIP APPLIER COMPRISING A ROTATABLE CLIP MAGAZINE;

U.S. patent application Ser. No. 16/172,087, entitled CLIP APPLIER COMPRISING CLIP ADVANCING SYSTEMS;

U.S. patent application Ser. No. 16/172,094, entitled CLIP APPLIER COMPRISING A CLIP CRIMPING SYSTEM;

U.S. patent application Ser. No. 16/172,128, entitled CLIP APPLIER COMPRISING A RECIPROCATING CLIP ADVANCING MEMBER;

U.S. patent application Ser. No. 16/172,168, entitled CLIP APPLIER COMPRISING A MOTOR CONTROLLER;

U.S. patent application Ser. No. 16/172,164, entitled SURGICAL SYSTEM COMPRISING A SURGICAL TOOL AND A SURGICAL HUB; and U.S. patent application Ser. No. 16/172,303, entitled METHOD FOR OPERATING A POWERED ARTICULATING MULTI-CLIP APPLIER.

Applicant of the present application owns the following U.S. patent applications, filed on Dec. 4, 2018, the disclosure of each of which is herein incorporated by reference in its entirety:

U.S. patent application Ser. No. 16/209,385, titled METHOD OF HUB COMMUNICATION, PROCESSING, STORAGE AND DISPLAY;

U.S. patent application Ser. No. 16/209,395, titled METHOD OF HUB COMMUNICATION;

U.S. patent application Ser. No. 16/209,403, titled METHOD OF CLOUD BASED DATA ANALYTICS FOR USE WITH THE HUB;

U.S. patent application Ser. No. 16/209,407, titled METHOD OF ROBOTIC HUB COMMUNICATION, DETECTION, AND CONTROL;

U.S. patent application Ser. No. 16/209,416, titled METHOD OF HUB COMMUNICATION, PROCESSING, DISPLAY, AND CLOUD ANALYTICS;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB;

U.S. patent application Ser. No. 16/209,447, titled METHOD FOR SMOKE EVACUATION FOR SURGICAL HUB;

U.S. patent application Ser. No. 16/209,453, titled METHOD FOR CONTROLLING SMART ENERGY DEVICES;

U.S. patent application Ser. No. 16/209,458, titled METHOD FOR SMART ENERGY DEVICE INFRASTRUCTURE;

U.S. patent application Ser. No. 16/209,465, titled METHOD FOR ADAPTIVE CONTROL SCHEMES FOR SURGICAL NETWORK CONTROL AND INTERACTION;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE;

U.S. patent application Ser. No. 16/209,490, titled METHOD FOR FACILITY DATA COLLECTION AND INTERPRETATION; and U.S. patent application Ser. No. 16/209,491, titled METHOD FOR CIRCULAR STAPLER CONTROL ALGORITHM ADJUSTMENT BASED ON SITUATIONAL AWARENESS.

Before explaining various aspects of surgical devices and systems in detail, it should be noted that the illustrative examples are not limited in application or use to the details of construction and arrangement of parts illustrated in the accompanying drawings and description. The illustrative examples may be implemented or incorporated in other aspects, variations, and modifications and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various surgical systems and instruments (e.g. surgical stapling instrument, surgical clip applier, surgical suturing instrument) are described in connection with the present disclosure. The surgical systems and/or instruments comprise a radio-frequency identification (RFID) system that includes one or more RFID scanners and one or more RFID tags, as will be discussed in greater detail below. Examples of surgical systems which use RFID technology are disclosed in U.S. Pat. No. 7,959,050 and U.S. Patent Application No. 2015/0053743, both of which are incorporated by reference herein in their entireties.

Radio-frequency identification (RFID) is used in a variety of industries to track and identify objects. RFID relies on radio waves to transfer digitally-stored information from a RFID tag to a RFID reader or receiver configured to receive the information. RFID technology uses RFID tags, sometimes referred to as chips, which contain electronically-stored information, and RFID readers, which serve to identify and communicate with the RFID tags. There are two different types of RFID systems—active RFID systems and passive RFID systems. Active RFID systems include RFID tags that comprise an on-board power source to broadcast their signals. Active RFID tags can include a battery within the RFID tag which allows the active RFID tag to function independently from the RFID reader. As such, RFID tags in an active RFID system do not need to wait to receive a signal from a RFID reader before sending out information. Instead, the active RFID tags are free to continuously send out a signal, or beacon. Many commercially available active RFID systems often operate at one of two main frequency ranges—433 MHz and 915 MHz, but any suitable frequency range can be used. Typically, a RFID tag must be within a specific distance or frequency range in order to be identified by its corresponding RFID reader.

Passive RFID systems include RFID tags which do not comprise an on-board power source but instead receive the energy needed to operate from an RFID reader. Contrary to active RFID tags, RFID tags in a passive RFID system do not actively send out a signal before receiving a prompt. Instead, passive RFID tags wait to receive information from a RFID reader before sending out a signal. Many commercially-available passive RFID systems often operate within three frequency ranges—Low Frequency ("LF"), High Frequency ("HF") & Near-Field Communication ("NFC"), and Ultra High Frequency ("UHF"). The LF bandwidth is 125-134 KHz and includes a longer wavelength with a short read range of approximately one to ten centimeters. The HF and NFC bandwidth is 13.56 MHz and includes a medium wavelength with a typical read range of one centimeter to one meter. The UHF bandwidth is 865-960 MHz and includes a short, high-energy wavelength of one meter which translates into a long read range. The above being said, any suitable frequency can be used.

A variety of RFID systems comprising differently-sized RFID tags exist. However, some are better suited for use in technology areas that require the tracking of very small objects. For example, Hitachi Chemical Co. Ltd. is a leading manufacturer in the RFID technology field. The Ultra Small size UHF RFID tag manufactured by Hitachi Chemical Co. Ltd. is typically no larger than 1.0 to 13 mm and enables communication between a RFID tag and a RFID reader at distances of several centimeters or more. Due to its compact nature, the Hitachi RFID tag is suitable for very small products which need to be identified. Each Hitachi RFID tag comprises an antenna, an IC chip connected to the antenna, and a sealing material that seals the IC chip and the antenna. Because the Hitachi RFID tag incorporates an antenna and an IC chip in a single unit, the Hitachi RFID tag is convenient enough to easily affix to any small object using an adhesive or tape, for example.

The Hitachi RFID tag comprises a square stainless steel plate and a metal antenna. The antenna comprises a LC resonant circuit or any other suitable circuit and is electrically connected to the plate. After the plate and the antenna are connected to one another, the antenna and plate are sealed together in a single unit with a sealing material. The sealing material is primarily composed of epoxy, carbon, and silica to enhance the heat resistance capabilities of the Hitachi RFID tag. That is, the heat resistance of the RFID tag substantially depends on the heat resistance capabilities of the sealing material. The sealing material has a high heat resistance withstanding temperatures of up to 250 to 300° C. for shorter time periods, such as a few seconds, and is resistant to heat for longer periods of time up to 150° C. Accordingly, the Hitachi RFID tag has a higher heat resistance than conventional RFID tags and can still operate normally even at high temperatures. Additional information regarding the Hitachi RFID tag can be found in U.S. Pat. No. 9,171,244, which is incorporated by reference herein in its entirety.

Surgical Hubs

Referring to FIG. 1, in various aspects, the RFID systems of the present disclosure can be utilized in conjunction with a computer-implemented interactive surgical system 11100 that includes one or more surgical systems 11102 and a cloud-based system (e.g., the cloud 11104 that may include a remote server 11113 coupled to a storage device 105). Each surgical system 11102 includes at least one surgical hub 11106 in communication with the cloud 11104 that may include a remote server 11113. In one example, as illustrated in FIG. 1, the surgical system 11102 includes a visualization system 11108, a robotic system 11110, and a handheld intelligent surgical instrument 11112, which are configured to communicate with one another and/or the hub 11106. In some aspects, a surgical system 11102 may include an M number of hubs 11106, an N number of visualization systems 11108, an O number of robotic systems 11110, and a P number of handheld intelligent surgical instruments 11112, where M, N, O, and P are integers greater than or equal to one.

Figure 2:
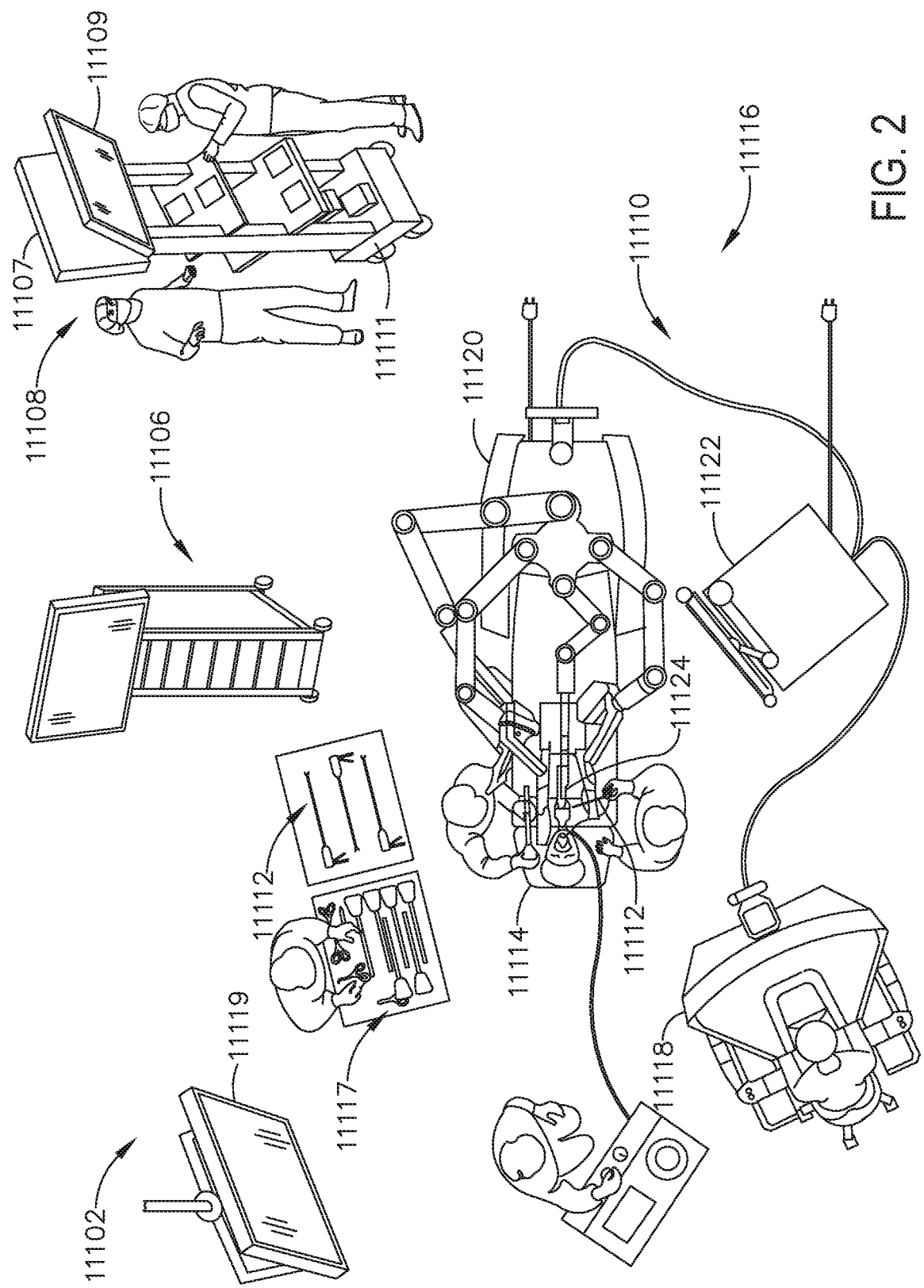
FIG. 2 is a surgical system being used to perform a surgical procedure in an operating room, in accordance with at least one aspect of the present disclosure.

FIG. 2 depicts an example of a surgical system 11102 being used to perform a surgical procedure on a patient who is lying down on an operating table 11114 in a surgical operating room 11116. A robotic system 11110 is used in the surgical procedure as a part of the surgical system 11102. The robotic system 11110 includes a surgeon's console 11118, a patient side cart 11120 (surgical robot), and a surgical robotic hub 11122. The patient side cart 11120 can manipulate at least one removably coupled surgical tool 11117 through a minimally invasive incision in the body of the patient while the surgeon views the surgical site through the surgeon's console 11118. An image of the surgical site can be obtained by a medical imaging device 11124, which can be manipulated by the patient side cart 11120 to orient the imaging device 11124. The robotic hub 11122 can be used to process the images of the surgical site for subsequent display to the surgeon through the surgeon's console 11118.

Other types of robotic systems can be readily adapted for use with the surgical system 11102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 11104 and are suitable for use with the present disclosure are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 11124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 11124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in the air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 11124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 11124 and its attachments and components. It will be appreciated that the sterile field may be considered a specified area, such as within a tray or on a sterile towel, that is considered free of microorganisms, or the sterile field may be considered an area, immediately around a patient, that has been prepared for a surgical procedure. The sterile field may include the scrubbed team members, who are properly attired, and all furniture and fixtures in the area.

In various aspects, the visualization system 11108 includes one or more imaging sensors, one or more image-processing units, one or more storage arrays, and one or more displays that are strategically arranged with respect to the sterile field, as illustrated in FIG. 2. In one aspect, the visualization system 11108 includes an interface for HL7, PACS, and EMR. Various components of the visualization system 11108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 11119 is positioned in the sterile field to be visible to an operator at the operating table 11114. In addition, a visualization tower 11111 is positioned outside the sterile field. The visualization tower 11111 includes a first non-sterile display 11107 and a second non-sterile display 11109, which face away from each other. The visualization system 11108, guided by the hub 11106, is configured to utilize the displays 11107, 11109, and 11119 to coordinate information flow to operators inside and outside the sterile field. For example, the hub 11106 may cause the visualization system 11108 to display a snapshot of a surgical site, as recorded by an imaging device 11124, on a non-sterile display 11107 or 11109, while maintaining a live feed of the surgical site on the primary display 11119. The snapshot on the non-sterile display 11107 or 11109 can permit a non-sterile operator to perform a diagnostic step relevant to the surgical procedure, for example.

In one aspect, the hub 11106 is also configured to route a diagnostic input or feedback entered by a non-sterile operator at the visualization tower 11111 to the primary display 11119 within the sterile field, where it can be viewed by a sterile operator at the operating table. In one example, the input can be in the form of a modification to the snapshot displayed on the non-sterile display 11107 or 11109, which can be routed to the primary display 11119 by the hub 11106.

Referring to FIG. 2, a surgical instrument 11112 is being used in the surgical procedure as part of the surgical system 11102. The hub 11106 is also configured to coordinate information flow to a display of the surgical instrument 11112. For example, coordinate information flow is further described in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 11111 can be routed by the hub 11106 to the surgical instrument display 11237 (FIG. 5) within the sterile field, where it can be viewed by the operator of the surgical instrument 11112. Example surgical instruments that are suitable for use with the surgical system 11102 are described under the heading "Surgical Instrument Hardware" in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
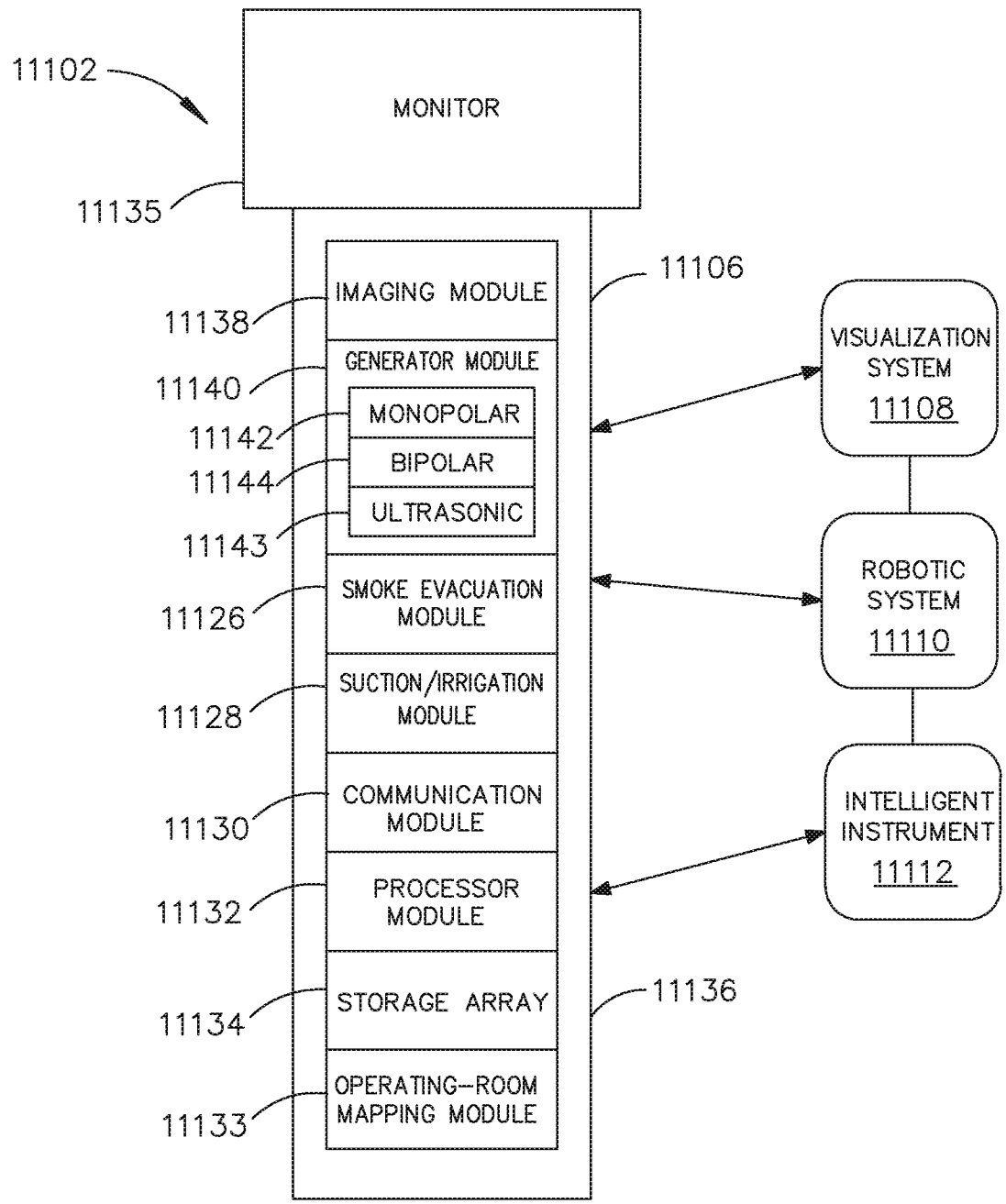
FIG. 3 is a surgical hub paired with a visualization system, a robotic system, and an intelligent instrument, in accordance with at least one aspect of the present disclosure.

Referring now to FIG. 3, a hub 11106 is depicted in communication with a visualization system 11108, a robotic system 11110, and a handheld intelligent surgical instrument 11112. The hub 11106 includes a hub display 11135, an imaging module 11138, a generator module 11140 (which can include a monopolar generator 11142, a bipolar generator 11144, and/or an ultrasonic generator 11143), a communication module 11130, a processor module 11132, and a storage array 11134. In certain aspects, as illustrated in FIG. 3, the hub 11106 further includes a smoke evacuation module 11126, a suction/irrigation module 11128, and/or an operating room mapping module 11133.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure.

Valuable time can be lost addressing this issue during a surgical procedure. Detangling the lines may necessitate disconnecting the lines from their respective modules, which may require resetting the modules. The hub modular enclosure 11136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 11136 is configured to accommodate different generators and facilitate an interactive communication therebetween. One of the advantages of the hub modular enclosure 11136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 4:
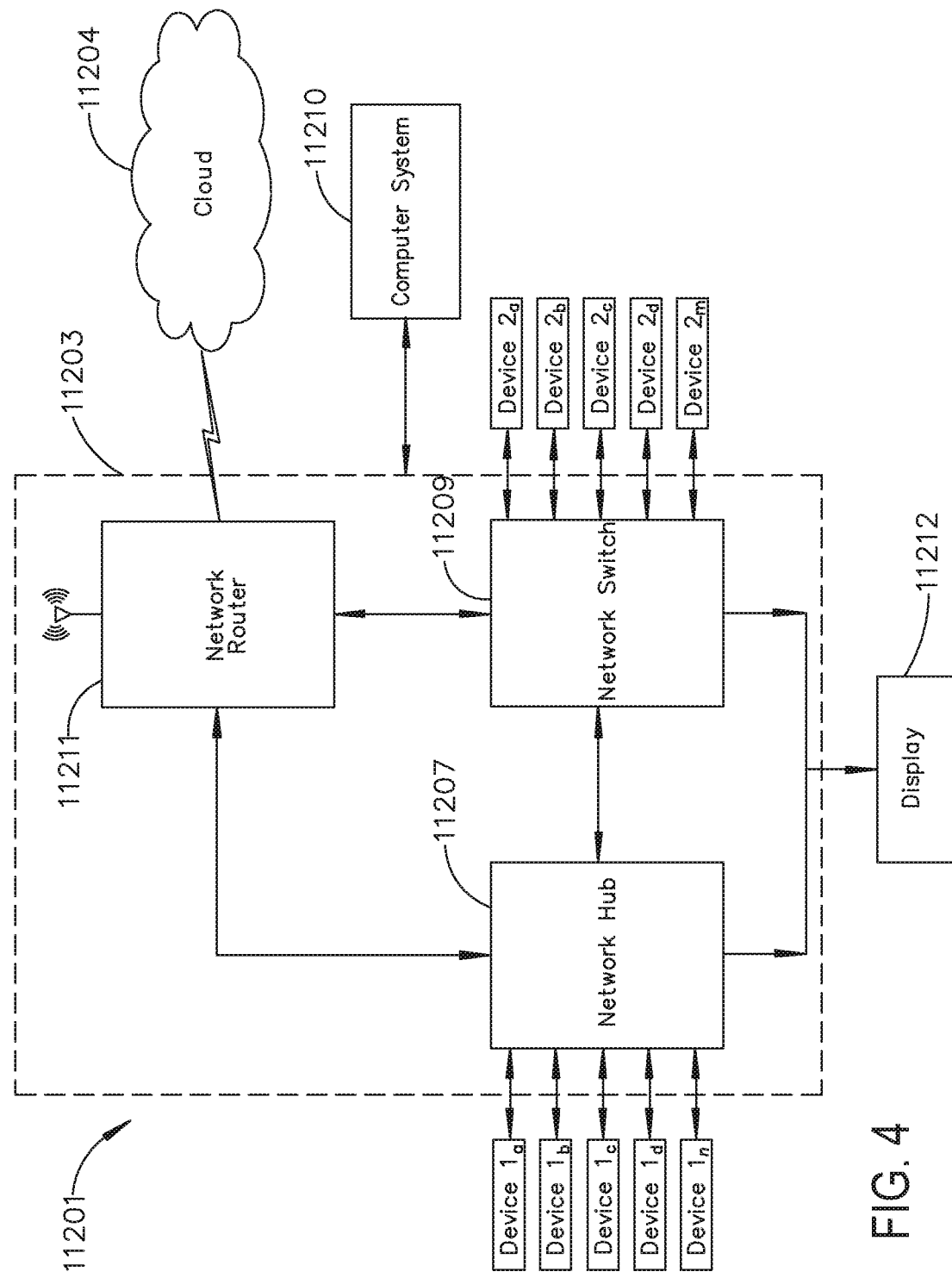
FIG. 4 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.
Figure 5:
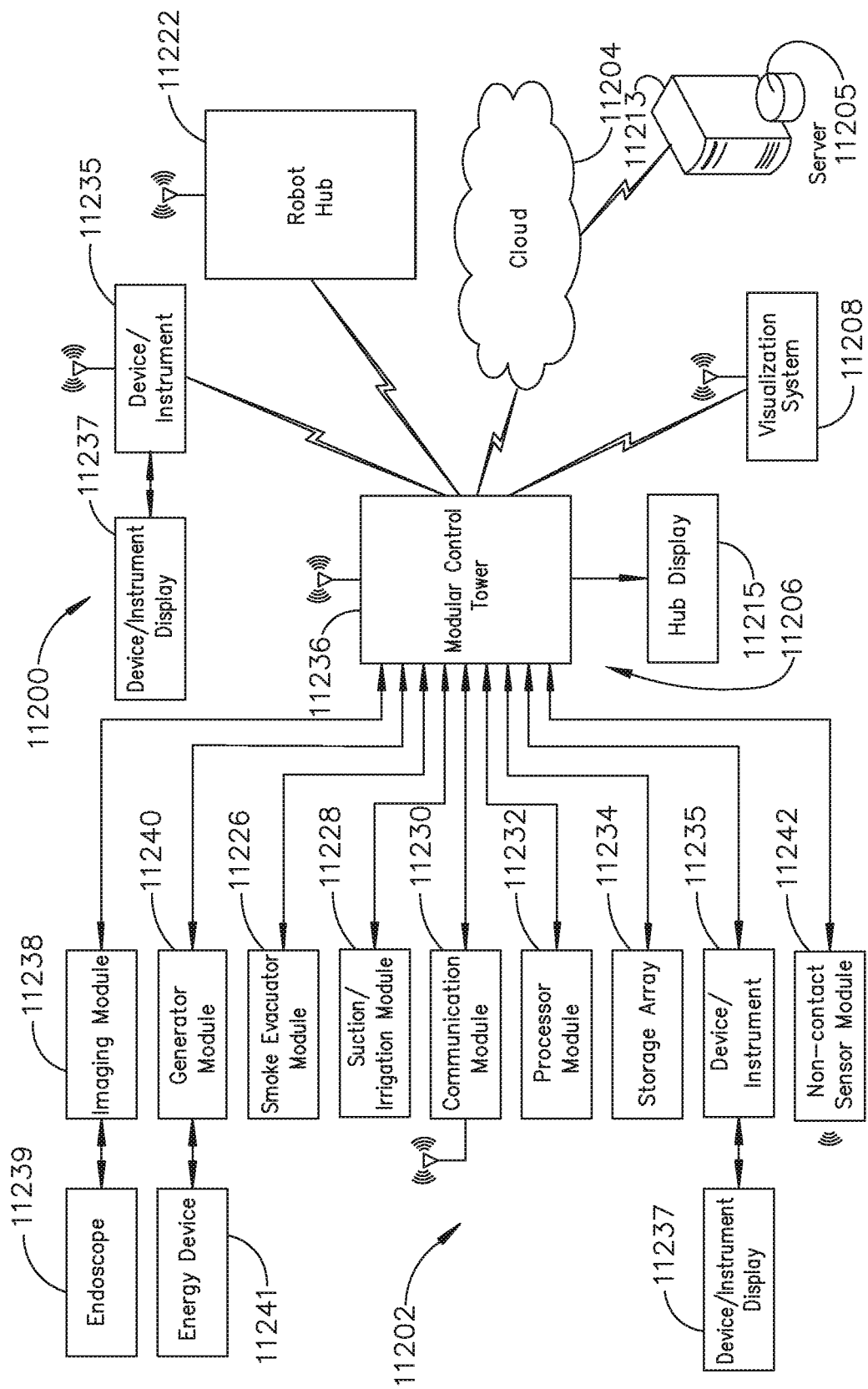
FIG. 5 illustrates a computer-implemented interactive surgical system, in accordance with at least one aspect of the present disclosure.

FIG. 4 illustrates a surgical data network 11201 comprising a modular communication hub 11203 configured to connect modular devices located in one or more operating theaters of a healthcare facility, or any room in a healthcare facility specially equipped for surgical operations, to a cloud-based system (e.g., the cloud 11204 that may include a remote server 11213 coupled to a storage device 11205, as shown in FIG. 5). In one aspect, the modular communication hub 11203 comprises a network hub 11207 and/or a network switch 11209 in communication with a network router. The modular communication hub 11203 also can be coupled to a local computer system 11210 to provide local computer processing and data manipulation. The surgical data network 11201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 11207 or network switch 11209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 11203. The network hub 11207 and/or the network switch 11209 may be coupled to a network router 11211 to connect the devices 1a-1n to the cloud 11204 or the local computer system 11210. Data associated with the devices 1a-1n may be transferred to cloud-based computers via the router for remote data processing and manipulation. Data associated with the devices 1a-1n may also be transferred to the local computer system 11210 for local data processing and manipulation. Modular devices 2a-2m located in the same operating theater also may be coupled to a network switch 11209. The network switch 11209 may be coupled to the network hub 11207 and/or the network router 11211 to connect to the devices 2a-2m to the cloud 11204. Data associated with the devices 2a-2n may be transferred to the cloud 11204 via the network router 11211 for data processing and manipulation. Data associated with the devices 2a-2m may also be transferred to the local computer system 11210 for local data processing and manipulation.

It will be appreciated that the surgical data network 11201 may be expanded by interconnecting multiple network hubs 11207 and/or multiple network switches 11209 with multiple network routers 11211. The modular communication hub 11203 may be contained in a modular control tower configured to receive multiple devices 1a-1n/2a-2m. The local computer system 11210 also may be contained in a modular control tower. The modular communication hub 11203 is connected to a display 11212 to display images obtained by some of the devices 1a-1n/2a-2m, for example, during surgical procedures. In various aspects, the devices 1a-1n/2a-2m may include, for example, various modules, such as an imaging module 11138 coupled to an endoscope, a generator module 11140 coupled to an energy-based surgical device, a smoke evacuation module 11126, a suction/irrigation module 11128, a communication module 11130, a processor module 11132, a storage array 11134, a surgical device coupled to a display, and/or a non-contact sensor module, among other modular devices that may be connected to the modular communication hub 11203 of the surgical data network 11201.

In one aspect, the surgical data network 11201 may comprise a combination of network hub(s), network switch (es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 11203 and/or computer system 11210 located in the surgical theater (e.g., a fixed, mobile, temporary, or field operating room or space) and to devices connected to the modular communication hub 11203 and/or computer system 11210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data, including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques, such as overlaying images captured by multiple imaging devices. The data gathered by the devices 1a-1n/2a-2m, including image data, may be transferred to the cloud 11204 or the local computer system 11210 or both for data processing and manipulation, including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 11203 over a wired channel or a wireless channel depending on the configuration of the devices 1a-1n to a network hub. The network hub 11207 may be implemented, in one aspect, as a local network broadcast device that works on the physical layer of the Open System Interconnection (OSI) model. The network hub provides connectivity to the devices 1a-1n located in the same operating theater network. The network hub 11207 collects data in the form of packets and sends them to the router in half-duplex mode. The network hub 11207 does not store any media access control/Internet Protocol (MAC/IP) to transfer the device data. Only one of the devices 1a-1n can send data at a time through the network hub 11207. The network hub 11207 has no routing tables or intelligence regarding where to send information and broadcasts all network data across each connection and to a remote server 11213 (FIG. 5) over the cloud 11204. The network hub 11207 can detect basic network errors, such as collisions, but having all information broadcast to multiple ports can be a security risk and cause bottlenecks.

In another implementation, the operating theater devices 2a-2m may be connected to a network switch 11209 over a wired channel or a wireless channel. The network switch 11209 works in the data link layer of the OSI model. The network switch 11209 is a multicast device for connecting the devices 2a-2m located in the same operating theater to the network. The network switch 11209 sends data in the form of frames to the network router 11211 and works in full duplex mode. Multiple devices 2a-2m can send data at the same time through the network switch 11209. The network switch 11209 stores and uses MAC addresses of the devices 2a-2m to transfer data.

The network hub 11207 and/or the network switch 11209 are coupled to the network router 11211 for connection to the cloud 11204. The network router 11211 works in the network layer of the OSI model. The network router 11211 creates a route for transmitting data packets received from the network hub 11207 and/or network switch 11209 to cloud-based computer resources for further processing and manipulation of the data collected by any one of or all the devices 1a-1n/2a-2m. The network router 11211 may be employed to connect two or more different networks located in different locations, such as, for example, different operating theaters of the same healthcare facility or different networks located in different operating theaters of different healthcare facilities. The network router 11211 sends data in the form of packets to the cloud 11204 and works in full duplex mode. Multiple devices can send data at the same time. The network router 11211 uses IP addresses to transfer data.

In one example, the network hub 11207 may be implemented as a USB hub, which allows multiple USB devices to be connected to a host computer. The USB hub may expand a single USB port into several tiers so that there are more ports available to connect devices to the host system computer. The network hub 11207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 11203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 11203 via a number of wireless or wired communication standards or protocols, including, but not limited to, Wi-Fi (IEEE 802.11 family), WMAX (IEEE 802.16 family), IEEE 802.20, long-term evolution (LTE), Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 11203 may serve as a central connection for one or all of the operating theater devices 1a-1n/2a-2m and handles a data type known as frames. Frames carry the data generated by the devices 1a-1n/2a-2m. When a frame is received by the modular communication hub 11203, it is amplified and transmitted to the network router 11211, which transfers the data to the cloud computing resources by using a number of wireless or wired communication standards or protocols, as described herein.

The modular communication hub 11203 can be used as a standalone device or be connected to compatible network hubs and network switches to form a larger network. The modular communication hub 11203 is generally easy to install, configure, and maintain, making it a good option for networking the operating theater devices 1a-1n/2a-2m.

Figure 6:
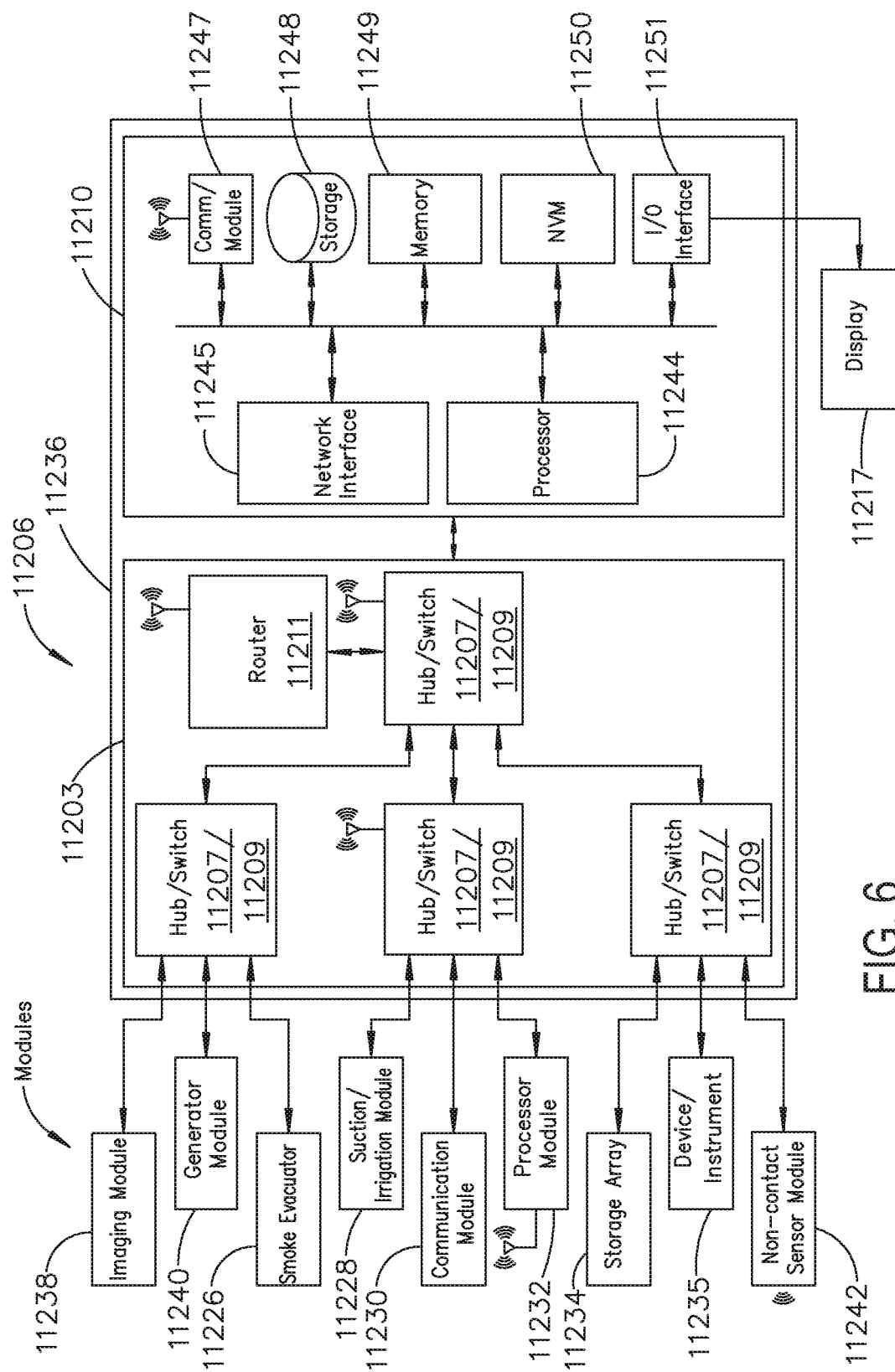
FIG. 6 illustrates a surgical hub comprising a plurality of modules coupled to the modular control tower, in accordance with at least one aspect of the present disclosure.

FIG. 5 illustrates a computer-implemented interactive surgical system 11200. The computer-implemented interactive surgical system 11200 is similar in many respects to the computer-implemented interactive surgical system 11100. For example, the computer-implemented interactive surgical system 11200 includes one or more surgical systems 11202, which are similar in many respects to the surgical systems 11102. Each surgical system 11202 includes at least one surgical hub 11206 in communication with a cloud 11204 that may include a remote server 11213. In one aspect, the computer-implemented interactive surgical system 11200 comprises a modular control tower 11236 connected to multiple operating theater devices such as, for example, intelligent surgical instruments, robots, and other computerized devices located in the operating theater. As shown in FIG. 6, the modular control tower 11236 comprises a modular communication hub 11203 coupled to a computer system 11210. As illustrated in the example of FIG. 5, the modular control tower 11236 is coupled to an imaging module 11238 that is coupled to an endoscope 11239, a generator module 11240 that is coupled to an energy device 11241, a smoke evacuator module 11226, a suction/irrigation module 11228, a communication module 11230, a processor module 11232, a storage array 11234, a smart device/instrument 11235 optionally coupled to a display 11237, and a non-contact sensor module 11242. The operating theater devices are coupled to cloud computing resources and data storage via the modular control tower 11236. A robot hub 11222 also may be connected to the modular control tower 11236 and to the cloud computing resources. The devices/instruments 11235 and visualization systems 11208, among others, may be coupled to the modular control tower 11236 via wired or wireless communication standards or protocols, as described herein. The modular control tower 11236 may be coupled to a hub display 11215 (e.g., monitor, screen) to display and overlay images received from the imaging module, device/instrument display, and/or other visualization systems 11208. The hub display also may display data received from devices connected to the modular control tower in conjunction with images and overlaid images.

FIG. 6 illustrates a surgical hub 11206 comprising a plurality of modules coupled to the modular control tower 11236. The modular control tower 11236 comprises a modular communication hub 11203, e.g., a network connectivity device, and a computer system 11210 to provide local processing, visualization, and imaging, for example. As shown in FIG. 6, the modular communication hub 11203 may be connected in a tiered configuration to expand the number of modules (e.g., devices) that may be connected to the modular communication hub 11203 and transfer data associated with the modules to the computer system 11210, cloud computing resources, or both. As shown in FIG. 6, each of the network hubs/switches in the modular communication hub 11203 includes three downstream ports and one upstream port. The upstream network hub/switch is connected to a processor to provide a communication connection to the cloud computing resources and a local display 11217. Communication to the cloud 11204 may be made either through a wired or a wireless communication channel.

The surgical hub 11206 employs a non-contact sensor module 11242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 11210 comprises a processor 11244 and a network interface 11245. The processor 11244 is coupled to a communication module 11247, storage 11248, memory 11249, non-volatile memory 11250, and input/output interface 11251 via a system bus. The system bus can be any of several types of bus structure(s), including the memory bus or memory controller, a peripheral bus or external bus, and/or a local bus using any variety of available bus architectures including, but not limited to, 9-bit bus, Industrial Standard Architecture (ISA), Micro-Charnel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 11244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random-access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 11244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 11210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 11210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 11210 through input device(s) coupled to the I/O interface 11251. The input devices include, but are not limited to, a pointing device such as a mouse, trackball, stylus, touch pad, keyboard, microphone, joystick, game pad, satellite dish, scanner, TV tuner card, digital camera, digital video camera, Web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 11210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5, and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 11210 of FIG. 6, the imaging module 11238 and/or visualization system 11208, and/or the processor module 11232 of FIGS. 5-6, may comprise an image processor, image-processing engine, media processor, or any specialized digital signal processor (DSP) used for the processing of digital images. The image processor may employ parallel computing with single instruction; multiple data (SIMD); or multiple instruction, multiple data (MIMD) technologies to increase speed and efficiency. The digital image-processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 11210. The hardware/software necessary for connection to the network interface includes, for illustrative purposes only, internal and external technologies such as modems, including regular telephone-grade modems, cable modems, DSL modems, ISDN adapters, and Ethernet cards.

RFID Detection Assemblies

During various surgical procedures, a surgical instrument comprising at least one replaceable component are used. It is important that such replaceable components be replaced with functional and/or compatible components. Various identification systems described in greater detail herein verify, among other things, a component's compatibility with the surgical instrument and/or verify an operating status of the component. For instance, a controller and/or an identification system can serve to, for example, ensure that the packaging containing the replaceable component has not been destroyed and/or tampered with, alert a clinician if a component is compatible or incompatible with the surgical instrument, alert the clinician if the replaceable component is expired, and/or alert the clinician if a recall exists for a particular manufacturing batch and/or type of the replaceable component.

The identification systems described herein can either be active systems or passive systems. In various embodiments, a combination of active and passive identification systems are used. Passive systems can include, for example, a barcode, a quick response (QR) code, and/or a radio frequency identification (RFID) tag. Passive systems do not comprise an internal power source, and the passive systems described herein require a reader and/or scanner to send a first signal, such as an interrogation signal, for example.

Passive radio frequency identification (RFID) systems communicate information by using radio frequencies. Such passive RFID systems comprise an RFID scanner and an RFID tag with no internal power source. The RFID tag is powered by electromagnetic energy transmitted from the RFID scanner. Each RFID tag comprises a chip, such as a microchip, for example, that stores information about the replaceable component and/or a surgical instrument with which the replaceable component is compatible. While the chip may only contain an identification number, in various instances, the chip can store additional information such as, for example, the manufacturing data, shipping data, and/or maintenance history. Each RFID tag comprises a radio antenna that allows the RFID tag to communicate with the RFID scanner. The radio antenna extends the range in which the RFID tag can receive signals from the RFID scanner and transmit response signals back to the RFID scanner. In a passive RFID system, the RFID scanner, which also comprises its own antenna, transmits radio signals that activate RFID tags that are positioned within a pre-determined range. The RFID scanner is configured to receive the response signals that are "bounced back" from RFID tags, allowing the RFID scanner is to capture the identification information representative of the replaceable component. In various instances, the one or more response signals comprise the same signal as the interrogation signal. In various instances, the one or more response signals comprise a modified signal from the interrogation signal. In various instances, the RFID scanner is also able to write, or encode, information directly onto the RFID tag. In any event, the RFID scanner is able to pass information about the replaceable component to a controller, such as the control system of a surgical instrument and/or a remote surgical system or hub. The RFID scanner is configured to read multiple RFID tags at once, as the RFID tags are activated by radio signals. Additionally, in certain instances, the RFID scanner is able to update, or rewrite, information stored on an RFID tag in signal range with the RFID scanner. The updates can, for example, be transmitted to the RFID scanner from a surgical hub (e.g. 11106, 8001), or any suitable server 11113 (FIG. 1). Various surgical hubs are described in described in U.S. patent application Ser. No. 16/209,395, titled METHOD OF HUB COMMUNICATION, and filed Dec. 4, 2018, which is hereby incorporated by reference in its entirety.

Active radio frequency identification (RFID) systems also comprise an RFID tag and an RFID scanner. However, the RFID tag in an active RFID system comprises an internal power source. Active RFID systems utilize battery-powered RFID tags that are configured to continuously broadcast their own signal. One type of active RFID tag is commonly referred to as a "beacon." Such beacon RFID tags do not wait to receive a first signal from an RFID scanner. Instead, the beacon RFID tag continuously transmits its stored information. For example, the beacon can send out its information at an interval of every 3-5 seconds. Another type of active RFID tag comprises a transponder. In such systems, the RFID scanner transmits a signal first. The RFID transponder tag then sends a signal back to the RFID scanner with the relevant information. Such RFID transponder tag systems are efficient, as they conserve battery life when, for example, the RFID tag is out of range of the RFID scanner. In various instances, the active RFID tag comprises an on-board sensor to track an environmental parameter. For example, the on-board sensor can track moisture levels, temperature, and/or other data that might be relevant.

In various aspects, the RFID systems of the present disclosure can be disposed on or otherwise associated with surgical instruments 11112 (FIGS. 1-3), components of surgical instruments 11112, consumables useable in conjunction with surgical instruments 11112, and/or other systems or devices associated with a surgical system 11100 (FIGS. 1-3), such as a visualization system 11108 (FIGS. 1-3), a robotic system 11110 (FIGS. 1-3), a hub 11106 (FIGS. 1-3), or components thereof. Further, the RFID tags described in greater detail below, can be utilized to store a datum or data identifying the device or component of the surgical system 11100 that the RFID tag is associated with. In addition, corresponding RFID scanners can be configured to read the RFID tags as the components of the surgical system 11100 are utilized in order to identify the components, devices, and/or systems that are in use in the operating theater and then control a surgical instrument 11112, hub 11106, visualization system 11108, or another component, device, and/or system accordingly.

In various examples, an RFID scanner can be positioned within or on a surgical instrument 11112 such that the RFID scanner can read RFID tags of components (e.g., batteries, shafts, or cartridges) as the surgical instrument 11112 is assembled. As another example, an RFID scanner could be associated with a surgical instrument 11112 such that the RFID scanner can read RFID tags associated with a hub 11106, visualization system 11108, and/or a robotic system 11110 as the surgical instrument 11112 is brought into proximity of or interacts with those systems. These and other RFID detection assemblies are described in greater detail below.

Further, various control systems for controlling the RFID systems, the surgical instruments associated therewith, and/or other devices or components of a surgical system 11100, are described herein. Example of such control systems include a control system 1211 (FIG. 7), a control system 8111 (FIG. 7A), and a processor module 11232 of a surgical hub 11206 (FIGS. 5 and 6). Such control systems can be directly integrated into the component or device that they are controlling. For example, the control system 1211 illustrated in FIG. 7 can control the surgical instrument 1100 (FIG. 8-10) into which it is integrated. In another example, the control system 8111 illustrated in FIG. 7A can control the surgical instrument 8002 (FIG. 11) into which it is integrated. Alternatively, such control systems can be communicably coupled to the component or device that they are controlling. For example, the processor module 11232 can be configured to control surgical instruments 11112 and/or other components or devices of a surgical system 11100 that are paired with or communicably coupled to the surgical hub 11206, as is described above. These control systems can include or be communicably coupled to RFID scanners for detecting RFID tags. The control systems can then control the subject devices according to the combination or arrangement of detected RFID tags.

Referring to FIGS. 7 and 8-10, the control system 1211 includes a control circuit 1210 that can be integrated with the RFID scanner 1202 or can be coupled to, but positioned separately from, the RFID scanner 1202, for example. The control circuit 1210 can be configured to receive input from the RFID scanner 1202 indicative of the information about a staple cartridge 1320 stored in the RFID tag 1203 and/or information about the anvil 1200 stored in the RFID tag 1201.

In various examples, the RFID tag 1203 stores identification information of the staple cartridge 1320 and the RFID tag 1201 stores identification information of the anvil 1200. In such examples, the control circuit 1210 receives input from the RFID scanner 1202 indicative of the identification information of the staple cartridge 1320 and verifies the identity of the staple cartridge 1320 based on the input. Further, the control circuit 1210 receives input from RFID scanner 1202 indicative of the identification information of the anvil 1200 and verifies the identity of the anvil 1200 based on the input.

In at least one example, the control circuit 1210 includes a microcontroller 1213 that has a processor 1214 and a storage medium such as, for example, a memory 1212. The memory 1212 stores program instructions for performing various processes such as, for example, identity verification. The program instructions, when executed by the processor 1214, cause the processor 1214 to verify the identity of the staple cartridge 1320 and the anvil 1200 by comparing the identification information received from the RFID tags 1201, 1203 to identification information stored in the memory 1212 in the form of an identity database or table, for example.

In at least one example, the control circuit 1210 can be configured to check compatibility of the anvil 1200 with staple cartridge 1320 of the stapling head assembly 1300 based on input from the RFID scanner 1202. The processor 1214 can, for example, check the identity information of the anvil 1200 and the staple cartridge 1320 against a compatibility database or table stored in memory 1212.

Figure 8:
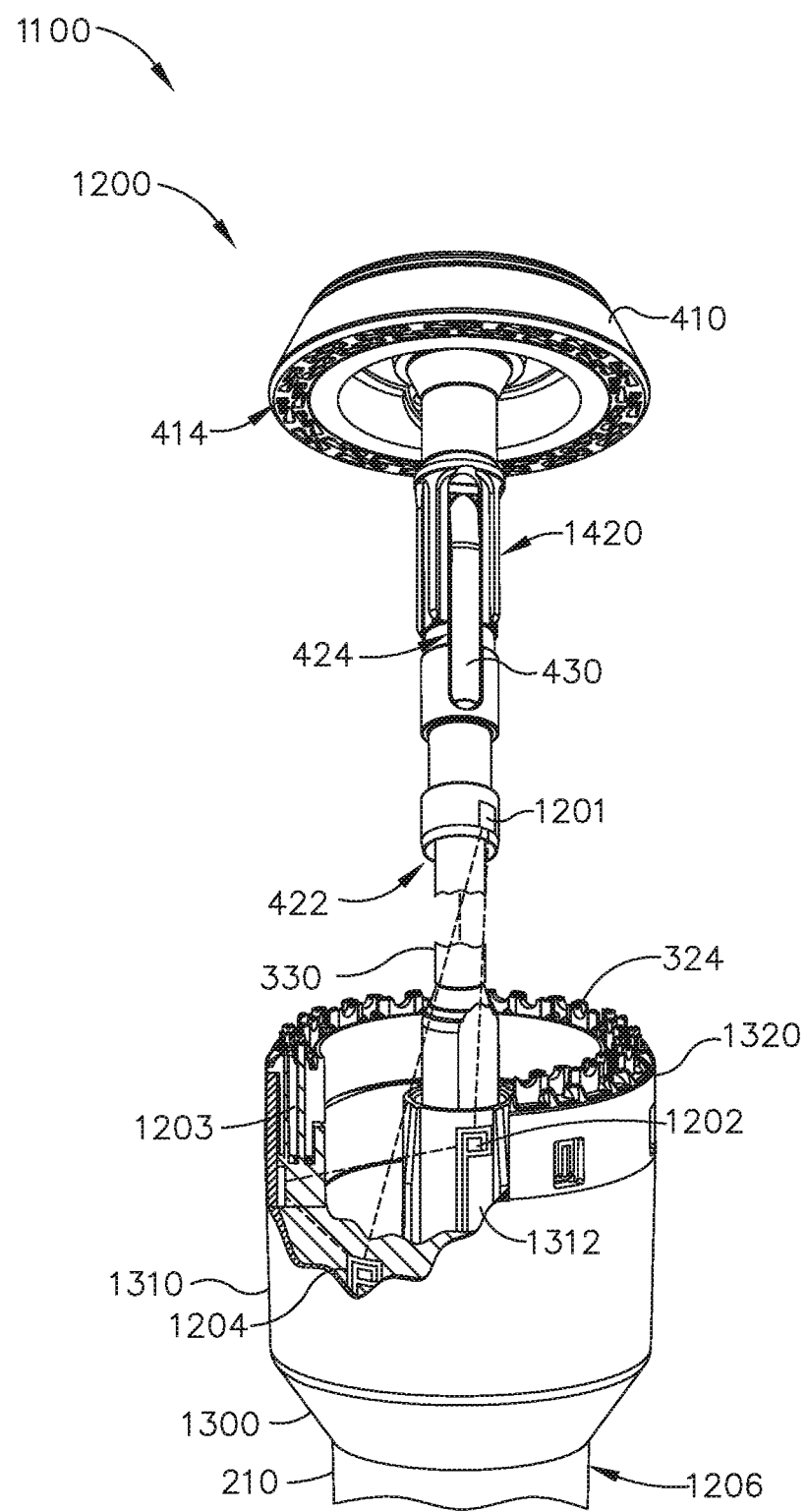
FIG. 8 depicts stapling head assembly and an anvil being coupled to a trocar of the stapling head assembly, in accordance with at least one aspect of the present disclosure.
Figure 9:
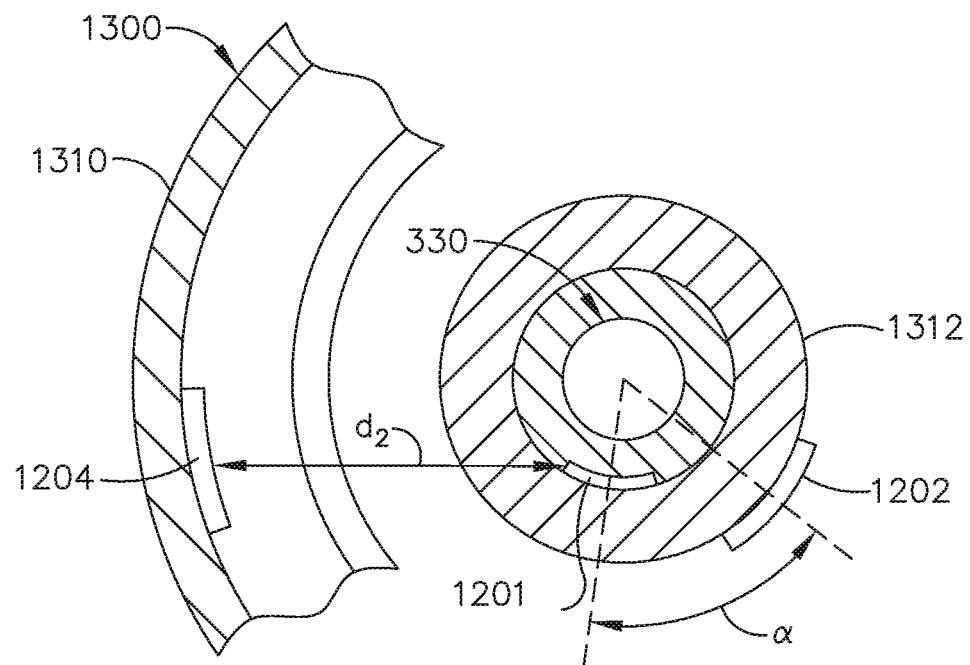
FIG. 9 depicts a partial transverse cross-sectional view of an anvil in an improper seating orientation with a stapling head assembly, in accordance with at least one aspect of the present disclosure.
Figure 10:
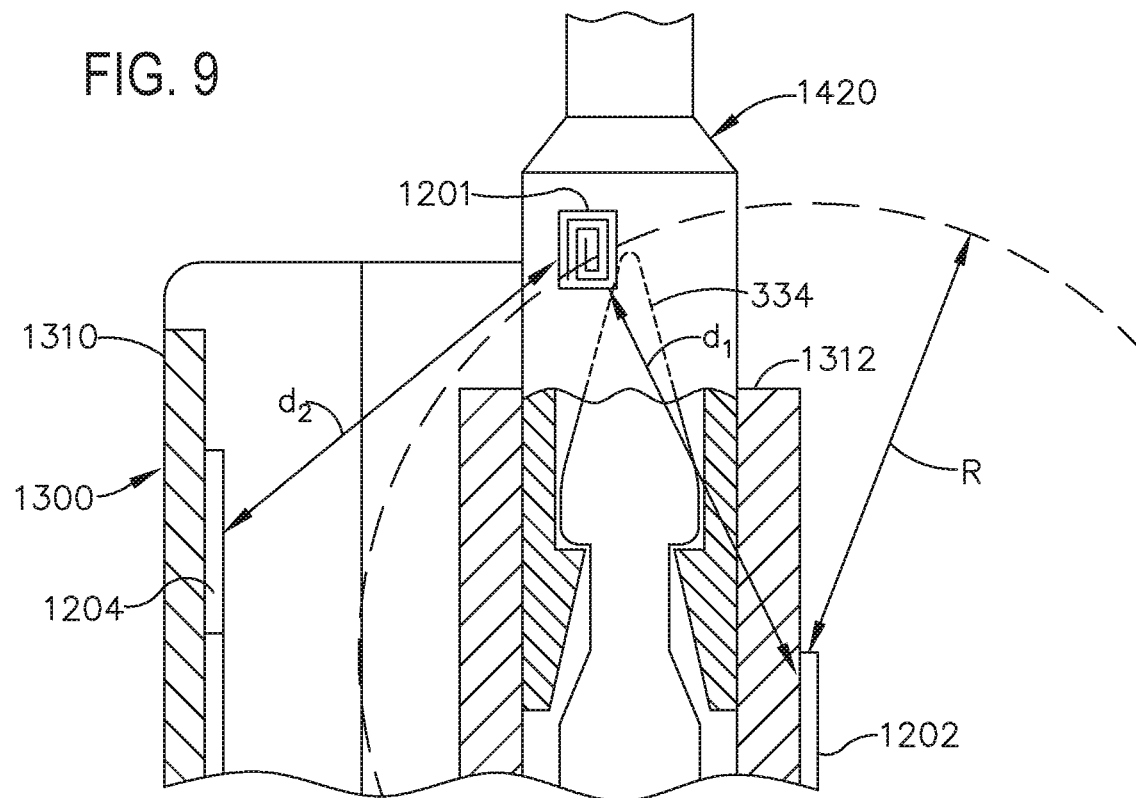
FIG. 10 depicts a partial longitudinal cross-sectional view of an anvil in an improper seating orientation with a stapling head assembly, in accordance with at least one aspect of the present disclosure.

In one aspect, an RFID scanner 1202 can be positioned within or otherwise associated with a surgical instrument to read a corresponding RFID tag 1201 that is configured to indicate the actions or operations performed by the surgical instrument. For example, FIGS. 8-10 illustrate one such configuration for a surgical instrument 1100 in the form of a circular stapler. A distinct issue with circular staplers is that their anvils are detachable from their stapling head assemblies, and must be separately introduced to a surgical site in different manners and from different access points. Accordingly, unlike other stapling instruments, circular staplers are at risk from anvil-staple head assembly mismatching and/or anvil-staple cartridge mismatching. Further, to be properly assembled or coupled an anvil and a stapling head assembly must be properly oriented with respect to each other at a specific orientation at the surgical site. Improper orientation of an anvil and a corresponding stapling head assembly, as illustrated in FIG. 9, can lead to a misalignment between the staple forming pockets 414 (FIG. 8) of the anvil and staple openings 324 (FIG. 8) of a staple cartridge 1320, which may lead to improper staple formation. In addition, the improper orientation of an anvil and a corresponding stapling head assembly can lead to improper seating of the anvil with respect to the stapling head assembly. An improperly seated, or partially seated, anvil may become unseated, or separated from the stapling head assembly, due to externally applied loads from the tissue captured between the anvil and the stapling head assembly during closure.

To address the issues above, the surgical instrument 1100 includes an anvil 1200 equipped with a radio-frequency identification (RFID) tag 1201 recognizable or detectable by an RFID scanner 1202 on a stapling head assembly 1300 of the surgical instrument. Likewise, the staple cartridge 1320 includes an RFID tag 1203 also recognizable or detectable by the RFID scanner 1202. The RFID tag 1201 stores information about the anvil 1200, and the RFID tag 1203 stores information about the staple cartridge 1320. As described below, the information can be checked and compared for authentication and/or compatibility.

Referring still to FIGS. 7 and 8-10, he anvil 1200 includes a head 410, staple forming pockets 414, and a shank 1420. In this example, the RFID tag 1201 is supported by the shank 1420, on an outer surface thereof, near a bore 422 defined by the shank 1420. The anvil 1200 is coupled or assembled with a stapling head assembly 1300 by advancing the anvil 1200 toward a trocar 330 of the stapling head assembly 1300 such that the trocar 330 is received through the bore 422, as illustrated in FIG. 8. In at least one example, the RFID tag 1201 is positioned on the shank 1420 at a first longitudinal position that corresponds, or substantially corresponds, to a second longitudinal position of a tip of the head 334 of the trocar 330 when the anvil 1200 is properly oriented and fully seated with respect to the stapling head assembly 1300. In other words, the tip of the head 334 of the trocar 330, when it is received in the shank 1420 at its final seating position, is transversely aligned, or at least substantially aligned, with the RFID tag 1201. In at least one example, the RFID tag 1201 is positioned on the shank 1420 at a position distal to the bore 422 and proximal to the lateral openings 424, which are formed through the sidewall of shank 1420, and/or proximal to latch members 430 of the shank 1420.

Referring to FIG. 8, the RFID scanner 1202 is located on an outer surface of a cylindrical inner core member 1312 that extends distally within a tubular casing 1310 of the stapling head assembly 1300. Tubular casing 1310 is fixedly secured to an outer sheath 210 of the shaft assembly 1206 of the surgical instrument, such that tubular casing 1310 serves as a mechanical ground for stapling head assembly 1300. The RFID scanner 1202 is supported by the inner core member 1312, on an outer surface thereof, near its distal end. In at least one example, a recess or pocket is defined in the inner core member 1312, and the RFID scanner 1202 is positioned in the recess or pocket. The RFID scanner 1202 can be held in place in the recess, or pocket, using any suitable technique such as, for example, friction fitting or biocompatible adhesive. Alternatively, the RFID scanner 1202 can be positioned on an inner surface of the cylindrical inner core member 1312. In the example of FIG. 8, the RFID scanner 1202 is located at a distal portion of the inner core member 1312 below the deck member of the staple cartridge 1320. In various example, the RFID tag 1201 and the RFID tag 1203 are insulated from the shank 1420 and the inner core member 1312 using any suitable insulative material.

In various examples, RFID tag 1201 and the RFID tag 1203 are recognizable or detectable by the RFID scanner 1202 in a closed configuration of the instrument where tissue is captured between the anvil 1200 and stapling head assembly 1300.

Additional details regarding the aspect illustrated in FIGS. 8-10 can be found in U.S. patent application Ser. No. 16/458,109, entitled MECHANISMS FOR PROPER ANVIL ATTACHMENT SURGICAL STAPLING HEAD ASSEMBLY, filed concurrently herewith on Jun. 30, 2019, now U.S. Patent Application Publication No. 2020/0405312, which is hereby incorporated by reference herein in its entirety.

Figure 7:
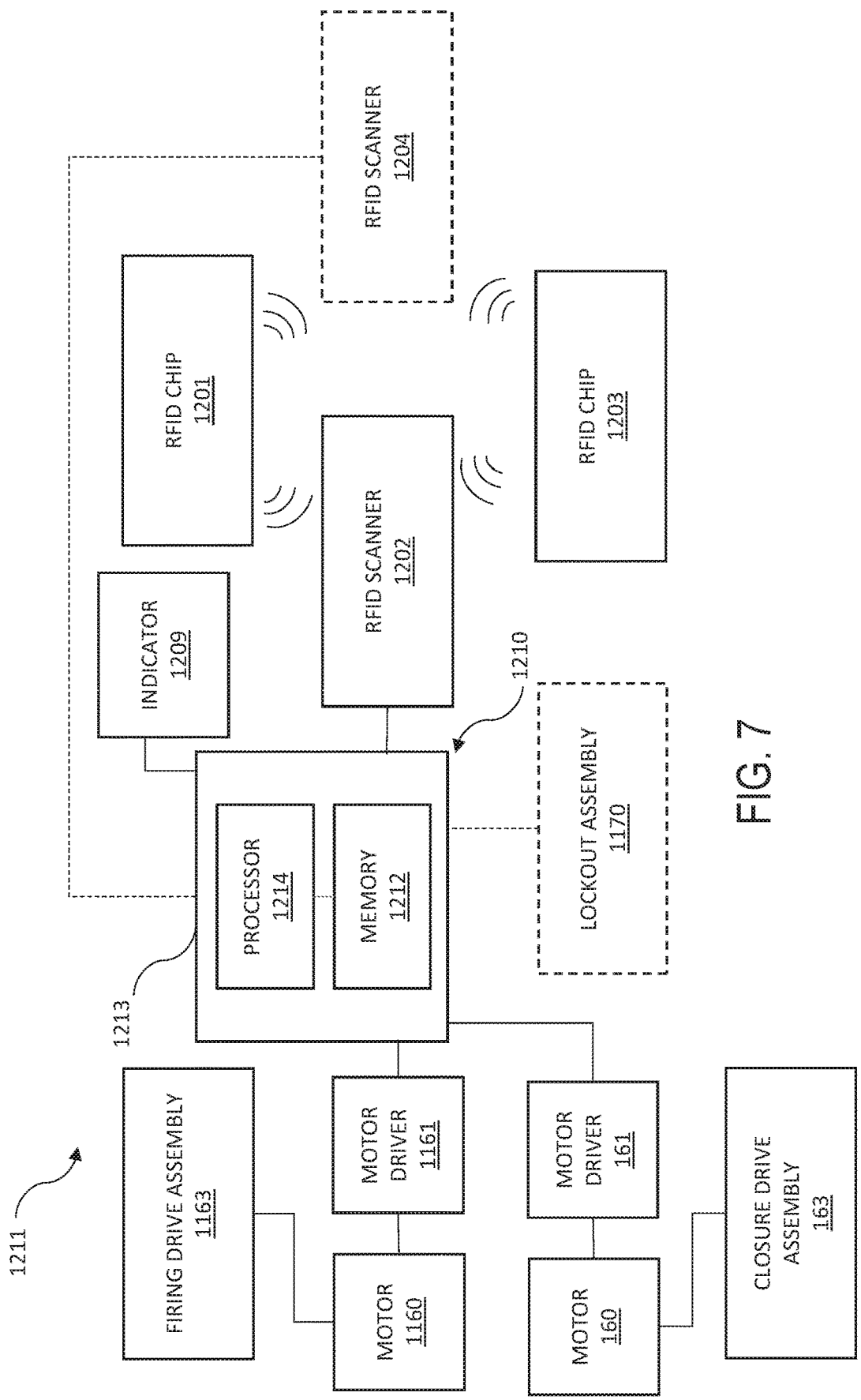
FIG. 7 depicts a control system of a surgical stapling instrument, in accordance with at least one aspect of the present disclosure.

FIG. 7A illustrates a block diagram of the control system 8111. Many of the components of the illustrated control system 8111 coincide with components of the control system 2111 described above with respect to FIG. 7; therefore, the descriptions of those components will not be repeated. In this aspect, the control system 8111 includes a set or assembly of multiple RFID scanners 8008 that are positioned or configured to read a corresponding set or assembly of RFID tags 8006. The RFID scanners 8008 are communicably coupled to a control circuit 1210 such that the control circuit 1210 can receive data from the RFID scanners 8008 and then take various actions based upon the read data, as are described below. In various aspects, the RFID scanners 8008 can be disposed on or otherwise associated with the surgical instrument or other surgical system component with which the control system 8111 is associated. In other aspects, the RFID scanners 8008 can be disposed on or otherwise associated with other surgical system components that are communicably couplable to the control system 8111. The RFID tags 8006 can be disposed on or associated with any type of surgical system component, including a surgical instrument 11112 (FIGS. 1-3), a visualization system 11108 (FIGS. 1-3), a robotic system 11110 (FIGS. 1-3), or other surgical system components (e.g., sterile drapes, rib spreaders, sponges, or adjuncts) or components thereof. In one aspect, each of the RFID scanners 8008a-h can be configured to read a corresponding RFID tag 8006a-h. Finally, it should be noted that although the control system 8111 in FIG. 7A is depicted as including eight RFID scanners 8008a-h that are configured to read a corresponding number of RFID tags 8006a-h, this particular number are arrangement of components is simply for illustrative purposes and should not be construed to be limiting in any way. In particular, the control system 8111 can include any number of RFID scanners 8008a-h that are configured to read any number of RFID tags 8006a-h.

Figure 11:
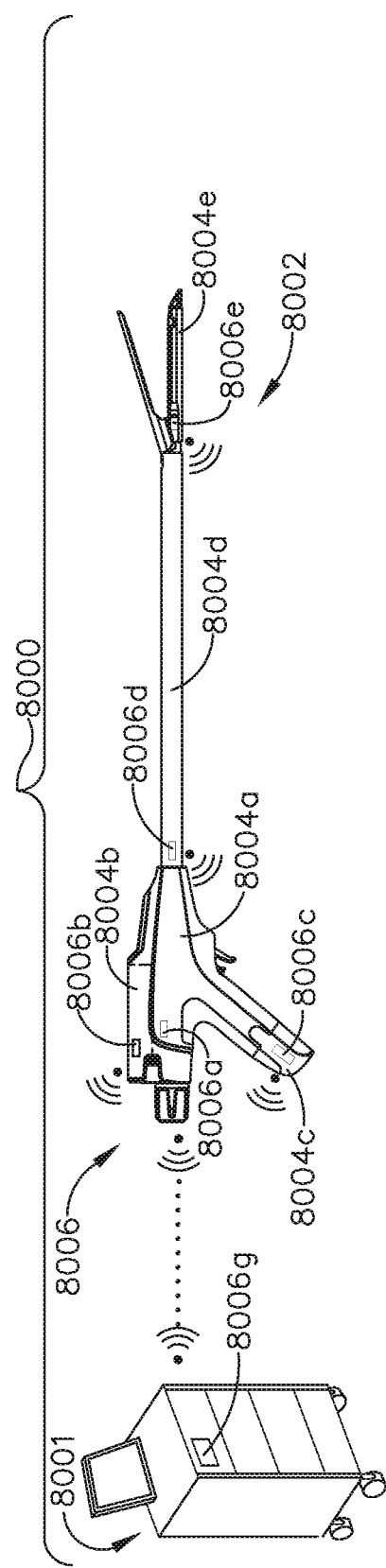
FIG. 11 illustrates a surgical instrument communicably coupled to a surgical hub, in accordance with at least one aspect of the present disclosure.

In one aspect, as described above under the heading SURGICAL HUBS and illustrated in FIG. 11, a surgical system 8000 can include a surgical instrument 8002 that is communicably couplable to a surgical hub 8001. Surgical instruments 8002 can include multiple different components that are couplable together to assemble the surgical instrument 8002 and/or consumable components that are insertable into the surgical instruments 8002 for firing or operating the surgical instruments 8002. For example, the illustrated surgical instrument 8002 can include a housing assembly 8004a, a battery 8004b removably couplable to the housing assembly 8004a, a motor assembly 8004c removably couplable to the housing assembly 8004a, a shaft 8004d removably couplable to the housing assembly 8004a, a cartridge 8004e removably insertable into the end effector of the shaft 8004d, and other such components.

The surgical system 8000 can further include the control system 8111. In the example of FIG. 11, the control system 8111 includes a set of RFIDs 8006 that are positioned on or otherwise associated with the various surgical instrument components 8004a-e. Each of the surgical instrument components 8004a-e can include an RFID tag 8006 that is configured to transmit information pertaining to the component with which the RFID tag 8006 is associated, such as the component type or component parameters, to a corresponding RFID scanner 8008 associated with the surgical instrument 8000 (e.g., the housing assembly 8004a), the surgical hub 8001, or another surgical system device. For example, in the depicted aspect, the housing assembly 8004a can include first RFID tag 8006a, the battery 8004b can include a second RFID tag 8006b, the motor assembly 8004c can include a third RFID tag 8006c, the shaft 8004d can include a fourth RFID tag 8006d, and the cartridge 8004e can include a fifth RFID tag 8006e. In one aspect, the RFID tags 8006a-e can be read by a single RFID scanner disposed on the surgical instrument 8002, the surgical hub 8001, or another component of a surgical system 8000. Accordingly, a control circuit 1210 of the control system 8111 can be communicably coupled to a single RFID scanner. In another aspect, the RFID tags 8006 can be read by multiple RFID scanners during the assembly or operation of the surgical instrument 8002. For example, the RFID scanners can be positioned on the surgical instrument 8002 such that the RFID tags 8006a-e are automatically read by a corresponding RFID scanner 8008a-e as a natural consequence of the assembly of the surgical instrument 8002 (an example of which is discussed in greater detail below with respect to FIG. 13) or the use of the surgical instrument 8002 (an example of which is discussed above with respect to FIGS. 8-10). Accordingly, the control circuit 1210 of the control system 8111 can be communicable coupled to multiple RFID scanners 8008 that are positioned to read one or more corresponding RFID tags 8006. Although the aspects depicted in FIGS. 8-11, 13, and 14 illustrate particular positions for the RFID tags 8006 and the RFID scanners 8008, it should be noted that these positions are simply for illustrative purposes and the RFID tags 8006 and/or RFID scanners 8008 can be repositioned depending upon the geometry of the particular surgical system component, have their positions swapped with each other, or be otherwise reconfigured without departing from the overall structure and function of the described systems.

In addition to the surgical instrument 8002 or components thereof, including RFID tags 8006, other devices within the surgical system 8000 can likewise include RFID tags 8006 and/or RFID scanners 8008. For example, in the aspect illustrated in FIG. 11, the surgical hub 8001 can include an RFID tag 8006g that can be configured to be read by one or more RFID scanners 8008 (FIG. 13) associated with the surgical instrument 8002. In other aspects, RFID tags 8006 and/or scanners 8008 can additionally or alternatively be associated with visualization system 11108 (FIGS. 1-3), a robotic system 11110 (FIGS. 1-3), or components thereof. Accordingly, a surgical instrument 8002 including an RFID scanner 8008 can detect the various devices or systems being utilized in the surgical system configuration based on being within detection range of those devices or systems.

Figure 13:
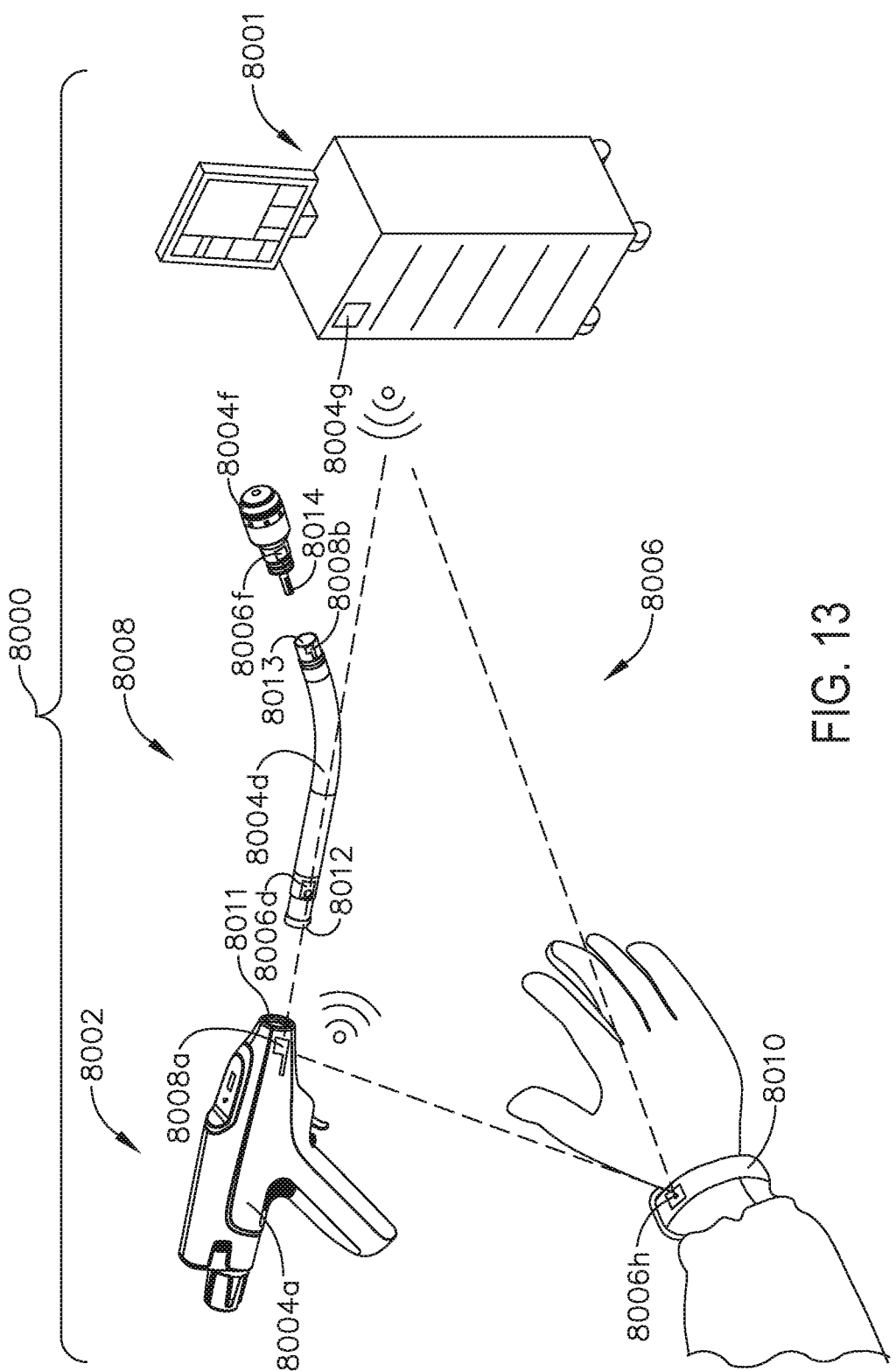
FIG. 13 illustrates a diagram of a surgical hub detecting RFID tags associated with a surgical instrument and a user, in accordance with at least one aspect of the present disclosure.

As illustrated in FIG. 13, a surgical system 8000 can also include a user identifier 8010 that can be worn or controlled by a user, such as a surgeon. The user identifier 8010 can include an RFID tag 8006h that is configured to store a unique identifier associated with the user, which can then be utilized by a control system to retrieve particular parameters or settings associated with that user. The user settings can be manually set by the user at a computer system (e.g., a surgical hub 8001 or a local computer system 11210 (FIG. 6)) or learned by a surgical hub 8001 through situational awareness, which is described in U.S. patent application Ser. No. 16/209,395, titled METHOD OF HUB COMMUNICATION, and filed Dec. 4, 2018, which is hereby incorporated by reference in its entirety. Further, the user settings can be stored in a database (e.g., storage 11248 (FIG. 6)) for retrieval by a control system.

In some aspects, RFID tags 8006 and RFID scanners 8008 can be positioned such that they are brought into detection range of each other during assembly of the surgical instrument 8002, or in an assembled configuration of the surgical instrument 8002. For example, FIG. 13 illustrates an aspect where the surgical instrument 8002 is a circular stapler including an assembly of RFID scanners 8008 that detect corresponding RFID tags 8006 during assembly of the surgical instrument 8002, or in the assembled configuration of the surgical instrument 8002. In particular, the housing assembly 8004*a* includes an RFID scanner 8008*a* positioned adjacent to its coupling portion 8011, which is configured to engage with a corresponding proximal coupling portion 8012 of the shaft assembly 8004*d*. The shaft assembly 8004*d* further includes an RFID tag 8006*d* that is brought into detection range of the RFID scanner 8008*a* when the aforementioned components are properly coupled together. In other words, the RFID scanner 8008*a* is positioned to read the RFID tag 8006*d* as a natural consequence of the assembly of the surgical instrument 8002. Likewise, the shaft assembly 8004*d* includes an RFID scanner 8008*b* positioned adjacent to a distal coupling portion 8013, which is configured to engage with a corresponding coupling portion 8014 of the end effector assembly 8004*f*. The end effector assembly 8004*f* further includes an RFID tag 8006*f* that is brought into detection range of the RFID scanner 8006*f* when the aforementioned components are properly coupled together. Therefore, the control system for the surgical instrument 8002 associated with this aspect can read the instrument components as they are assembled or coupled together and thereby control the surgical instrument 8002 accordingly based upon the presence, type, and/or arrangement of components being utilized.

In some aspects, RFID tags 8006 and RFID scanners 8008 can be positioned such that they are brought into detection range of each other during use of the surgical instrument 8002. For example, FIGS. 8-10, which are described in greater detail above, illustrate an aspect where a surgical instrument includes a pair of RFID tags 1201, 1203 that are recognizable or detectable by an RFID scanner 1202 when the stapling head assembly 1300 is in a closed configuration, i.e., where tissue is captured between the anvil 1200 and stapling head assembly 1300. Therefore, the control system for the surgical instrument associated with this aspect can read the instrument components as the surgical instrument is utilized or operated (e.g., during a surgical procedure) and thereby control the surgical instrument accordingly based upon the state of or actions being performed by the surgical instrument.

The RFID tags 8006 can also be positioned on consumables utilized by the surgical instrument 8002 during the operation thereof. For example, FIG. 14 illustrates an aspect where the surgical instrument 8002 is a clip applier including an RFID scanner 8008*c* positioned adjacently to the jaws 8020 for crimping or applying a surgical clip 8022 at a surgical site. The clips 8022 can include RFID tags 8006*i* that can be read by the RFID scanner 8008*c* as a consequence of the clip 8022 being positioned within the jaws 8020. Therefore, the control system for the surgical instrument associated with this aspect can read the consumables as the surgical instrument 8002 is utilized or operated (e.g., during a surgical procedure) and thereby control the surgical instrument 8002 accordingly based upon the type or characteristics of the consumables being utilized with the surgical instrument 8002. In various aspects, clips 8022 are fed to the jaws 8020 of the clip applier, and the fed clips 8022 become detectable by the RFID scanner 8008*c* as they reach the jaws 8020.

RFID tags 8006 can be configured to transmit a variety of different information to an associated RFID scanner 8008. Further, the various RFID tags 8006 described herein can be configured to transmit data in either an active manner (i.e., actively transmitting data for receipt by an RFID scanner 8008) or a passive manner (i.e., in response to an interrogation signal transmitted by an RFID scanner 8008). For example, the table 8030 illustrated in FIG. 12 indicates data that can be transmitted by RFID tags 8006 associated with the various components of the surgical instrument 8002 shown in FIG. 11. In particular, the RFID tag 8006*a* associated with the housing assembly 8004*a* can store a datum identifying the device or surgical instrument type; the RFID tag 8006*b* associated with the battery 8004*b* can store a datum identifying the battery type; the RFID tag 8006*c* associated with the motor assembly or gearbox 8004*c* can store a datum identifying the motor type; the RFID tag 8006*d* associated with the shaft assembly 8004*d* can store data identifying the shaft type and/or characteristics associated with the shaft (e.g., length or articulation type); and the RFID tag 8006*e* associated with the cartridge 8004*e* can store data identifying the cartridge type and/or other cartridge characteristics (e.g., length, color, or gripping surface type). This data can be transmitted by the RFID tags 8006 when read by a corresponding RFID scanner 8008, which in turn can be coupled to a control system for controlling the surgical instrument 8002. The various control algorithms that can be affected based upon this data can include communication protocols implemented by the control system.

As another example, the tables 8040, 8050 illustrated in FIGS. 15 and 16 indicate data that can be transmitted by RFID tags 8006 associated with consumables, such as the surgical clips 8022 as shown in FIG. 14. In particular, the RFID tags 8006*i* can store a datum identifying the type of the consumable (e.g., a product name, product code, or serial number) or characteristics of the consumable (e.g., cross-sectional profile, length, surface type, tensile strength, or spring back properties for a surgical clip 8022) with which each RFID tag 8006*i* is associated. Further, this data can be transmitted by the RFID tags 8006*i* for receipt by a corresponding RFID scanner 8008*c*, which in turn can be coupled to a control circuit 1210 that can utilize the received data for controlling the operations or functions of the surgical instrument.

With the surgical system 8000 configurations illustrated in FIGS. 7-11, 13, and 14, control systems for surgical instruments 8002 and other surgical system components can utilize a variety of different algorithms or logics for controlling the actions or operations of their subject devices by detecting the arrangement and/or type of surgical system components present within the operating room and/or the identifying users present within the operating room through the described RFID detection assemblies. In various examples, the control systems and associated RFID detection assemblies can be utilized to control communication protocols utilized by surgical instruments 8002, information or alerts provided to users, and/or operational settings implemented by surgical instruments 8002 to customize their functions according to the particular equipment between utilized and/or user preferences. In the following descriptions of processes, reference should also be made to FIG. 7. Further, the following processes describe, in part, scanning or receiving data from devices for controlling a surgical instrument 8002. Such devices can include a variety of different surgical system components, such as surgical instrument components (e.g., as shown in FIGS. 11,13, and 14), a visualization system 11108 (FIGS. 1-3), a surgical hub 11106 (FIGS. 1-3), a robotic system 11110 (FIGS. 1-3), and so on.

Figure 17:
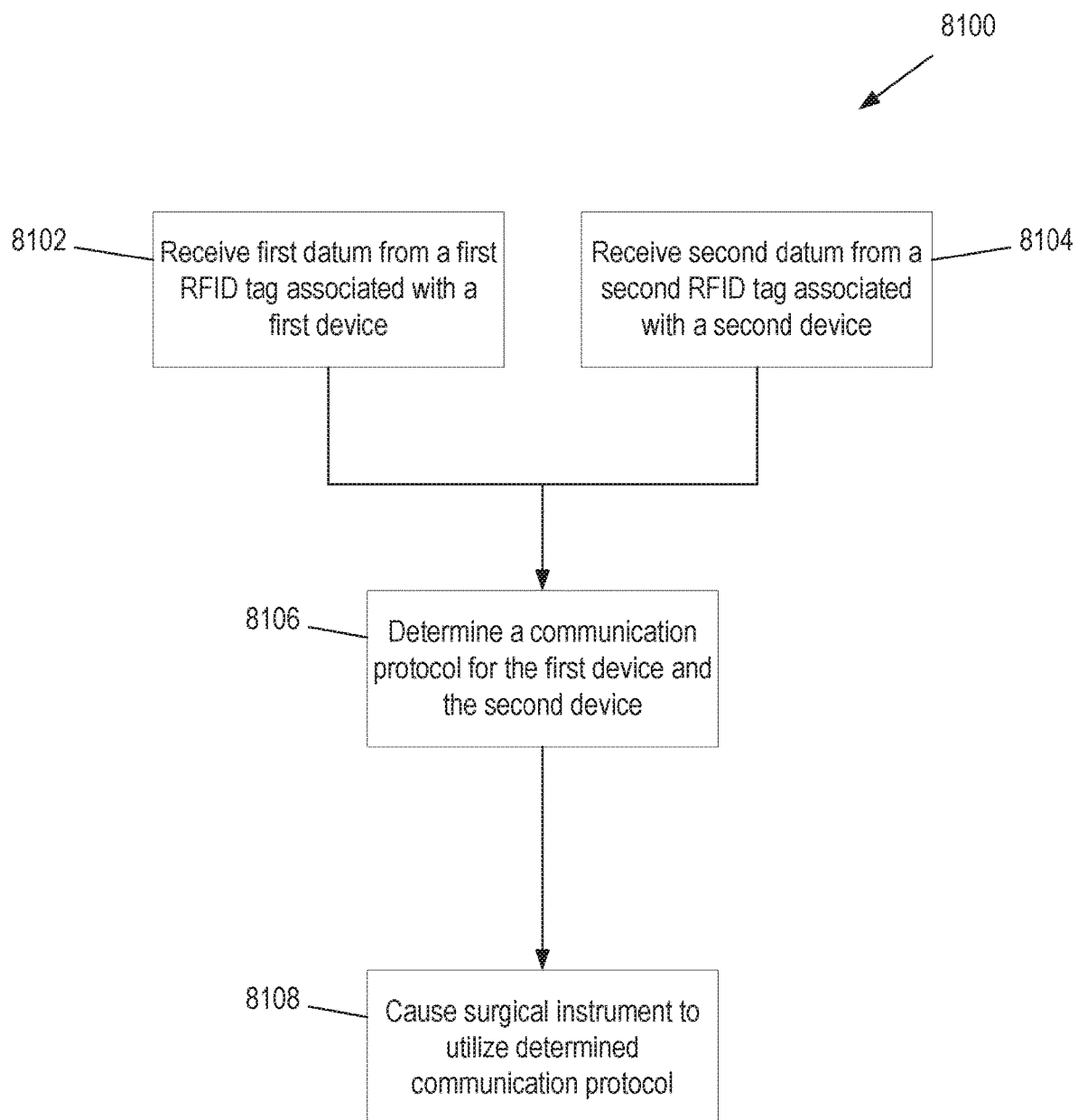
FIG. 17 illustrates a logic flow diagram of a process for determining a surgical instrument communication protocol via an RFID assembly, in accordance with at least one aspect of the present disclosure.

In one aspect, a control system 8111 for a surgical instrument 8002 can be configured to establish the communication protocol utilized by the surgical instrument 8002 for communicating with various other surgical system components according to RFIDs scanned thereby. For example, the control system 8111 can execute the process 8100 illustrated in FIG. 17. Accordingly, the control circuit 1210 receives 8102 a first datum from a first RFID tag associated with a first device and receives 8104 a second datum from a second RFID tag associated with a second device via one or more RFID scanners such as, for example, RFID scanners 8008 (FIG. 7A) to which the control circuit 1210 is coupled. The received data can indicate, for example, the serial number of a device, the device type, and/or characteristics or parameters associated with the device.

Accordingly, the control circuit 1210 determines 8106 a communication protocol for communicating with the first device and the second device. The control circuit 1210 can determine 8106 the appropriate communication protocol by, for example, querying a lookup table (e.g., stored in the memory 1212) with the received device data. The communication protocol can define, for example, encryption techniques, packet sizes, transmission speeds, or handshake techniques. Accordingly, the control circuit 1210 causes 8108 the surgical instrument 8002 to utilize the determined communication protocol for communicating with the surgical system components during the course of the surgical procedure.

In operation, a control system 8111 executing the illustrated process 8100 can read the RFID tags associated with the surgical system components present within the operating room, determine the appropriate communication protocol(s) for communicating with the particular arrangement of surgical system components, and then cause the surgical instrument 8002 to utilize the determined communication protocol. After establishment of communications between the surgical instrument 8002 and the corresponding surgical system components, the control circuit 1210 can be configured to receive an operational setting for the surgical instrument 8002 from at least one of the surgical system components. For example, if the surgical instrument 8002 is communicably coupled to a surgical hub 8001, 11106, the surgical instrument 8002 can download an updated control program setting forth updated operational settings or parameters from the surgical hub 8001, 11106. Alternatively, after establishment of communications between the surgical instrument 8002 and the corresponding surgical system components, the control circuit 1210 can be configured to transmit an operational setting for the surgical system component. For example, if the surgical instrument 8002 is communicably coupled to a robotic system 11110, the surgical instrument 8002 can transmit operational settings to the robotic system 11110 indicating how the surgical instrument 8002 should be controlled or actuated by the robotic system 11110 during a surgical procedure. Additionally, or alternatively, the surgical instrument 8002 can, for example, transmit sensor data to a surgical hub 8001, 11106.

Figure 18:
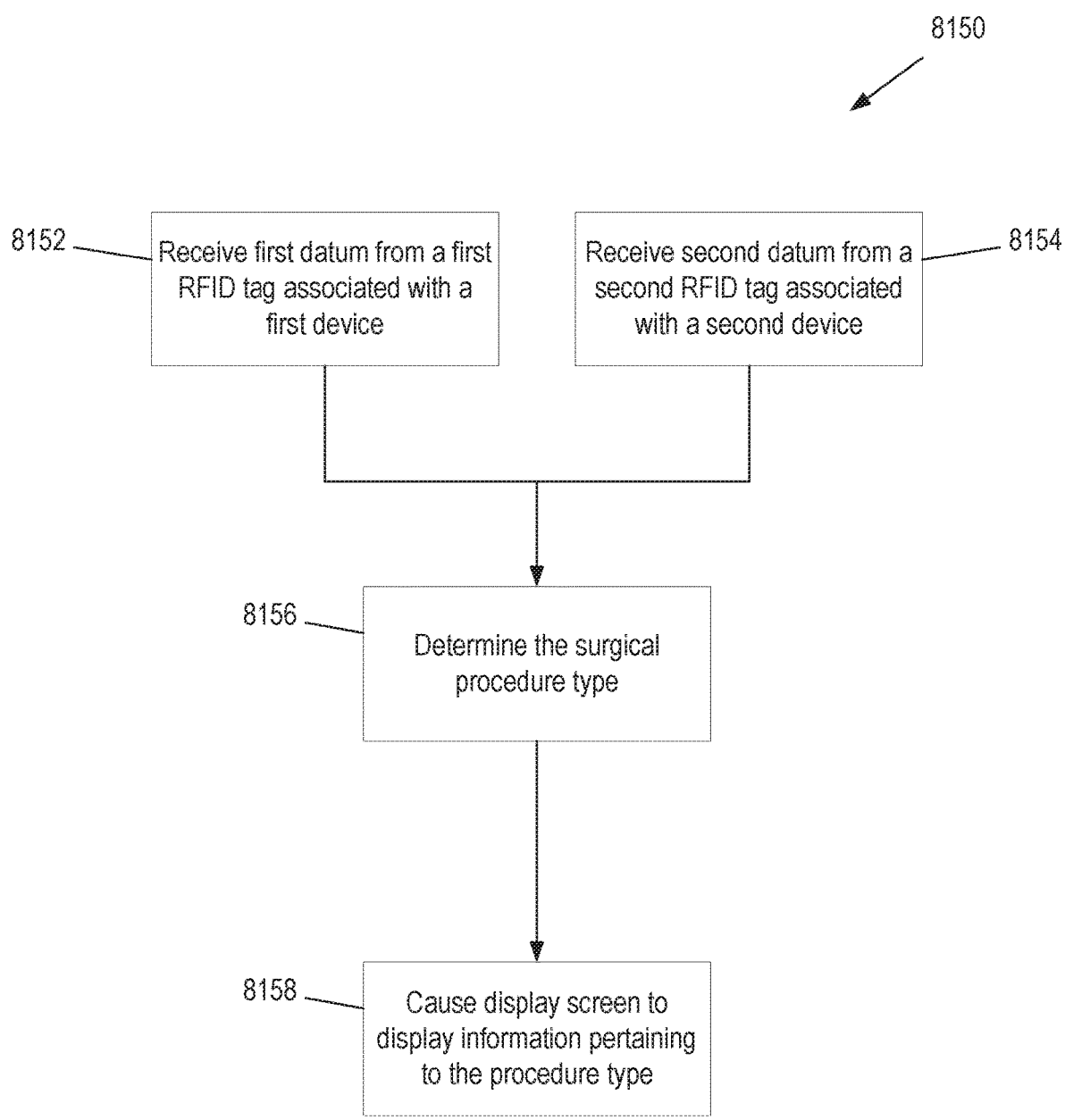
FIG. 18 illustrates a logic flow diagram of a process for determining surgical procedure information for display via an RFID assembly, in accordance with at least one aspect of the present disclosure.

In one aspect, a control system 8111 for a surgical instrument 8002 can be configured to automatically display information pertinent for the surgical procedure type. For example, the control system 8111 can execute the process 8150 illustrated in FIG. 18. Accordingly, the control circuit 1210 receives 8152 a first datum from a first RFID tag associated with a first device and receives 8154 a second datum from a second RFID tag associated with a second device via one or more RFID scanners such as, for example, RFID scanners 8008 (FIG. 7A) to which the control circuit 1210 is coupled. The received data can indicate, for example, the serial number of the device, the device type, and/or characteristics or parameters associated with the device.

Accordingly, the control circuit 1210 determines 8156 the type of surgical procedure that is being performed based upon the device data. The control circuit 1210 can make this determination because the particular combination or arrangement of device types within the operating room can indicate what type of surgical procedure is being performed. Further, the combination of data from multiple devices can indicate details of the surgical procedure that may not be possible to ascertain from scanning any individual device. For example, if a robotic system 11110 is present within the operating room along with a particular surgical instrument type (e.g., a circular stapler or a vascular stapler), then the surgical procedure corresponding to the surgical instrument type is likely going to be performed robotically. As another example, if an insufflator and a visualization system 11108 is presented within the operating room, then a laparoscopic procedure is likely going to be performed. In either of these examples, scanning an individual device would often not provide the full context for the procedure. The control circuit 1210 can determine 8156 the surgical procedure type by, for example, querying a lookup table (e.g., stored in the memory 1212) with the received device data. Subsequently, the control circuit 1210 causes 8158 a display screen (e.g., the indicator 1209 or the hub display 11215 (FIG. 5)) to display information relevant to the surgical procedure type. The displayed information can include, for example, steps for performing the surgical procedure, steps for assembling the surgical instrument 8002 or other surgical system components, relevant data or visualization screens for the surgical instrument types expected to be utilized in association with the procedure, and so on.

Figure 19:
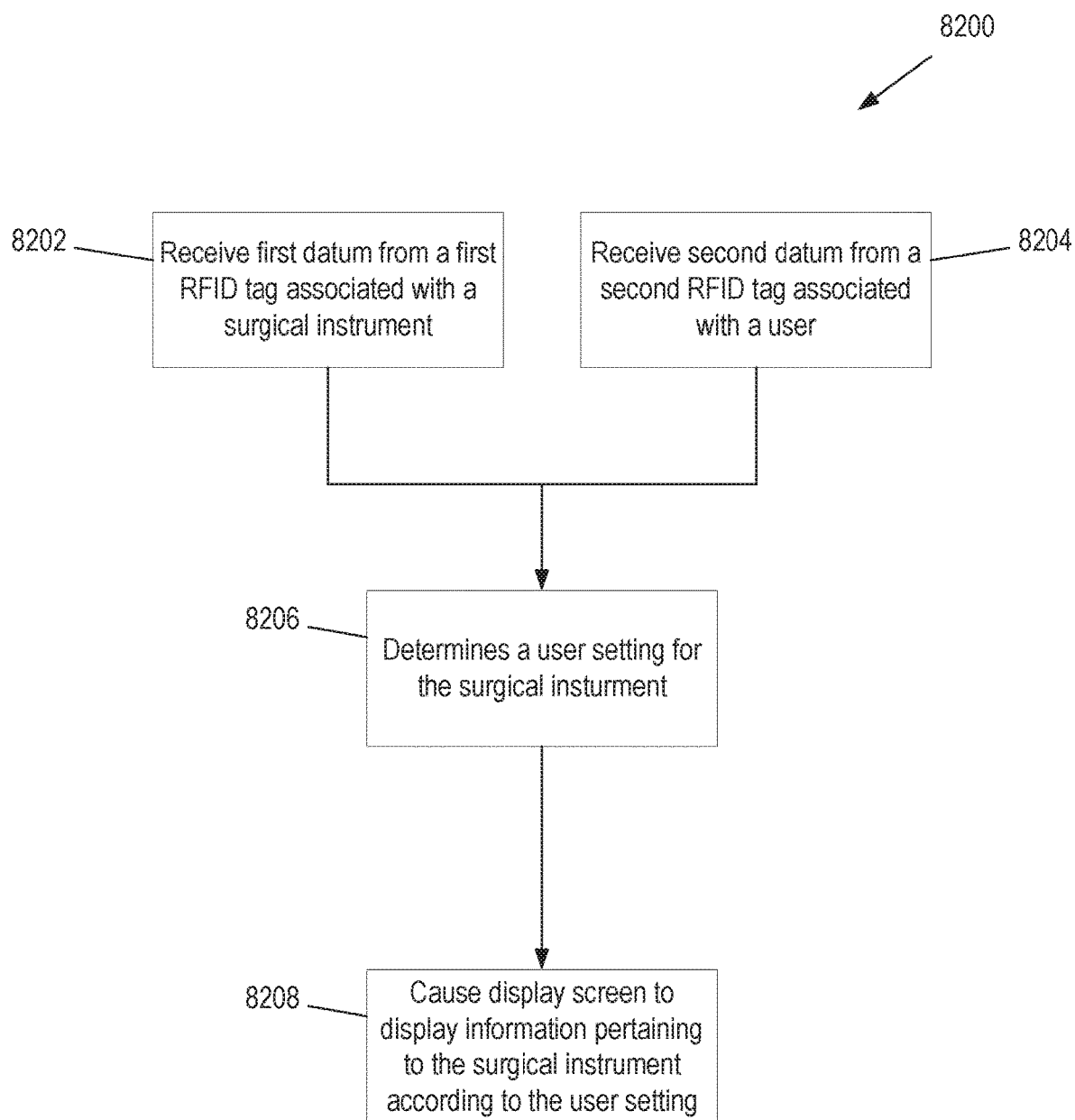
FIG. 19 illustrates a logic flow diagram of a process for determining information tailored to a user via an RFID assembly, in accordance with at least one aspect of the present disclosure.

In one aspect, a control system 8111 for a surgical instrument 8002 can be configured to automatically display information that is customized for the particular user. For example, the control system 8111 can execute the process 8200 illustrated in FIG. 19. Accordingly, the control circuit 1210 receives 8202 a first datum from a first RFID tag associated with a device or surgical instrument and receives 8204 a second datum from a second RFID tag associated with a user (e.g., from a user identifier 8010 as illustrated in FIG. 13) via one or more RFID scanners such as, for example, RFID scanners 8008 (FIG. 7A) to which the control circuit 1210 is coupled. The data received from the instrument or device can indicate, for example, the serial number of the device, the device type, and/or characteristics or parameters associated with the device. The data received from the user identifier 8010 can indicate, for example, the identity or title of the user.

Accordingly, the control circuit 1210 determines 8206 a user setting associated with the surgical instrument. The user settings can include a magnification for a particular scope type, instrument parameter information (e.g., temperature, force to fire, or power level), and so on. The control circuit

1210 can determine 8206 the user setting by retrieving the relevant user setting(s) (e.g., from the memory 1212). As noted above, the user settings can be manually set by the user at a computer system or automatically learned by the surgical system through situational awareness. Accordingly, the control circuit 1210 causes 8208 a display screen to display information pertaining to the surgical instrument according to the determined user setting(s).

Figure 20:
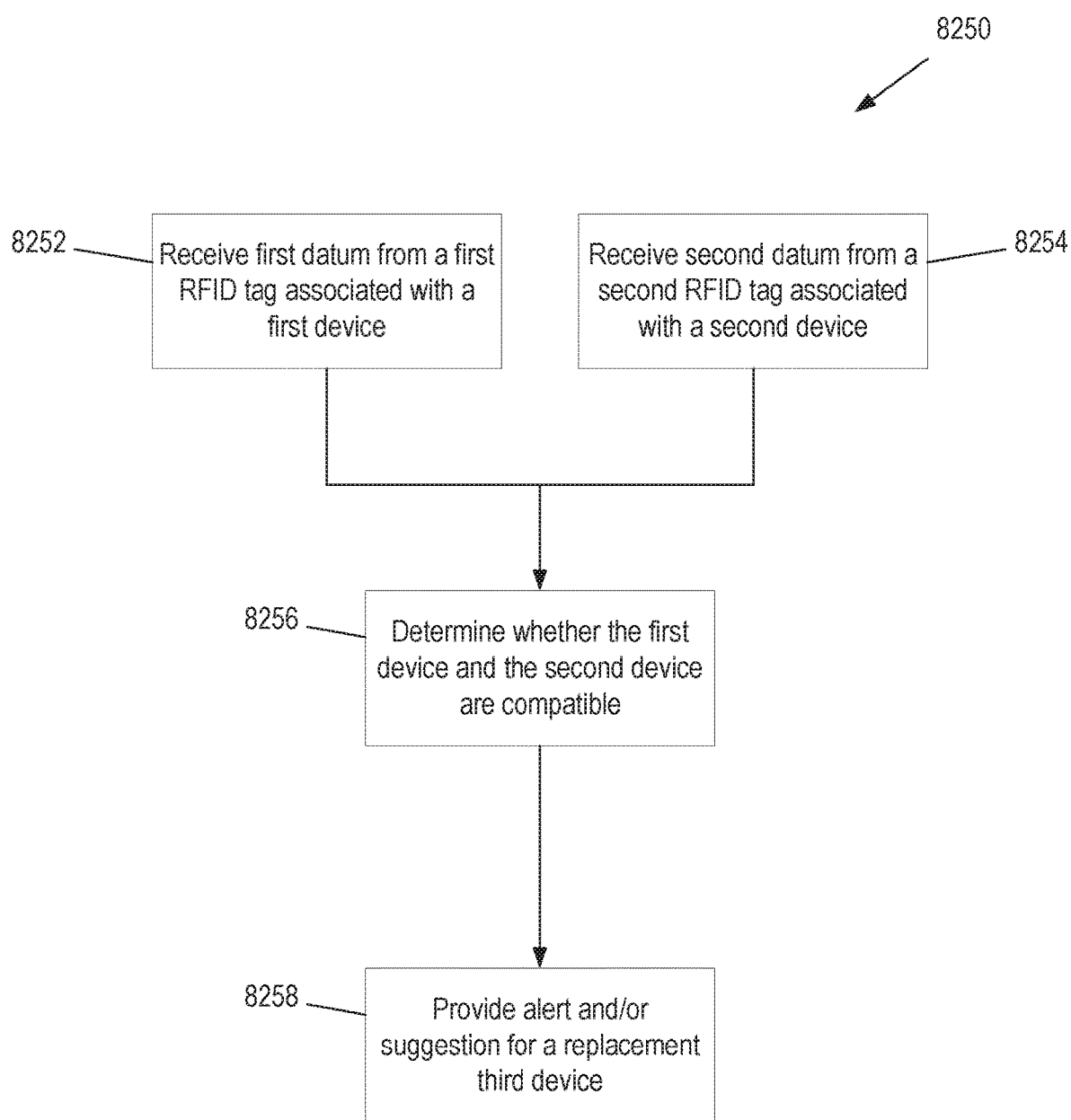
FIG. 20 illustrates a logic flow diagram of a process for determining whether surgical system components are compatible via an RFID assembly, in accordance with at least one aspect of the present disclosure.

In one aspect, a control system 8111 for a surgical instrument 8002 can be configured to determine whether surgical instrument components are compatible with each other and then take various correct actions. For example, the control system 8111 can execute the process 8250 illustrated in FIG. 20. Accordingly, the control circuit 1210 receives 8252 a first datum from a first RFID tag associated with a first device and receives 8254 a second datum from a second RFID tag associated with a second device via one or more RFID scanners such as, for example, RFID scanners 8008 (FIG. 7A) to which the control circuit 1210 is coupled. The received data can indicate, for example, the serial number of the device, the device type, and/or characteristics or parameters associated with the device.

Accordingly, the control circuit 1210 determines 8256 whether the first device and the second device are compatible. The control circuit 1210 can determine 8256 whether the devices are compatible by, for example, querying a lookup table (e.g., stored in the memory 1212) setting forth compatible surgical instrument device types with the received device data. The control system 8111 can be manufactured to store lists of compatible component types or receive compatible component types from a remote computing system (e.g., the cloud 11204 (FIG. 5)) to which the control system 8111 is communicably coupled, for example. If the components are determined 8256 to be incompatible with each other, the control circuit 1210 can provide 8258 an alert to the user that the components are incompatible and/or a suggestion of a replacement compatible component for one of the incompatible components. For example, if the user inserts a battery 8004b into the housing assembly 8004a of the surgical instrument 8002 that is incompatible with the motor assembly 8004c, the control system 8111 can cause the display (e.g., indicator 1209) to provide 8258 an alert or a suggestion for an alternative type of battery 8004b that is compatible with the motor assembly 8004c. In one aspect, the control circuit 1210 can further be configured to prevent the operation or activation of the surgical instrument 8002 in the event that the first and second devices are determined to be incompatible with each other.

In various aspects, preventing the operation or activation of a surgical instrument 8002 can be achieved using one or more suitable lockout assemblies such as, for example, a lockout assembly 8170. Various lockout out assemblies that are suitable for use with the present disclosure are described in U.S. Pat. No. 7,143,923, entitled SURGICAL STAPLING INSTRUMENT HAVING A FIRING LOCKOUT FOR AN UNCLOSED ANVIL, which issued on Dec. 5, 2006; U.S. Pat. No. 7,044,352, SURGICAL STAPLING INSTRUMENT HAVING A SINGLE LOCKOUT MECHANISM FOR PREVENTION OF FIRING, which issued on May 16, 2006; U.S. Pat. No. 7,000,818, SURGICAL STAPLING INSTRUMENT HAVING SEPARATE DISTINCT CLOSING AND FIRING SYSTEMS, which issued on Feb. 21, 2006; U.S. Pat. No. 6,988,649, SURGICAL STAPLING INSTRUMENT HAVING A SPENT CARTRIDGE LOCKOUT, which issued on Jan. 24, 2006; and U.S. Pat. No. 6,978,921, SURGICAL STAPLING INSTRUMENT INCORPORATING AN E-BEAM FIRING MECHANISM, which issued on Dec. 27, 2005, which are incorporated by reference herein in their entireties.

Figure 21A:
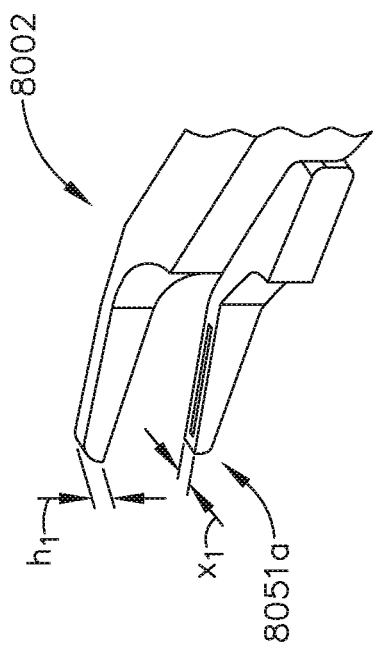
FIG. 21A illustrates a perspective view of a first jaw assembly for a surgical clip applier, in accordance with at least one aspect of the present disclosure.
Figure 21B:
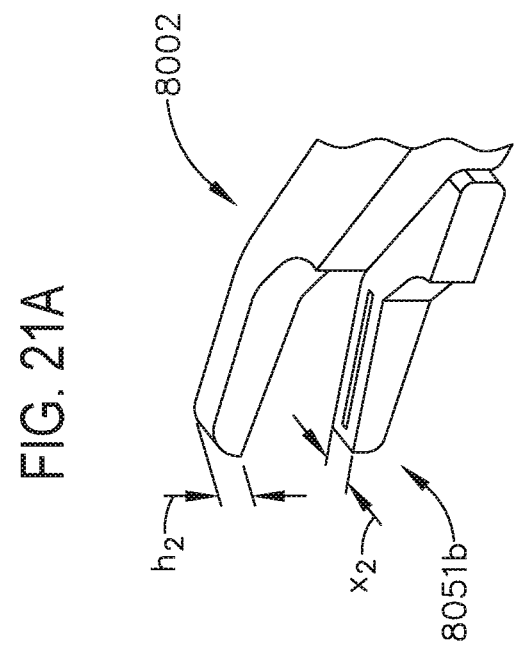
FIG. 21B illustrates a perspective view of a second jaw assembly for a surgical clip applier, in accordance with at least one aspect of the present disclosure.
Figure 22:
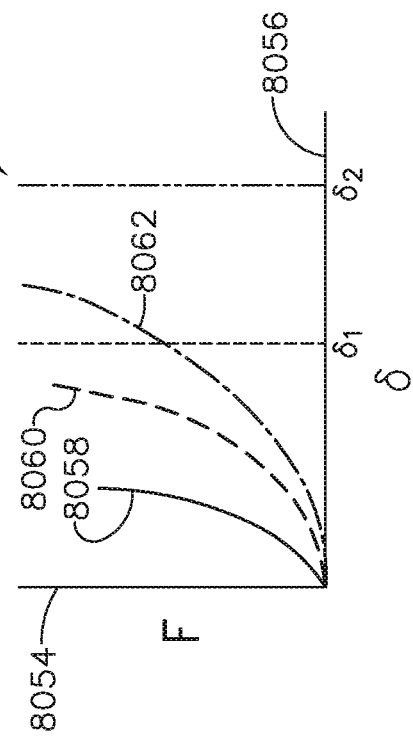
FIG. 22 illustrates a graph depicting force relative to displacement stroke for various surgical clip applier firings as controlled by a control system, in accordance with at least one aspect of the present disclosure.

As another example, a surgical instrument 8002 in the form of a surgical clip applier can have different types of jaw assemblies that are appropriate for different types of surgical clips 8022, such as a first, or thin, jaw assembly 8051a shown in FIG. 21A and a second, or thick, jaw assembly 8051b shown in FIG. 21B. FIG. 22 illustrates a graph 8052 depicting the relationship between force applied to form or crimp the surgical clip, represented by the vertical axis 8054, and a displacement stroke causing the force application, represented by the horizontal axis 8056, for multiple prophetic firings of a clip applier including a control system 8111 executing the process 8250 illustrated in FIG. 20. A first distance threshold $\delta_1$ represents the maximum stroke distance that a clip applier having a thin jaw assembly 8051a is capable of performing. Further, a second distance threshold $\delta_2$ represents the maximum stroke distance that a clip applier having a thick jaw assembly 8051b is capable of performing. As further illustrated in the table 8050 in FIG. 16, different types of surgical clips 8022 can have different mechanical properties; therefore, some types of surgical clips may not be suitable for use with all types of clip appliers. In this particular prophetic example, the first line 8058 represents a first clip type (e.g., a Ti-CP clip), the second line 8060 represents a second clip type (e.g., Ti-3Al/2.5V clip), and the third line 8062 represents a third clip type (e.g., a Ti-6Al-4V clip). In this implementation of the process 8250, the clip applier can be the first device and the surgical clip can be the second device. Accordingly, if a control circuit 1210 executing the process 8250 determines that the surgical clip read by the RFID scanner 8008 (e.g., when the clip is inserted into the clip applier) is the first type or the second type, then no alert or suggestion is provided to the user for either of the clip applier types shown in FIGS. 21A and 21B because both of these clip types are compatible with either clip applier type (as indicated by neither of the lines 8058, 8060 violating the respective thresholds $\delta_1$, $\delta_2$). However, if the control circuit 1210 determines that the surgical clip read by the RFID scanner 8008 is the third type and the clip applier is the thin jaw assembly type 8051a, then the control circuit 1210 can provide an alert and/or a suggestion for a replacement surgical clip because the maximum displacement stroke $\delta_1$ for the thin jaw assembly type 8051a is not long enough to properly form the third clip type (as indicated by the third line 8062 crossing the threshold $\delta_1$).

In one aspect, a control system 8111 for a surgical instrument 8002 can be configured to automatically establish the operational settings of the surgical instrument 8002 according to the scanned components. For example, the control system 8111 can execute a process 8300 illustrated in FIG. 23. Accordingly, the control circuit 1210 receives 8302 a first datum from a first RFID tag associated with a first device and receives 8304 a second datum from a second RFID tag associated with a second device via one or more RFID scanners such as, for example, RFID scanners 8008 (FIG. 7A) to which the control circuit 1210 is coupled. The received data can indicate, for example, the serial number of the device, the device type, and/or characteristics or parameters associated with the device. As one example, the devices can include two or more of the components of the surgical instrument 8002 illustrated in FIGS. 11 and 12. As another example, the devices can include two or more of the components of the surgical instrument 8002 illustrated in FIG. 13.

Accordingly, the control circuit 1210 can determine 8306 the surgical instrument type based upon the scanned components. The surgical instrument type can include, for example, the general instrument type (e.g., a surgical stapler, an electrosurgical instrument, an ultrasonic surgical instrument, or combinations thereof) in combination with particular instrument component parameters (e.g., shaft length, cartridge type, or battery power). In one aspect, the RFID scanner(s) 8008 can be positioned such that the RFID tags associated with each of the components are naturally read by the RFID scanner(s) 8008 as a natural consequence of the assembly or utilization of the surgical instrument 8002, as described above in connection with FIGS. 13 and 14. Accordingly, the control circuit 1210 can determine 8308 an operational setting according to the determined instrument type. The operational settings can dictate how the surgical instrument 8002 itself (or a component thereof) is controlled or how a third device (e.g., a surgical generator that the surgical instrument 8002 is coupled to) is controlled. The table 8030 illustrated in FIG. 12 indicates various settings that could be controlled by a control circuit 1210 according to the determined instrument type. For example, a control circuit 1210 executing the process 8300 could control the maximum power of the surgical instrument 8002 according to the detected battery type and the detected motor assembly type. As another example, a control circuit 1210 executing the process 8300 could control the force to fire a knife in a surgical stapler according to the detected motor assembly type and the detected cartridge type.

In one aspect, a control system 8111 for a surgical instrument 8002 can be configured to automatically establish the operational settings of the surgical instrument 8002 according to consumables that are scanned as they are assembled with and/or inserted into the surgical instrument 8002. For example, the control system 8111 can execute the process 8350 illustrated in FIG. 24. Accordingly, the control circuit 1210 receives 8352 a first datum from a first RFID tag associated with a device or surgical instrument 8002 and receives 8354 a second datum from a second RFID tag associated with a consumable via one or more RFID scanners such as, for example, RFID scanners 8008 (FIG. 7A) to which the control circuit 1210 is coupled. The received data can indicate, for example, the serial number of the surgical instrument 8002 or consumable, the surgical instrument 8002 or consumable type, and/or characteristics or parameters associated with the surgical instrument 8002 or consumable. For example, the surgical instrument 8002 can include a clip applier and the consumable can include a surgical clip 8022, as shown in FIG. 14. As another example, the surgical instrument 8002 can include a surgical stapler and the consumable can include staples disposed within a cartridge 8004e, as shown in FIG. 12.

Accordingly, the control circuit 1210 determines 8356 an operational setting according to the consumable type and the surgical instrument type. The control circuit 1210 can determine 8356 the operational setting by, for example, querying a lookup table (e.g., stored in the memory 1212) setting forth the appropriate operational settings for the surgical instrument according to the scanned consumable. The control system 8111 can be manufactured to store operational settings for various compatible device types or receive operational settings from a remote computing system (e.g., the cloud 204 (FIG. 5)) to which the control system 8111 is communicably coupled, for example. Accordingly, the control circuit 1210 can then control 8358 the surgical instrument according to the determined operational setting(s).

Various prophetic implementations of the process 8350 are illustrated in connection with FIGS. 25 and 26. For example, FIG. 25 illustrates a graph 8064 depicting the relationship between force applied to the surgical clip, represented by the vertical axis 8066, and displacement stroke, represented by the horizontal axis 8068, for a clip applier including a control system 8111 executing the process 8350 illustrated in FIG. 24. In this example, the control circuit 1210 can determine that the surgical instrument is a clip applier and can determine the identity of the consumables as they are loaded into the clip applier, as discussed above in relation to FIG. 14. In a first firing of the clip applier, represented by the first line 8070, the control circuit 1210 further determines that the consumable is a first type of surgical clip (e.g., a Ti-CP clip). For this type of clip, the controlled operational parameters include a first force threshold $F_1$ and a first closure rate $V_1$. Accordingly, the control circuit 1210 controls the clip applier according to the determined operational parameters, i.e., closes the jaws of the clip applier at the first closure rate $V_1$ and halts closure at or below the first force threshold $F_1$. In a second firing of the clip appliers, represented by the second line 8072, the control circuit 1210 determines that the consumable is a second type of surgical clip (e.g., a Ti-6Al-4V clip). For this type of clip, the appropriate operational parameters include a second force threshold $F_2$ and a second closure rate $V_2$. Accordingly, the control circuit 1210 controls the clip applier according to the determined operational parameters, i.e., closes the jaws of the clip applier at the second closure rate $V_2$ and halts closure at or below the second force threshold $F_2$.

Figure 24:
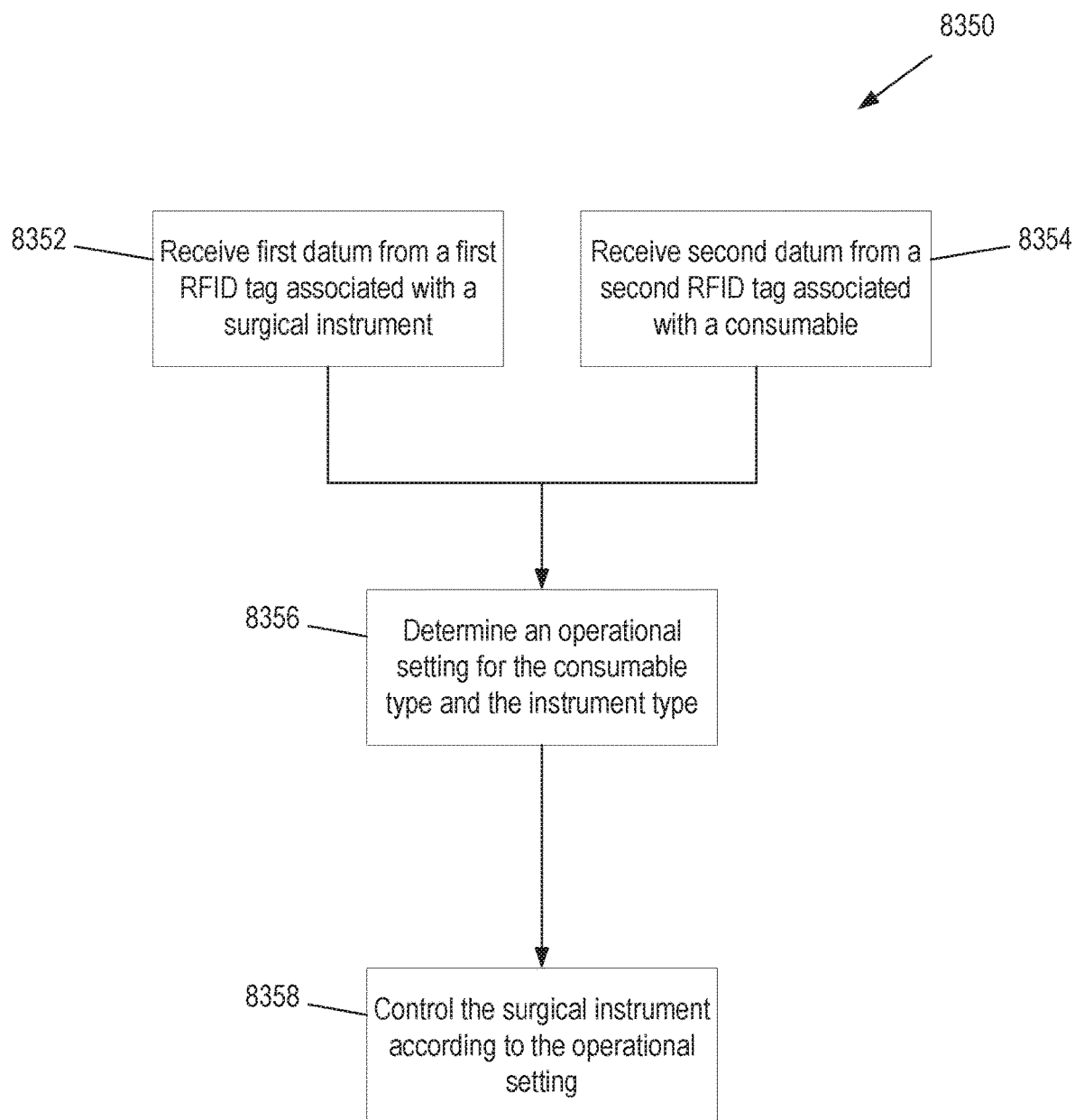
FIG. 24 illustrates a logic flow diagram of a process for determining surgical instrument operational settings according to consumable type via an RFID assembly, in accordance with at least one aspect of the present disclosure.
Figure 26:
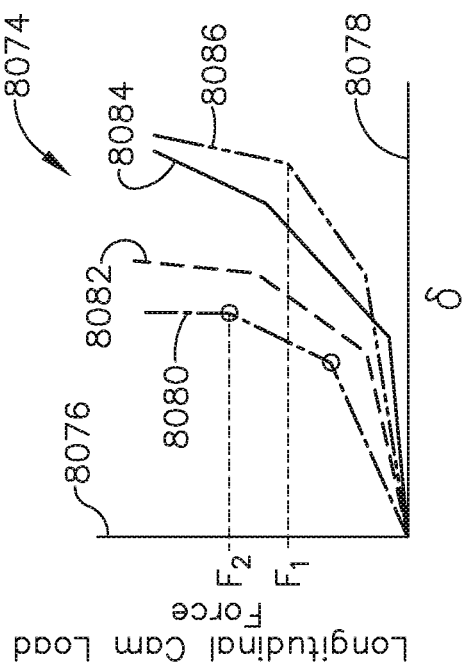
FIG. 26 illustrates a graph depicting longitudinal cam load force relative to displacement stroke for various surgical clip applier firings as controlled by a control system, in accordance with at least one aspect of the present disclosure.
Figure 25:
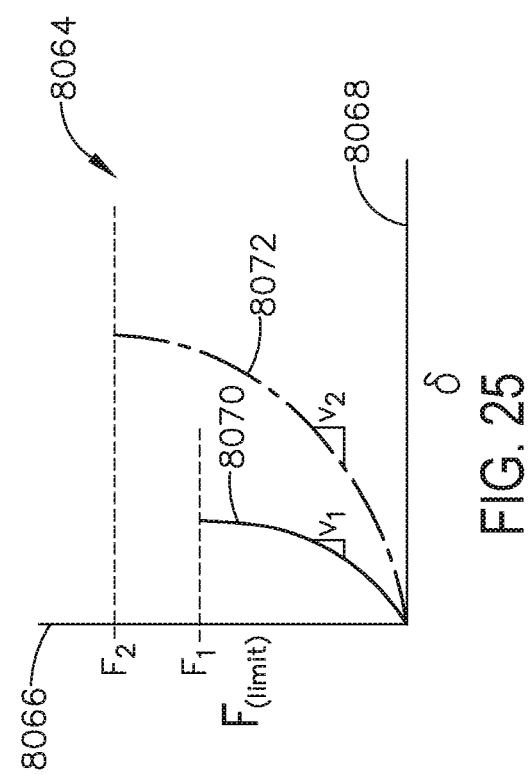
FIG. 25 illustrates a graph depicting force relative to displacement stroke for various surgical clip applier firings as controlled by a control system, in accordance with at least one aspect of the present disclosure.

As another example, FIG. 26 illustrates a graph 8074 depicting the relationship between longitudinal cam load force, represented by the vertical axis 8076, and displacement stroke, represented by the horizontal line 8078, for multiple prophetic firings of a clip applier including a control system 8111 executing the process 8350 illustrated in FIG. 24. In a clip applier, a camming assembly can be configured to apply a closing force to the jaws and thereby apply a clip to tissue positioned within the jaws. Accordingly, the longitudinal cam load force can correspond to the amount of force being imparted upon the jaws of the clip applier. The displacement stroke can correspond to the distance that the cam of the camming assembly has been translated. The profile of the cam force applied by the surgical clip applier as a function of the distance by which the cam has been translated is a controllable parameter that can be tailored to different clip applier assemblies (e.g., as shown in FIGS. 21A and 21B) and/or different surgical clip types. In various aspects, this controllable parameter can be automatically selected by a control system 8111 for the surgical instrument and/or manually selected by a user. In this example, the control circuit 1210 has received 8352 a first datum from the surgical instrument identifying the surgical instrument as a clip applier, received 8454 a second datum identifying the consumable as a particular type of surgical clip, determined 8456 that the particular surgical clip type is associated with a particular cam force profile, and then controlled 8458 the clip applier according to the determined force profiles, as shown by the various lines 8080, 8082, 8084, 8086. The first line 8080 can correspond to the force profile determined 8356 by the control circuit 1210 for a first clip applier type (e.g., the jaw assembly 8051a illustrated in FIG. 21A) and first surgical clip type (e.g., a Ti-6Al-4V clip). The second line 8082 can correspond to the force profile determined 8356 by the control circuit 1210 for a first clip applier type and a second surgical clip type (e.g., a Ti-3AV/2.5V clip). The third line 8084 can correspond to the force profile determined 8356 by the control circuit 1210 for a first clip applier type and a third surgical clip type (e.g., a Ti-CP clip). The fourth line 8086 can correspond to the force profile determined 8356 by the control circuit 1210 for a second clip applier type (e.g., the jaw assembly 8051*b* illustrated in FIG. 21B) and a third surgical clip type.

Figure 27:
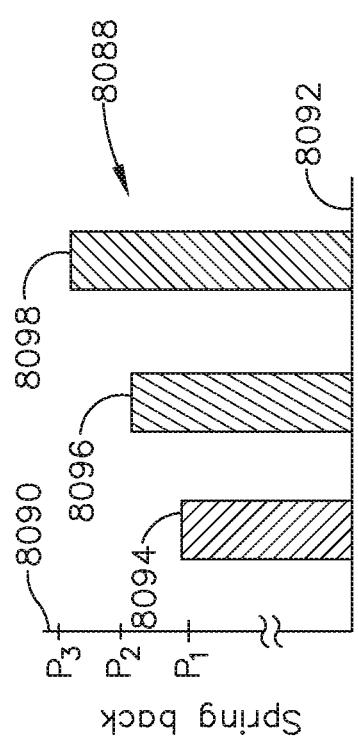
FIG. 27 illustrates a graph depicting spring back properties for various type of surgical clips, in accordance with at least one aspect of the present disclosure.

It can be desirable to utilize applied force profiles that are tailored to the types of clip appliers and surgical clips being utilized because different types of clip appliers apply forces in different ways and different types of surgical clips have different mechanical properties. Some examples of different mechanical properties are illustrated in the tables 8040, 8050 of FIGS. 15 and 16. Another mechanical property for which surgical clips can differ is the degree to which the surgical clips spring back in response to applied forces, which can in turn affect the degree or amount of force that one would wish to apply to the surgical clips to have them maintained in a desired configuration. For example, FIG. 27 illustrates a graph 8088 depicting the relationship between the spring back, represented by the vertical axis 8090, for different surgical clip types, represented by the horizontal axis 8092. The spring back can correspond to the percentage or degree to which a surgical clip will return relative to its initial position in response to a set force, for example. As can be seen from the graph 8088, a first surgical clip type 8094 has a spring back of $P_1$, a second surgical clip type 8096 has a spring back of $P_2$, and a third surgical clip type 8098 has a spring back of $P_3$. Therefore, it would be desirable for a control circuit 1210 executing the process 8350 illustrated in FIG. 24 to read which surgical clip type has been loaded into the clip applier and then adjust the applied force profile, at least based in part on the spring-back characteristic of a detected clip type.

In one aspect, a control system 8111 for a surgical instrument 8002 can be configured to automatically implement operational settings of the surgical instrument 8002 that are customized for a particular user. For example, the control system 8111 can execute the process 8400 illustrated in FIG. 28. Accordingly, the control circuit 1210 receives 8402 a first datum from a first RFID tag associated with a device or surgical instrument and receives 8404 a second datum from a second RFID tag associated with a user (e.g., from a user identifier 8010 as illustrated in FIG. 13) via one or more RFID scanners such as, for example, RFID scanners 8008 (FIG. 7A) to which the control circuit 1210 is coupled. The data received from the instrument or device can indicate, for example, the serial number of the device, the device type, and/or characteristics or parameters associated with the device. The data received from the user identifier 8010 can indicate, for example, the identity or title of the user.

Accordingly, the control circuit 1210 determines 8406 an operational setting for the surgical instrument that is associated with the user. The control circuit 1210 can determine 8406 the user setting by retrieving the relevant user setting(s) (e.g., from the memory 1212). As noted above, the user settings can be manually set by the user at a computer system or automatically learned by the surgical system through situational awareness. In one aspect, the determined operational setting can be selected from a range for the parameter. The user can manually select a value or the surgical system can learn the user's preference within the parameter range, for example. Accordingly, the control circuit 1210 can control the surgical instrument according to the operational setting associated with the user.

Various prophetic implementations of the process 8350 of FIG. 24 are illustrated in connection with FIGS. 29-31. For example, FIG. 29 illustrates a staple height widget or icon 8500 that is displayable on a graphical user interface. The staple height or degree of deformation applied by a surgical stapler to deployed staples is a controllable parameter. The graphical user interface can be displayed on, for example, a device/instrument display 11237 or a hub display 11215. The staple height widget 8500 can include a range icon 8502 to indicate a suggested selection range for the staple height and a selection icon 8504 indicating the actual staple height that has been selected for the surgical stapler. In various aspects, the staple height widget 8500 can be manually manipulated by a user of the surgical stapler and/or controlled by a control system 8111 of the surgical stapler. In this example, the control circuit 1210 has received 8402 a first datum from the surgical instrument identifying the surgical instrument as a surgical stapler and/or from the staple cartridge identifying the cartridge type, received 8404 a second datum identifying the user, determined 8406 that the user identity is associated with a particular staple height setting for surgical staplers, and then controlled 8408 the surgical stapler to set the staple height to the defined setting indicated by the selection icon 8504.

Figure 28:
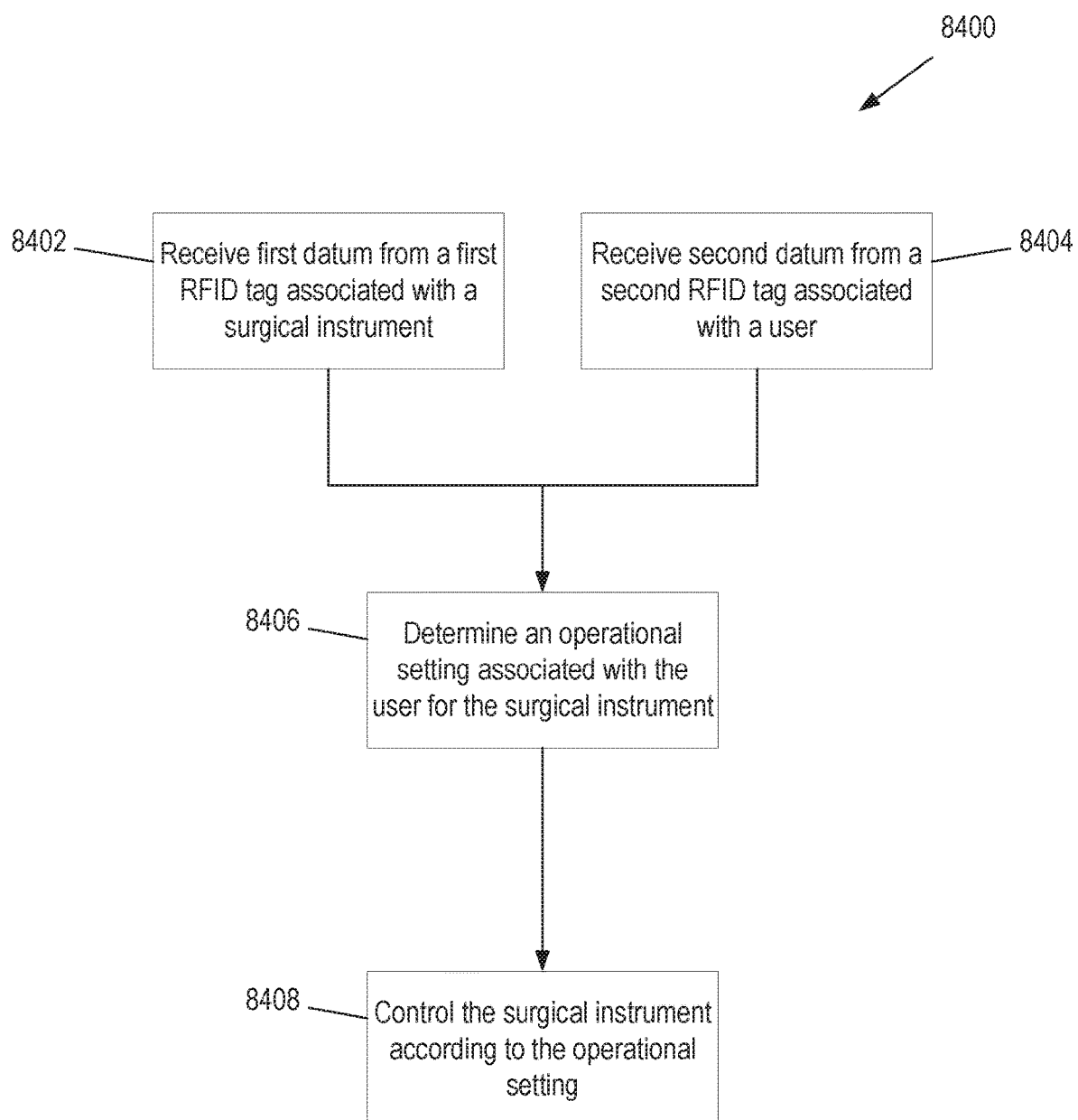
FIG. 28 illustrates a logic flow diagram of a process for determining surgical instrument operational settings tailored to a user via an RFID assembly, in accordance with at least one aspect of the present disclosure.

As another example, FIG. 30 illustrates a graph 8510 depicting the relationship between force, represented by the vertical axis 8512, and displacement stroke, represented by the horizontal axis 8516, for a prophetic firing of a surgical stapler including a control system 8111 executing the process 8400 illustrated in FIG. 28. The force represented by the vertical axis 8512 can correspond to the force experienced by or imparted upon a firing member configured to close the jaws of a surgical stapler, fire staplers, and/or cut tissue captured by the jaws. The force represented by the vertical axis 8512 can also correspond to the force load generated by a motor. The displacement stroke represented by the horizontal axis 8516 can correspond to the distance traveled by a firing member, which can be delineated into two distinct phases. In a first or closure phase, represented by the first line 8520, the firing member is driving closure of the jaws. In a second or firing phase, represented by the second line 8524, the firing member is deploying staples and cutting tissue. The speed at which the firing member is translated during the closure phase (i.e., the closure speed) and the speed at which the firing member is translated during the firing phase (i.e., the firing speed) are both controllable parameters. Further, the force threshold representing the maximum force that is permitted to be experienced by the surgical instrument before the control system 8111 halts the translation of the firing member or takes other corrective actions is likewise a controllable parameter. The force threshold can depend upon the particular surgical instrument component types that are being utilized. For example, the first force threshold $FT_1$ can represent the standard or base force limit, the second force threshold $FT_2$ can represent the force limit for a particular shaft type, and the third force threshold $FT_3$ can represent the force limit for a particular cartridge type. In various aspects, these controllable parameters can be automatically selected by a control system 8111 for the surgical instrument and/or manually selected by a user. This particular graph 8510 illustrates that the control system 8111 for the surgical instrument is executing two separate processes.

In particular, the graph 8510 demonstrates that a control circuit 1210 executing the process 8400 illustrated in FIG. 28 has received 8402 a first datum from the surgical instrument identifying the surgical instrument as a surgical stapler, received 8404 a second datum identifying the user, determined 8406 that the user identity is associated with a particular surgical stapler closure speed setting selected from a permitted closure speed range 8518 and a particular surgical stapler firing speed setting selected from a permitted firing speed range 8522, and then controlled 8408 the surgical stapler to drive the firing member at the selected speeds.

Figure 23:
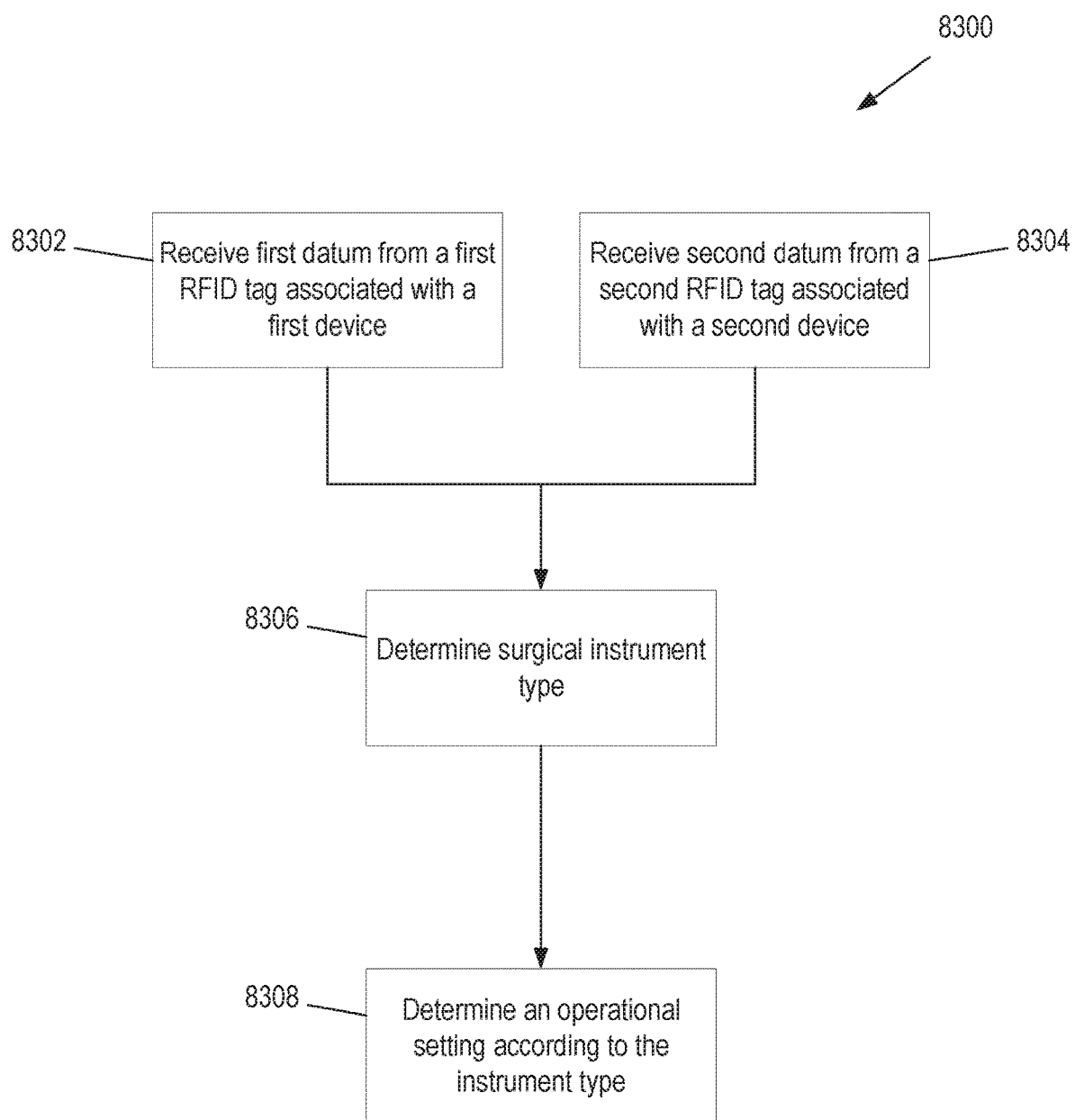
FIG. 23 illustrates a logic flow diagram of a process for determining surgical instrument operational settings via an RFID assembly, in accordance with at least one aspect of the present disclosure.

Further, the graph 8510 demonstrates that a control circuit 1210 executing the process 8300 illustrated in FIG. 23 or the process 8350 illustrated in FIG. 24 has received 8302, 8352 a first datum from the surgical instrument identifying the surgical instrument as a surgical stapler, received 8304, 8354 a second datum from the staple cartridge identifying the cartridge type, determined 8306, 8356 that the cartridge type is associated with a particular force threshold setting for the surgical stapler, and then controlled 8308, 8358 the surgical instrument to enforce the determined force threshold.

As demonstrated by FIG. 30, the various processes described herein, or any suitable portions thereof, can be utilized in conjunction with one other in any combination or arrangement for controlling a surgical instrument. Therefore, control systems 8111 implementing any combination of the described processes are intended to be within the scope of the present disclosure.

As yet another example, FIG. 31 illustrates a graph 8530 demonstrating the relationship between force, represented by the vertical axis 8532, and time, represented by the horizontal axis 8534, for a prophetic firing of a surgical stapler including a control system 8111 executing the process 8400 illustrated in FIG. 28. After clamping tissue, a surgical stapler is programmed to wait for a time period t, before cutting the clamped tissue or performing other actions. The wait time t, is a controllable parameter. In various aspects, the wait time t, can be manually selected by a user of the surgical stapler and/or controlled by a control system 8111 of the surgical stapler. In this example, the control circuit 1210 has received 8402 a first datum from the surgical instrument identifying the surgical instrument as a surgical stapler and/or from the staple cartridge identifying the cartridge type, received 8404 a second datum identifying the user, determined 8406 that the user identity is associated with a particular wait time t, setting for surgical staplers, and then controlled 8408 the surgical stapler to wait for a time period defined by the wait time t, setting, as indicated by the line 8536.

Figure 32:
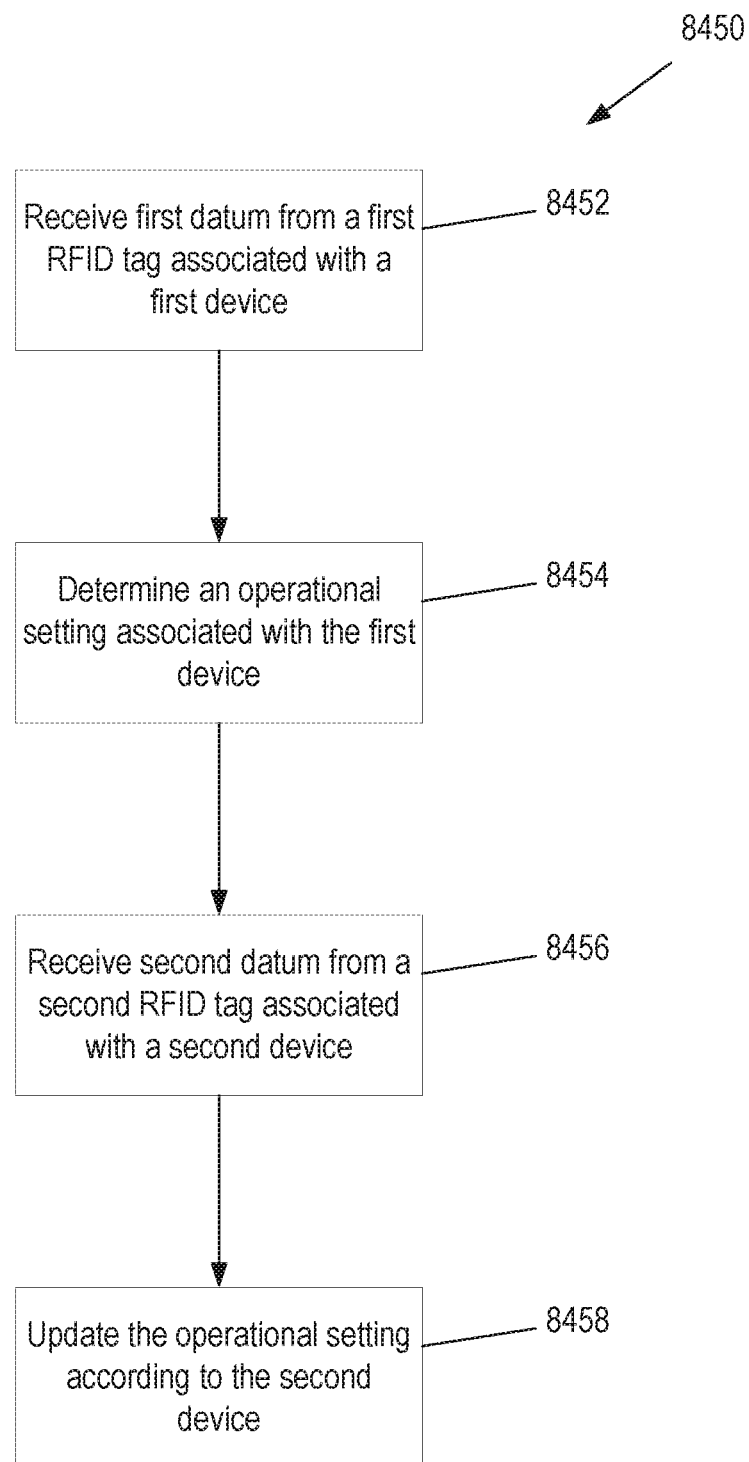
FIG. 32 illustrates a logic flow diagram of a process for successively updating an operational parameter via an RFID assembly, in accordance with at least one aspect of the present disclosure.

In one aspect, a control system 8111 for a surgical instrument 8002 can be configured to update an operational setting according to successively scanned devices. For example, the control system 8111 can execute the process 8450 illustrated in FIG. 32. Accordingly, the control circuit 1210 receives 8452 a first datum from a first RFID tag associated with a device or surgical instrument via one or more RFID scanners such as, for example, RFID scanners 8008 (FIG. 7A) to which the control circuit 1210 is coupled. Accordingly, the control circuit 1210 can determine 8454 an operational setting an operational setting based upon the scanned device. Further, the control circuit 1210 can thereafter receive 8456 a second datum from a second RFID tag associated with a second device via the RFID scanner 8008. Accordingly, the control circuit 1210 can update the determined operational setting according to the second device. For example, the control circuit 1210 can change the operational setting from a first value that is dependent on the first device to a second value that is dependent on both the first and second devices. The data received from the devices can indicate, for example, the serial number of the device, the device type, and/or characteristics or parameters associated with the device. As one example, the surgical instrument 8002 can include a trocar including an RFID scanner 8008. When a first device is inserted through the trocar, the control circuit 1210 can read the RFID tag associated with that first device and then update an operational setting associated with the surgical system based on the detection of that device. Then when a second device is inserted through the trocar, the control circuit 1210 can read the RFID tag associated with that second device and then update the operational setting accordingly. The operational setting in this example can include, for example, a generator power setting, a surgical stapler firing speed, or a counter tracking the number of device exchanges. Therefore, a control circuit 1210 executing the process 8450 can successively update operational settings as additional devices are introduced within the operating theater or surgical environment.

In one aspect, a control system 8111 for a surgical instrument 8002 can be configured to automatically update a default operational algorithm of the surgical instrument 8002 according to scanned components thereof. For example, the control system 8111 can execute a process 8700 illustrated in FIG. 33. Accordingly, the control circuit 1210 receives 8702 a first datum from a first RFID tag associated with a first device and receives 8704 a second datum from a second RFID tag associated with a second device via one or more RFID scanners such as, for example, RFID scanners 8008 (FIG. 7A) to which the control circuit 1210 is coupled. The received data can indicate, for example, the serial number of the device, the device type, and/or characteristics or parameters associated with the device. In one aspect, the RFID scanners 8008 can be positioned such that the RFID tags associated with each of the components are naturally read by the RFID scanners 8008 as a natural consequence of the assembly or utilization of the surgical instrument 8002, as described above in connection with FIGS. 13 and 14.

Furthermore, the control circuit 1210 can determine 8706 adjustments to a default control algorithm of the surgical instrument 8002 the received data. In addition, the control circuit 1210 can update 8708 the default control algorithm to an updated control algorithm based on the determined adjustments. The control algorithm can dictate how the surgical instrument 8002 itself (or a component thereof) is controlled or how a third device (e.g., a surgical generator that the surgical instrument 8002 is coupled to) is controlled.

Figure 33:
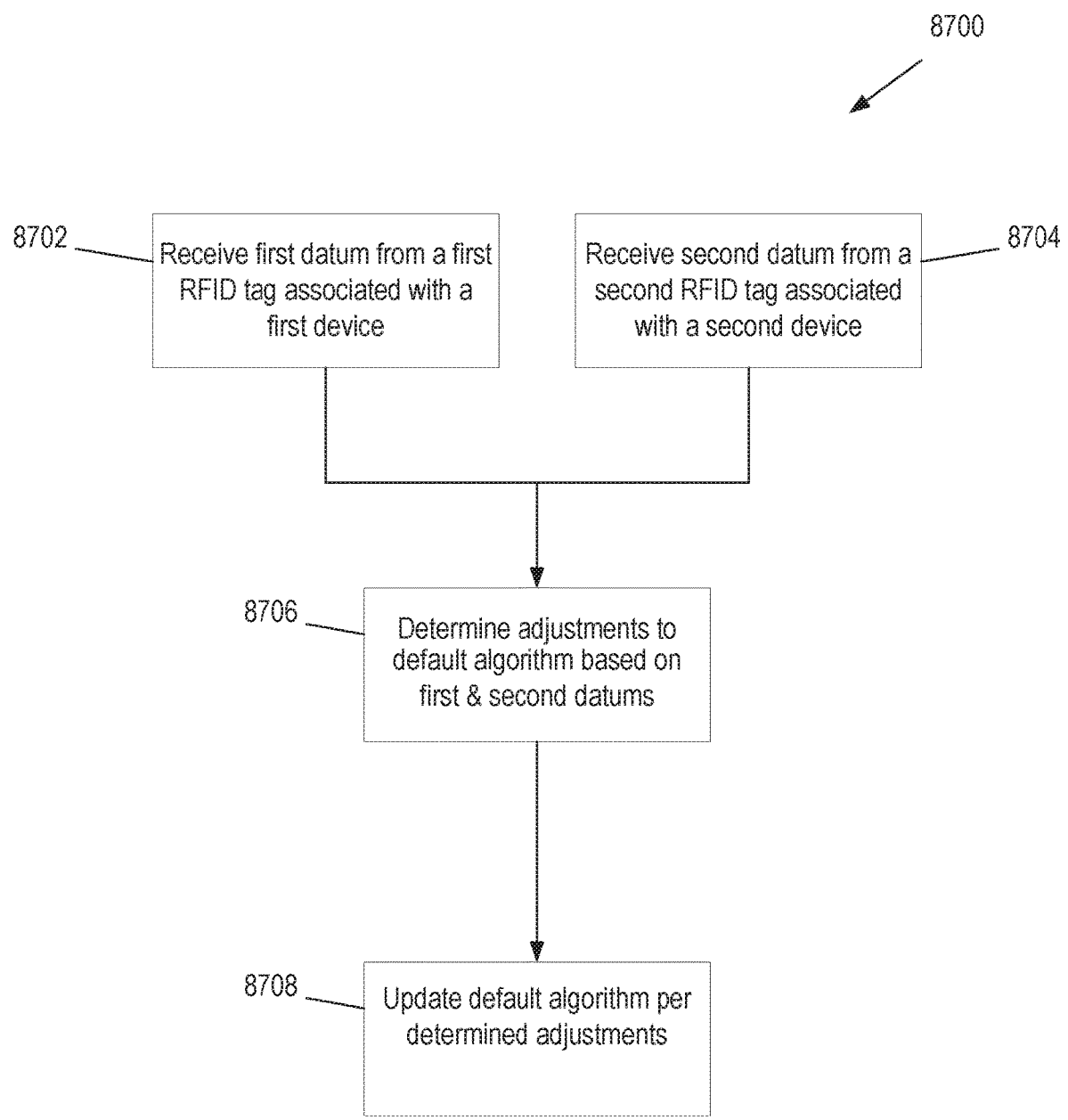
FIG. 33 illustrates a logic flow diagram of a process for updating a default operational algorithm of a surgical instrument via an RFID assembly, in accordance with at least one aspect of the present disclosure.

In one example in accordance with the process 8700 of FIG. 33, the surgical instrument 8002 is an ultrasonic surgical instrument, and the first and second devices are an ultrasonic transducer and an ultrasonic waveguide with RFID tags 8006 that store a first datum and a second datum, respectively, indicative of adjustments to a default natural frequency of the surgical instrument 8002. Ultrasonic surgical instruments are designed to operate within a defined frequency band or range (e.g. 53-57 kHz). Ultrasonic energy is used to drive a predefined displacement of an ultrasonic blade. The ultrasonic energy is transmitted from the ultrasonic transducer to the ultrasonic blade through the ultrasonic waveguide, in order to complete a desired tissue treatment function. The manufacturing process of the first and second devices can yield mass variations, material density variations, and/or assembly variations that can shift a natural frequency of ultrasonic surgical instrument and cause differences in the output displacement. Accordingly, during manufacturing each of the first and second devices can be tested to capture a natural frequency associated therewith. The RFID tags 8006 of the first device and the second device can store a first datum and a second datum, respectively, indicative of the captured natural frequencies.

Further to the above, the control circuit 1210 can be configured to determine 8706 adjustments to a default natural frequency of the surgical instrument 8002 based on the first datum and the second datum, can cause a generator or handle assembly associated with the surgical instrument 8002 to adjust the power delivered to the ultrasonic transducer to yield an updated 8708 natural frequency based on the determined adjustments. This would optimize the function and variation between devices by having the surgical instrument output tuned to the specific design and/or manufacturing parameters of its components. Additionally operating at the updated natural frequency would reduce undesirable stresses and lower opportunity of breakage. In at least one example, the control circuit 1210 can employ a lookup table of natural frequency adjustments for corresponding devices of the surgical instrument 8002, which can be identified via any suitable identification information such as, for example, a device number, type, or manufacturer transmitted.

For brevity, the various processes above are described as being executed by the control circuit 1210 illustrated in FIG. 7. However, this is a non-limiting example of a control circuit and it should be recognized that the depicted processes can be executed by circuitry that can include a variety of hardware and/or software components. As another example, the processes can be embodied as an ASIC that is configured to perform the described functions. As yet another example, the processes can be embodied as instructions stored in a memory coupled to a processor that, when executed by the processor, cause the processor or device to perform the described functions. A control circuit can include, for example, the control circuit 1210 illustrated in FIG. 7, the processor module 11232 of the surgical hub 11206 illustrated in FIGS. 5 and 6, and various other hardware and/or software components.

In various aspects, one of the first device and the second device utilized in the processes described in connection with FIGS. 17, 18, 20, 23, 33 can be a device packaging. In one example, the second device is a device packaging of the first device. In another example, the second device is a device packaging of a third device releasably couplable to the surgical instrument 8002. In at least one example, the first device is a housing assembly 8004*a* (FIG. 12), and the second device is a packaging of the housing assembly 8004*a*. In such example, the device packaging can include an RFID tag storing information about the housing assembly 8004*a*. The stored information can indicate whether the device packaging has been opened or tampered with, can indicate an expiration date of the packaged device, and/or can include compatibility and/or authenticity information.

Various aspects of the subject matter described herein are set out in the following examples.

EXAMPLE SET 1

Example 1—A control system for a surgical instrument for use with a surgical system, the surgical system comprising a first device and a second device, the control system comprising an RFID scanner and a control circuit coupled to the RFID scanner. The control circuit is configured to receive a first datum from a first RFID tag associated with a first device via the RFID scanner, receive a second datum from a second RFID tag associated with a second device via the RFID scanner, determine a communication protocol suitable for the first device and the second device according to the first datum and the second datum, and cause the surgical instrument to utilize the determined communication protocol for communicating with the first device and the second device.

Example 2—The control system of Example 1, wherein each of the first device and the second device is selected from the group consisting of a surgical hub, a visualization system, and a robotic surgical system.

Example 3—The control system of Examples 1 or 2, wherein the surgical instrument is selected from the group consisting of a surgical stapler, an electrosurgical instrument, an ultrasonic surgical instrument, a surgical clip applier, and a trocar.

Example 4—The control system of any one of Examples 1-3, wherein the control circuit is configured to receive an operational setting for the surgical instrument from at least one of the first device or the second device via the determined communication protocol.

Example 5—The control system of any one of Examples 1-3, wherein the control circuit is configured to transmit an operational setting to at least one of the first device or the second device via the determined communication protocol.

Example 6—A control system for a surgical instrument, the control system comprising an RFID scanner and a control circuit coupled to the RFID scanner and a display screen. The control circuit is configured to receive a first datum from a first RFID tag associated with a first device, receive a second datum from a second RFID tag associated with a second device, and determine a surgical procedure type according to the first datum and the second datum.

Example 7—The control system of Example 6, wherein at least one of the first device or the second device is a component of the surgical instrument.

Example 8—The control system of Example 7, wherein the component is selected from the group consisting of a hand piece, a battery, a motor assembly, a shaft, an end effector, and a consumable.

Example 9—The control system of any one of Examples 6-8, wherein at least one of the first device or the second device is selected from the group consisting of a surgical hub, a visualization system, and a robotic surgical system.

Example 10—The control system of any one of Examples 6-9, wherein the surgical instrument is selected from the group consisting of a surgical stapler, an electrosurgical instrument, an ultrasonic surgical instrument, a surgical clip applier, and a trocar.

Example 11—The control system of any one of Examples 6-10, further comprising the display screen, wherein the control circuit is further configured to cause the display screen to display information pertaining to the surgical procedure type.

Example 12—The control system of Example 11, wherein the information comprises steps of performing the surgical procedure type.

Example 13—A control system for a surgical instrument, the control system comprising an RFID scanner and a control circuit coupled to the RFID scanner and a display screen. The control circuit is configured to receive a first datum from a first RFID tag associated with the surgical instrument via the RFID scanner, the first datum identifying a device, receive a second datum from a second RFID tag via the RFID scanner, the second datum identifying a user, and determine a user setting corresponding to the user and the device.

Example 14—The control system of Example 13, wherein the second RFID tag is disposed on a band wearable by the user.

Example 15—The control system of Examples 13 or 14, wherein the surgical instrument is selected from the group consisting of a surgical stapler, an electrosurgical instrument, an ultrasonic surgical instrument, a surgical clip applier, and a trocar.

Example 16—The control system of any one of Examples 13-15, further comprising the display screen, wherein the control circuit is further configured to cause the display screen to display information pertaining to the surgical instrument according to the determined user setting.

Example 17—The control system of any one of Examples 13-16, wherein the determined user setting comprises a magnification for a visualization system.

Example 18—The control system of any one of Examples 13-16, wherein the determined user setting comprises a layout of a graphical user interface displayed by the display screen.

Example 19—The control system of any one of Examples 13-16, wherein the determined user setting comprises a customized operational setting for the surgical instrument.

EXAMPLE SET 2

Example 1—A control system for a surgical instrument, the control system comprising an RFID scanner and a control circuit coupled to the RFID scanner, the control circuit configured to receive a first datum from a first RFID tag associated with a first device via the RFID scanner, receive a second datum from a second RFID tag associated with a second device via the RFID scanner, and verify compatibility of the first device and the second device based on a comparison of the first datum and the second datum.

Example 2—The control system of Example 1, further comprising a display screen, wherein the control circuit is configured to provide an alert through the display screen that the first device and the second device are incompatible.

Example 3—The control system of Example 2, wherein the display screen is integral to a surgical hub to which the surgical instrument is communicably coupled.

Example 4—The control system of any one of Examples 1-3, wherein the first device comprises a first component of the surgical instrument and the second device comprises a second component of the surgical instrument.

Example 5—The control system of Example 4, wherein each of the first component and the second component is selected from the group consisting of a hand piece, a battery, a motor assembly, a shaft, an end effector, and a consumable.

Example 6—The control system of Examples 4 or 5, wherein the RFID scanner is positioned to read each of the first RFID tag and the second RFID tag as the first component and the second component are assembled to form the surgical instrument.

Example 7—The control system of Examples 4 or 5, wherein the RFID scanner comprises a first RFID scanner, the control system further comprising a second RFID scanner, and wherein the first RFID scanner is positioned to read the first RFID tag and the second RFID scanner is positioned to read the second RFID tag as the first component and the second component are assembled to form the surgical instrument.

Example 8—The control system of any one of Examples 1-7, wherein the control circuit is further configured to prevent operation of the surgical instrument according to the first device and the second device being incompatible.

Example 9—A control system for a surgical instrument, the control system comprising an RFID scanner and a control circuit coupled to the RFID scanner, the control circuit configured to receive a first datum from a first RFID tag associated with a first device via the RFID scanner, receive a second datum from a second RFID tag associated with a second device via the RFID scanner, determine that the first device is incompatible with the second device based on a comparison between the first datum and the second datum, and provide a suggestion for a third device as a replacement for the second device.

Example 10—The control system of Example 9, further comprising a display screen, wherein the control circuit is configured to provide an alert, and wherein the alert comprises a notification displayed via the display screen.

Example 11—The control system of Example 10, wherein the display screen is integral to a surgical hub to which the surgical instrument is communicably coupled.

Example 12—The control system of any one of Examples 9-11, wherein the first device comprises a first component of the surgical instrument and the second device comprises a second component of the surgical instrument.

Example 13—The control system of Example 12, wherein each of the first component and the second component is selected from the group consisting of a hand piece, a battery, a motor assembly, a shaft, an end effector, and a consumable.

Example 14—The control system of Examples 12 or 13, wherein the RFID scanner is positioned to read each of the first RFID tag and the second RFID tag as the first component and the second component are assembled to form the surgical instrument.

Example 15—The control system of Examples 12 or 13, wherein the RFID scanner comprises a first RFID scanner, the control system further comprising a second RFID scanner, wherein the first RFID scanner is positioned to read the first RFID tag and the second RFID scanner is positioned to read the second RFID tag as the first component and the second component are assembled to form the surgical instrument.

Example 16—The control system of any one of Examples 9-15, wherein determining that the first device and the second device are incompatible causes the control circuit to prevent operation of the surgical instrument.

Example 17—A control system for a surgical instrument, the surgical instrument for use with a surgical system, the control system comprising an RFID scanner and a control circuit coupled to the RFID scanner, the control circuit configured to receive a first datum from a first RFID tag associated with a first device via the RFID scanner, determine an operational setting for the surgical system according to the first datum, receive a second datum from a second RFID tag associated with a second device via the RFID scanner, and update the operational setting from a first value to a second value according to the first datum and the second datum.

Example 18—The control system of Example 17, wherein the operational setting is for the surgical instrument.

Example 19—The control system of Example 17, wherein the operational setting is for a third device of the surgical system.

Example 20—The control system of any one of Examples 17-19, wherein the RFID scanner is configured to read each of the first RFID tag and the second RFID tag as a result of the first device and the second device being utilized in conjunction with the surgical instrument.

Example 21—The control system of any one of Examples 17-20, wherein the surgical instrument comprises a trocar, and the RFID scanner is positioned to read each of the first RFID tag of the first device and the second RFID tag of the second device as they are inserted through the trocar.

EXAMPLE SET 3

Example 1—A control system for a surgical instrument, the surgical instrument comprising a first device and a second device, the control system comprising an RFID scanner and a control circuit coupled to the RFID scanner, the control circuit configured to receive a first datum from a first RFID tag associated with the first device via the RFID scanner, receive a second datum from a second RFID tag associated with the second device via the RFID scanner, determine a type of the surgical instrument according to the first datum and the second datum, and determine an operational setting according to the surgical instrument type.

Example 2—The control system of Example 1, wherein the first device comprises a first component of the surgical instrument and the second device comprises a second component of the surgical instrument.

Example 3—The control system of Example 2, wherein each of the first component and the second component is selected from the group consisting of a hand piece, a battery, a motor assembly, a shaft, an end effector, and a consumable.

Example 4—The control system of Examples 2 or 3, wherein the RFID scanner is positioned to read each of the first RFID tag and the second RFID tag as the first component and the second component are assembled to form the surgical instrument.

Example 5—The control system of Examples 2 or 3, wherein the RFID scanner comprises a first RFID scanner, the control system further comprising a second RFID scanner, wherein the first RFID scanner is positioned to read the first RFID tag and the second RFID scanner is positioned to read the second RFID tag as the first component and the second component are assembled to form the surgical instrument.

Example 6—The control system of any one of Examples 1-5, wherein the control system is integral to the surgical instrument.

Example 7—The control system of any one of Examples 1-5, wherein the control system is integral to a surgical hub to which the surgical instrument is communicably couplable.

Example 8—The control system of any one of Examples 1-7, wherein the operational setting is for the surgical instrument.

Example 9—The control system of any one of Examples 1-7, wherein the operational setting is for a third device to which the surgical instrument is communicably couplable.

Example 10—A control system for a surgical instrument, the control system comprising an RFID scanner and a control circuit coupled to the RFID scanner, the control circuit configured to receive a first datum from a first RFID tag associated with the surgical instrument via the RFID scanner, the first datum identifying the surgical instrument, receive a second datum from a second RFID tag associated with a consumable device for use with the surgical instrument via the RFID scanner in response to the consumable device being inserted into the surgical instrument, the second datum identifying the consumable device, determine an operational setting corresponding to the surgical instrument and the consumable device, and control the surgical instrument according to the determined operational setting.

Example 11

The control system of Example 10, wherein the surgical instrument comprises a clip applier, the consumable device comprises a surgical clip, and the operational setting is selected from the group consisting of a force profile applied by the surgical instrument to the surgical clip or a maximum force applied by the surgical instrument to the surgical clip.

Example 12—The control system of Example 10, wherein the surgical instrument comprises a stapler, the stapler comprising, an I-beam and a motor configured to drive the I-beam between a first position and a second position, the consumable device comprises a staple cartridge, and the operational setting comprises a speed at which the motor drives the !-beam.

Example 13—The control system of any one of Examples 10-12, wherein the control system is integral to the surgical instrument.

Example 14—The control system of any one of Examples 10-12, wherein the control system is integral to a surgical hub to which the surgical instrument is communicably couplable.

Example 15—The control system of any one of Examples 10-14, wherein the operational setting is for the surgical instrument.

Example 16—The control system of any one of Examples 10-14, wherein the operational setting is for a third device to which the surgical instrument is communicably couplable.

Example 17—A control system for a surgical instrument, the control system comprising an RFID scanner and a control circuit coupled to the RFID scanner, the control circuit configured to receive a first datum from a first RFID tag associated with the surgical instrument via the RFID scanner, the first datum identifying the surgical instrument, receive a second datum from a second RFID tag via the RFID scanner, the second datum identifying a user of the surgical instrument, determine an operational setting corresponding to the user and the surgical instrument, and control the surgical instrument according to the determined operational setting.

Example 18—The control system of Example 17, wherein the control circuit is configured to retrieve an operational range corresponding to a parameter of the surgical instrument and select the operational setting from within the operational range according to the user.

Example 19—The control system of Examples 17 or 18, wherein the first RFID tag is associated with a component of the surgical instrument.

Example 20—The control system of Example 19, wherein the RFID scanner is positioned to read the first RFID tag as the component is coupled to the surgical instrument.

Example 21—The control system of any one of Examples 17-20, wherein the second RFID tag is disposed on a band wearable by the user.

Example 22—The control system of any one of Examples 17-21, wherein the operational setting is selected from the group consisting of a staple height, a power level of the surgical instrument, a closure speed at which a motor coupled to an end effector of the surgical instrument cause the end effector to close, a firing speed at which a motor coupled to a firing member of the surgical instrument causes the firing member to advance, and a resonant frequency of an ultrasonic blade of the surgical instrument.

Example 23—The control system of any one of Examples 17-22, wherein the control system is integral to the surgical instrument.

Example 24—The control system of any one of Examples 17-22, wherein the control system is integral to a surgical hub to which the surgical instrument is communicably couplable.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

In various aspects, a microcontroller of control circuit in accordance with the present disclosure may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the housing portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A control system for a surgical instrument, the control system comprising:
    an RFID scanner; and
    a control circuit coupled to the RFID scanner, the control circuit configured to:
        receive a first datum from a first RFID tag associated with a first component of the surgical instrument via the RFID scanner;
        receive a second datum from a second RFID tag associated with a second component of the surgical instrument via the RFID scanner;
        determine that the first component is compatible with the second component based on a comparison of the first datum and the second datum when the first component and the second component are assembled to the surgical instrument; and
        establish a communication protocol for communicating with the first component and the second component based on the first datum and the second datum when the first component and the second component are assembled to the surgical instrument.

2. The control system of claim 1, further comprising:
    a display screen;
    wherein the control circuit is configured to provide an alert through the display screen that the first component and the second component are incompatible.

3. The control system of claim 2, wherein the display screen is integral to a surgical hub to which the surgical instrument is communicably coupled.

4. The control system of claim 1, wherein each of the first component and the second component is selected from the group consisting of a hand piece, a battery, a motor assembly, a shaft, an end effector, and a consumable.

5. The control system of claim 1, wherein the RFID scanner is positioned to read each of the first RFID tag and the second RFID tag as the first component and the second component are assembled to form the surgical instrument.

6. The control system of claim 1, wherein the RFID scanner comprises a first RFID scanner, the control system further comprising:
    a second RFID scanner; and
    wherein the first RFID scanner is positioned to read the first RFID tag and the second RFID scanner is positioned to read the second RFID tag as the first component and the second component are assembled to form the surgical instrument.

7. The control system of claim 1, wherein the control circuit is further configured to prevent operation of the surgical instrument according to the first component and the second component being incompatible.

8. The control system of claim 1, wherein the control system is further configured to provide a suggestion to a user of the surgical instrument for a third component as a replacement for the second component.

9. A control system for a surgical instrument, the control system comprising:
    an RFID scanner; and
    a control circuit coupled to the RFID scanner, the control circuit configured to:
        receive a first datum from a first RFID tag associated with a first device via the RFID scanner;
        receive a second datum from a second RFID tag associated with a second device via the RFID scanner;
        determine that the first device is incompatible with the second device based on a comparison between the first datum and the second datum;

identify a third device that is compatible with the first device based on the comparison between the first datum and the second datum; and provide a suggestion to a user of the surgical instrument for the third device as a replacement for the second device.

10. The control system of claim 9, further comprising:
a display screen;
wherein the control circuit is configured to provide an alert, and wherein the alert comprises a notification displayed via the display screen.

11. The control system of claim 10, wherein the display screen is integral to a surgical hub to which the surgical instrument is communicably coupled.

12. The control system of claim 9, wherein the first device comprises a first component of the surgical instrument and the second device comprises a second component of the surgical instrument.

13. The control system of claim 12, wherein each of the first component and the second component is selected from the group consisting of a hand piece, a battery, a motor assembly, a shaft, an end effector, and a consumable.

14. The control system of claim 12, wherein the RFID scanner is positioned to read each of the first RFID tag and the second RFID tag as the first component and the second component are assembled to form the surgical instrument.

15. The control system of claim 12, wherein the RFID scanner comprises a first RFID scanner, the control system further comprising:
a second RFID scanner;
wherein the first RFID scanner is positioned to read the first RFID tag and the second RFID scanner is positioned to read the second RFID tag as the first component and the second component are assembled to form the surgical instrument.

16. The control system of claim 9, wherein determining that the first device and the second device are incompatible causes the control circuit to prevent operation of the surgical instrument.

17. A control system for a surgical instrument, the surgical instrument for use with a surgical system, the control system comprising:
an RFID scanner; and
a control circuit coupled to the RFID scanner, the control circuit configured to:
receive a first datum from a first RFID tag associated with a first device of the surgical instrument via the RFID scanner;
determine an operational setting for the surgical system according to the first datum;
receive a second datum from a second RFID tag associated with a second device of the surgical instrument via the RFID scanner; and
update the operational setting from a first value to a second value based on a comparison of the first datum and the second datum when the first device and the second device are assembled to the surgical system, wherein the operational setting is dependent on the compatibility of the first device and the second device with each other.

18. The control system of claim 17, wherein the operational setting is for the surgical instrument.

19. The control system of claim 17, wherein the operational setting is for a third device of the surgical system.

20. The control system of claim 17, wherein the RFID scanner is configured to read each of the first RFID tag and the second RFID tag as a result of the first device and the second device being utilized in conjunction with the surgical instrument.

21. The control system of claim 17, wherein:
the surgical instrument comprises a trocar; and
the RFID scanner is positioned to read each of the first RFID tag of the first device and the second RFID tag of the second device as they are inserted through the trocar.

22. The control system of claim 17, wherein the control system is further configured to provide a suggestion to a user of the surgical instrument for a third device as a replacement for the second device.

23. A control system for a surgical instrument, the control system comprising:
an RFID scanner; and
a control circuit coupled to the RFID scanner, the control circuit configured to:
receive a first datum from a first RFID tag associated with a first component of the surgical instrument via the RFID scanner;
receive a second datum from a second RFID tag associated with a second component of the surgical instrument via the RFID scanner;
determine that the first component is not compatible with the second component based on the first datum and the second datum; and
prevent an operation of the surgical instrument based on the determined incompatibility of the first component with the second component.

* * * * *